US008969253B2

(12) United States Patent
Reiersen et al.

(10) Patent No.: US 8,969,253 B2
(45) Date of Patent: Mar. 3, 2015

(54) METHOD FOR SCREENING PHAGE DISPLAY LIBRARIES AGAINST EACH OTHER

(75) Inventors: Herald Reiersen, Sofiemyr (NO); Geir Age Loset, Drøbak (NO); Urs Beat Hagemann, Oslo (NO)

(73) Assignee: Nextera AS, Oslo (NO)

( * ) Notice: Subject to any disclaimer, the term of this patent is extended or adjusted under 35 U.S.C. 154(b) by 284 days.

(21) Appl. No.: 13/203,498

(22) PCT Filed: Feb. 26, 2010

(86) PCT No.: PCT/GB2010/000340
§ 371 (c)(1), (2), (4) Date: Aug. 26, 2011

(87) PCT Pub. No.: WO2010/097589
PCT Pub. Date: Sep. 2, 2010

(65) Prior Publication Data

US 2011/0318269 A1 Dec. 29, 2011

Related U.S. Application Data

(60) Provisional application No. 61/155,714, filed on Feb. 26, 2009.

(30) Foreign Application Priority Data

Feb. 26, 2009 (GB) .................................. 0903316.8

(51) Int. Cl.

| | |
|---|---|
| ***C40B 30/04*** | (2006.01) |
| ***C12N 15/10*** | (2006.01) |
| ***C40B 40/08*** | (2006.01) |
| ***C40B 50/06*** | (2006.01) |

(52) U.S. Cl.
CPC ............ *C12N 15/1037* (2013.01); *C40B 40/08* (2013.01); *C40B 50/06* (2013.01)
USPC .............................................................. 506/9

(58) Field of Classification Search
None
See application file for complete search history.

(56) References Cited

U.S. PATENT DOCUMENTS

2005/0208577 A1 9/2005 Michnick et al.

FOREIGN PATENT DOCUMENTS

WO 2007001694 1/2007
WO 2009024591 2/2009

OTHER PUBLICATIONS

Sahin, U. et al., Human neoplasms elicit multiple specific immune responses in the autologous host, PNAS (1995) 92:11810-3.
Eriksson, T. et al., Cloning of three new allergens from the dust mite Lepidoglyphus destuctor using phage surface display technology, Eur. J. Biochem. (2001) 268: 287-94.

(Continued)

*Primary Examiner* — Christian Boesen
(74) *Attorney, Agent, or Firm* — Roylance, Abrams, Berdo & Goodman, L.L.P.

(57) ABSTRACT

The present invention relates to a method for screening phage display libraries against each other. In particular, the invention relates to a method for screening at least two phage display libraries against each other to identify and/or select one or more interacting binding partners or binding molecules making up such interacting binding partners. Kits providing two bispecific phage display libraries are also provided.

18 Claims, 28 Drawing Sheets

(56) References Cited

OTHER PUBLICATIONS

Figure 1:
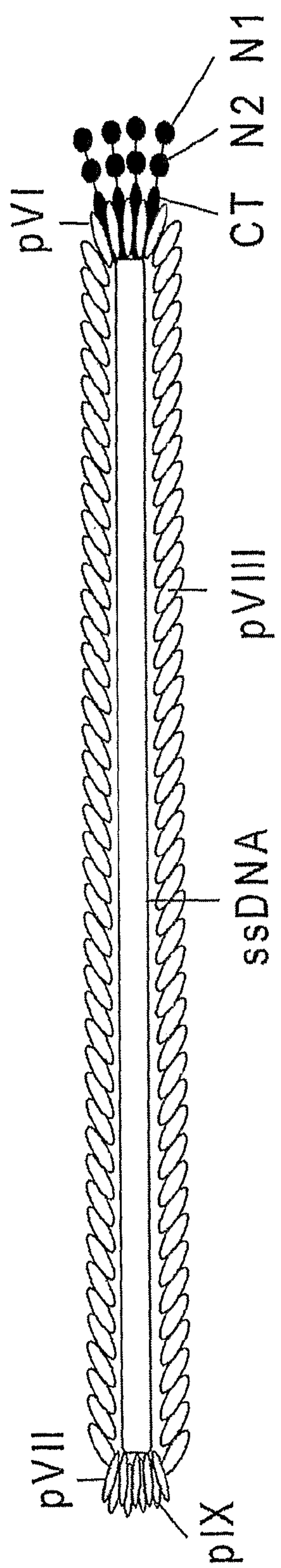

Fossa, A. et al., Serological cloning of cancer/testis antigens expressed in prostate cancer using cDNA phage surface display, Cancer Immunol. Immunother. (2004) 53:431-8.
Krebber, C. et al., Co-selection of cognate antibody-antigen pairs by selectively-infective phages, FEBS Lett. (1995) 377:227-31.
Pelletier, J. et al., An in vivo library-versus-library selection of optimized protein-protein interactions, Nat. Biotech. (1999) 17:683-90.
Endemann, H. et al., Location of Filamentous Phage Minor Coat Proteins in Phage and in Infected Cells, J. Mol. Biol. (1995) 250: 496-506.
Gao, C. et al, Making artificial antibodies: A format for phage display of combinatorial heterodimeric arrays, PNAS (1999) 96:6025-30.
Kwasnikowski, P. et al., Multivalent display system on filamentous bacteriophage pVll minor coat protein, J. Immunol. Methods (2005) 307:135-43.
Khalil, A. et al., Single M13 bacteriophage tethering and stretching, PNAS (2007) 104:4892-7.
Loset, G. et al., Reliable titration of filamentous bacteriophages independent of pIII fusion moiety and genome size by using trypsin to restore wild-type pIII phenotype, Biotechniques (2008) 44:551-3.
Loset, G. et al., Functional phage display of two murine alpha/beta T-cell receptors is strongly dependent on fusion format, mode and periplasmic folding assistance, Protein Eng. Des. Sel. (2007) 20:461-72.
Simons, G. et al., Genes VI, VII, and IX of phage M13 code for minor capsid proteins of the virion, PNAS (1981) 78:4194-8.
Bradbury, A. et al., Antibodies from phage antibody libraries, J. Immunol. Methods (2004) 290:29-49.
De Haard, H. et al., A large non-immunized human Fab fragment phage library that permits rapid isolation and kinetic analysis of high affinity antibodies, J. Biol. Chem. (1999) 274:18218-30.
Hoogenboom, H., Selecting and screening recombinant antibody libraries, Nat. Biotechnol. (2005) 23:1105-16.
Scholle, M. et al., Mapping protease substrates by using a biotinylated phage substrate, Chembiochem. (2006) 7:834-8.
Dwek, R., Antibodies and antigens: It's all about the numbers game, PNAS (2009) 106:2087-8.
Bowley, Diana R. et al., Libraries against libraries for combinatorial selection of replicating antigen-antibody pairs, Proceedings of the National Academy of Sciences of the United States of America, vol. 106, No. 5, Feb. 2009, pp. 1380-1385.
Jaye, D.L. et al., Direct fluorochrome labeling of phage display library clones for studying binding specificities: applications in flow cytometry and fluorescence microscopy, Journal of Immunological Methods, vol. 295, No. 1-2, Dec. 1, 2004, pp. 119-127.
Dai, M. et al., Using T7 phage display to select GFP-based binders, Protein Engineering Design & Selection, vol. 21, No. 7, Jul. 2008, pp. 413-424.
Slootweg, Erik J. et al., Fluorescent T7 display phages obtained by translational frameshift, Nucleic Acids Research, vol. 34, No. 20, e 137, 11 pages, Oct. 13, 2006.
Spada, S. et al., Selectively Infective Phage (SIP) Technology: A Novel Method for In vivo Selection of Interacting Protein-Ligand Pairs, Nature Medicine, vol. 3, No. 6, Jun. 1997, pp. 694-696.
International Search Report issued in PCT/GB2010/000340 dated Aug. 6, 2010.

Mean difference: 30.97 %

B.

```
DNA (org):  GGT CTG AAC GAC ATC TTC GAG GCT CAG AAA ATC GAA TGG CAC GAA
DNA (mod):  GGC CTG AAC GAT ATC TTT GAA GCG CAG AAA ATT GAA TGG CAT GAA
       aa:   G   L   N   D   I   F   E   A   Q   K   I   E   W   H   E
```

C.

```
DNA: GAC TAC AAG GAC GAT GAC GAC AAG
 aa:  D   Y   K   D   D   D   D   K
```

D.

```
DNA: CAT CAC CAT CAC CAT CAC
 aa:  H   H   H   H   H   H
```

METHOD FOR SCREENING PHAGE DISPLAY LIBRARIES AGAINST EACH OTHER

This invention relates to a method for screening phage display libraries against each other. In particular, the invention relates to a method for screening at least two phage display libraries against each other to identify and/or select one or more interacting binding partners or binding molecules making up such interacting binding partners.

Methods and systems which enable the screening of two libraries against each other are highly desirable. Being able to screen two libraries against each other offers two major advantages. Conventional screening with only one library requires that the baits or targets on which those libraries are screened are limited in number, often only one defined target (e.g. one defined target antigen). This means that only library members binding to a limited number of antigens can be isolated in one step. However, if a single defined bait or target can be replaced by a large library, many more combinations of binders can be isolated. In general, libraries having a large number of members are preferable to those with fewer members.

In addition, using library versus library selections saves a lot of processing time. Normally selecting one specific library A against members from a second library B requires initial characterisation of members from B. This implies stepwise identification of appropriate library member B, and cloning, expression and purification of individual members prior to selection of library members from A reacting with each member B. This generates a bottleneck in the process. Making two different libraries A & B which can be expressed simultaneously, and can be selected against each other, has the advantage that most of the interacting pairs from both libraries can identified in few steps. This accelerates the identification process. For example allowing an antibody library to react against a cancer cell antigen library ensures that all immunogenic antigens present for which there are antibodies reacting with, will be enriched for. Thus, today there is a demand for high throughput selection of library vs library members.

To date, however, there have not been many systems described which allow such library versus library screening to be successfully performed. One method in which cDNA from cancer cells expressing its antigen repertoïre has been used to identify self antibodies in sera of patients, is the SEREX technology (Sahin et al, PNAS 92, 11810-11813, 1995; Eriksson, et al. Eur J. Biochem. 268, 287-294, 2001; Fosså et al, Cancer Immunol. Immunother. 53, 431-438, 2004).

Selectively infective phage (Krebber et al, FEBS Lett 377, 277-231, 1995) and in vivo selection of complementary binding pairs using protein fragment complementation (Pelletier et al, Nat. Biotechnol 17, 683-690, 1999) are two examples of other selection methods. However, these methods have had limited success. Recently, Bowley et al. described a method to select phage display expressed libraries against yeast expressed libraries (Bowley, et al, PNAS 106(5), 1380.1386, 2009). Use of yeast libraries has some disadvantages relative to phage libraries in that the library size is limited. In addition, a different type of glycosylation present in yeast compared to human cells may mask important epitopes of human proteins. In addition, those methods which have been described are, in the main, quite laborious and time consuming.

It would therefore be highly advantageous and desirable to have improved systems and methods for library versus library screening, for example, systems and methods which can enable such screening to be carried out in shorter timescales and with a high success rate of identifying interacting library members and the individual library members taking part in such interactions. It is also advantageous if there are no systematic restrictions on the size of libraries.

The use of combinatorial approaches for protein identification, characterization and modification has been highly successful in both academic and commercial research and development. In this respect, filamentous bacteriophage, or phage, display technology has paved the way being the first library platform and still reigns as the dominating technology. Thus, phage display is widely applied in both basic and applied protein discovery, as well as in development of both novel protein-based diagnostics and therapeutics, which are the class of compounds most rapidly growing world-wide.

The principle of combinatorial phage display technology is based on the genotype-phenotype linkage offered by the property that each virion will only display on its surface the very same proteins that are encoded by the genome encapsulated by its protein coat. The phage particle itself is highly resistant to a variety of physiochemical conditions; hence phage display offers superior versatility in many selection regimes as compared to competing combinatorial technologies.

Phage display of heterologous polypeptides has been achieved using all five structural proteins of the filamentous phage coat, but only pIII- and to some extent pVIII-display have gained widespread use (FIG. 1).

When the heterologous fusion is only a short peptide, multivalent display systems using phage genome-based vectors are preferred, whereas for larger fusions requiring folded domains most applications will benefit from the phagemid systems. In the latter case, antibody-pIII phage display is by far dominating the field, but alternative scaffolds are emerging, continuing the need for expansion of protein engineering tools of tomorrow. For many applications, it would be highly advantageous to be able to make, specifically and in a controlled manner, bispecific phage particles such that more than one of the different types of coat proteins display a fusion peptide in the context of the same virus particle. Also, such a system should not interfere with already established display approaches and in particular pIII and pVIII display.

Endemann and Model, 1995, reported that the minor coat protein pVII was not accessible in the intact phage and that pVII was not functional with another protein fused to its N-terminus. Thus, this report concluded that pVII cannot be used for phage display.

Gao et al, 1999, and patent application WO0071694, describes heterologous peptide phage display on pVII using the octapeptide FLAG tag, as well as simultaneous phage display on pVII and pIX to generate functional heterodimeric polypeptides harbouring complex folding topologies (antibody Fv). These authors aimed at developing an alternative means for antibody display. The pVII and pIX fusion proteins were expressed from a phagemid employing a dicistronic constellation, hence the resulting functional phage particles inevitably contained varying amounts of pVII and pIX fusion proteins due to complementation by wild type pVII and pIX protein donated from the helper phage genome. As mentioned above, it had previously been suggested that pVII and pIX were not functional with another protein fused to their N termini, and Gao et. al. gave two possible reasons for their success, either alone or by the combination of both.

One possible reason was that a prokaryotic leader sequence (signal sequence) was attached N-terminally to the fusion proteins, thus ensuring targeting of the recombinant protein to the periplasmic space and thereby prevented accumulation in the cytoplasm. Another possible reason was that the recombinant proteins were expressed from a phagemid, not a phage genome as by Endemann and Model, hence wild type pVII and pIX from the helper phage inevitably needed for phagemid rescue were complementing the recombinant pVII and pIX fusion proteins, thus preserving wildtype functionality that otherwise may have been lost due to the recombinant modification. I.e. the phages would comprise a mix of wild-type and fusion proteins. The authors mention that the pVII-pIX display format would be particular useful for combinatorial display of heterodimeric arrays, which, for unknown reasons, appear to yield a particular powerful enrichment during panning protocols. The authors do not envisage using pVII as sole displaying protein (as phagemid or phage genome) or using pVII display in combination with display at another coat protein (different from pIX) to achieve bispecific display.

Kwasnikowski et al., 2005, described genetically stable fusion of scFv fragments to gene VII directly in the phage genome. I.e. the resulting phages comprised no native pVII protein, and the pVII display was multivalent. The authors speculate that one of the reasons for successful pVII display in the phage genome format is that they supported the fusion gene with a prokaryotic signal sequence that directs the fusion protein to the periplasmic space. The authors argued that the unique feature of their system is that the pVII displaying phages bears unmodified, wild-type pIII minor coat protein. Since it has been reported that multiple copies of functional pIII are required for host cell infection, the presence of wild-type pIII on the phage surface may facilitate recovery of selected antibodies with larger diversity. Thus, the authors do not envisage bispecific display, nor do they envisage pVII display without a prokaryotic signal sequence targeting to the periplasmic space.

Khalil et al., 2007, describes an application exploiting the feature of a bispecific filamentous phage virion in which an exogenous peptide is displayed at each distal tip of the very same virion. They achieved this by using the combination of a common pIII phage genome vector complementing a pIX display phagemid. In this setting, the phage genome vector served as a helper phage in rescuing the phagemid, thus being reminiscent of one of the approaches described herein of creating a bispecific phagemid virion by rescuing a pIII display phagemid by the use of a pVII modified helper phage genome. Moreover, the bispecific virions of Khalil et al display a peptide-pIII fusion that allows for a controlled biotinylation of their virion. There are however, several features that differ between these two avenues of obtaining a bispecific virion, as well as obtaining defined virion biotinylation, which make them unique from each other.

Firstly, the approach of Khalil et al cannot be used in combination with pIII phagemid display, as it is their phage genome vector that carries their pIII fusion, hence bispecificity cannot be obtained upon phagemid rescue and it would also highly likely be deleterious to the functionality of both pIII fusions.

Secondly, and as the authors also themselves pinpoint, genomic pIX modifications are not regarded as a viable strategy due to overlapping genes in the phage genome, thus they do not envision or speculate in making any modified helper phage genome that can be used for pIII phagemid (or pVIII) rescue and by this way donate a defined phenotypic feature to both distal tips of the very same virion. Khalil et al do not mention the use of modified pVII in either phagemid, or phage genome display.

Thirdly, Khalil et al do not speculate in modifying a single phage genome to achieve a bispecific virion, by exploiting simultaneous modification of more than one capsid gene within the very same genome. They merely use standard pIII peptide display through a commercially available phage genome vector.

Forth, Khalil et al only make bispecific virions displaying short peptides, not folded domains, and do never speculate in exploiting such display at either one, or both modified capsid proteins.

Fifth, Khalil et al achieve site-specific biotinylation of their pIII displayed peptide through in vitro chemical conjugation, not by an enzymatic reaction either in vitro or in vivo. The authors never envision enzyme mediated biotinylation of a displayed moiety by displaying an enzymatic substrate such as AviTag.

Finally, Khalil et al. does not show any type of display without the use of a N-terminal signal sequence.

Described herein is an alternative scaffold for peptides displayed on filamentous phages. Also described herein are bispecific phage particles in which more than one of the different types of coat proteins of the phage display a heterologous polypeptide in the context of the same virus particle. Also described herein are improved systems and methods of screening libraries of molecules against each other, i.e. library versus library screening.

Advantageously, and importantly the present method significantly reduces the time required to screen two or more libraries against each other and to analyse the binding partners identified or selected by such screening methods.

Thus, at its most general the present invention provides a method for screening at least two phage display libraries against each other to identify and/or select one or more interacting binding partners comprising:

(a) providing a first phage display library, wherein phages of said first phage display library are bispecific and comprise a member of a first library displayed at a first position and a first tag displayed at a second position;

(b) contacting said first bispecific phage display library with a second phage display library, wherein phages of said second phage display library comprise a member of a second library displayed at a first position;

(c) separating members of the second library which have become bound to members of the first library (i.e. interacting binding partners or library 1-library 2 complexes).

Such a separation step has the effect of separating members of the second library which have become bound to members of the first library (i.e. interacting binding partners or library 1-library 2 complexes) from certain other components of the reaction mixture.

In preferred embodiments of the invention said second phage display library is a bispecific phage display library, wherein phages of said second bispecific phage display library comprise a member of a second library displayed at a first position and a second tag displayed at a second position. Such methods involving two bispecific phage display libraries with different tags have the advantage of allowing better enrichment of interacting binding partners, better separation of the different phage library pools and increased specificity. This is particularly the case where both tags are utilized in the separation and purification steps (e.g. using a two step purification step as described in more detail below).

In preferred embodiments of the invention such a separation step is carried out by FACS techniques or by one or more steps which comprise immobilizing either the first or the second phage display library onto a solid phase by way of the tags associated with the appropriate phage display libraries. Thus, if the first bispecific phage display library is immobilized onto a solid phase in the methods of the invention, then the immobilization is carried out by way of said first tag. If the second bispecific phage display library is immobilized onto a solid phase in the methods of the invention, then the immobilization is carried out by way of said second tag.

In methods where an immobilization step is involved to enable the separation then said immobilization of either the first or second phage display library onto a solid phase can take place either before or after the contacting step (b). Such an immobilization step is also referred to herein as the initial or the first immobilization step.

In methods comprising an immobilization step to enable separation to take place then such a separation step has the effect of separating library 1-library 2 complexes from members of the non-immobilized phage display library which have not formed complexes, i.e. if the first phage display library is immobilized onto a solid phase, then the separation step allows the separation of library 1-library2 complexes from members of the second library which have not become bound to members of the first library. On the other hand, if the second phage display library is immobilized onto a solid phase, then the separation step allows the separation of library1-library2 complexes from members of the first library which have not become bound to members of the second library.

In methods of the invention where FACS techniques are used to enable separation of library 1-library 2 complexes then such methods generally involve the association of one type of fluorescent label with the phage particles of one of the phage display libraries and the association of a different type of fluorescent label with the phage particles of the second of the phage display libraries. The double labelled phage-phage complexes (i.e. the library 1-library2 complexes) can then be sorted from the non-bound/non complexed (single label) phage particles using FACS techniques. Thus, the double labeled phage complexes can be sorted using two different fluorescent labels which can be gated and correlated with the phage size corresponding to the double phage complex.

The association of appropriate fluorescent labels with the phage particles can be carried out by any appropriate technique which will enable a different type of fluorescence label to be associated with the members of phage display library 1 and the members of phage display library 2. Conveniently however, fluorescently labelled antibodies could be used for this purpose. Most conveniently, fluorescently labelled antibodies to tag 1 and/or tag 2, preferably tag 1 and tag 2, will be used. Alternatively, or in addition however, fluorescently labelled antibodies to one or more phage coat proteins or to additional tags incorporated into members of library 1 and/or library 2 displayed at said first position as outlined above could be used.

Other additional labels or tags could be added to the members of phage display library 1 and phage display library 2 in order to aid the FACS techniques. For example, to improve on the effectiveness of FACS sorting, one of the anti-tag antibodies can be attached to a non-magnetic bead, or fluorescent bead, in order to increase the size of the phage-phage complex and thereby aid the separation of the phage-phage complexes from unbound phage by increasing the size differential.

After the separation step (c) the interacting binding partners (library 1-library 2 complexes) can then be further manipulated or analysed. For example, in embodiments involving immobilization the presence of the tag which was not used to immobilize the phage display library can be used to identify library 1-library 2 complexes for further manipulation or analysis. In embodiments involving FACS then library 1-library 2 complexes will have been separated away from non-complexed library members and can be subjected to further manipulation or analysis.

The library 1-library 2 complexes can be analysed or further manipulated by any suitable methods, for example, in order to identify or characterise one or more members of the interacting binding partners making up one or more of the library 1-library 2 complexes. Suitable methods would be standard practice to one of skill in the art and include one or more of PCR amplification of gene products, cloning gene products into vectors such as expression vectors, screening methods such as filter screening or other array based screening methods, ELISA or FACS. Some of these methods are described in more detail elsewhere herein.

Appropriate methods are generally chosen depending on the number of interacting binding partners which have been identified and selected by the methods of the present invention and therefore require analysis. For example, if a relatively high number has been identified then a larger scale analysis method is generally preferred, e.g. filter or other array based screening, or FACS analysis. If a relatively small number have been identified then a smaller scale analysis such as ELISA is generally preferred.

These methods of analysis are of course all aided significantly by the fact that the library 1-library 2 complexes are displayed on the surfaces of phage particles and the nucleic acid encoding the members of such complexes is present inside the phage particle on which the protein is displayed. Thus, standard techniques in the field of phage display and molecular biology can be used to characterise the interacting binding partners.

In embodiments of the invention involving immobilization and wherein both the first and the second phage display libraries are bispecific phage libraries, preferred methods comprise the additional step of:

(d) separating non complexed members of the first library or second library, as appropriate, depending on the components remaining in the reaction mixture (i.e. members which have not become bound to or formed complexes with other library members) from first library members which have become bound to second library members (i.e. have formed library 1-library 2 complexes). In embodiments where the first phage display library is immobilized onto a solid phase then this additional separation step involves the separation of non complexed members of the first library. On the other hand, in embodiments where the second phage display library is immobilized onto a solid phase then this additional separation step involves the separation of non complexed members of the second library.

Such an additional separation step can further aid the manipulation or analysis of the interacting binding partners (library 1-library 2 complexes) by providing a more simple mixture of components, i.e. a clearer enrichment of interacting binding partners. Thus, after such a separation step the reaction mixture should contain only members of the bispecific phage display libraries in which complexes have formed between members of bispecific library 1 and members of bispecific library 2 (i.e. library 1-library 2 complexes).

A preferred method of carrying out the additional separation step (d) comprises:

(i) eluting both the non-complexed library members (of the first library or second library, as appropriate, depending on the components remaining in the reaction mixture), and the library 1-library 2 complexes from the solid phase, i.e. to elute all the library members from the solid phase;

(ii) immobilizing library 1-library 2 complexes onto a second solid phase by way of a tag (either tag 1 or tag 2) which is present in the library 1-library 2 complexes but is not present on the non-complexed library members;

(iii) separating said solid phase from the other components of the reaction mixture.

The tag used for the immobilization of step (ii) will be a different tag from that used in the initial immobilization step. Thus, in embodiments of the invention when initially the first phage display library is immobilized onto a solid phase by way of tag 1, then the immobilization of step (ii) will be carried out by way of tag 2. On the other hand, in embodiments of the invention where initially the second phage display library is immobilized onto a solid phase by way of tag 2, then the immobilization of step (ii) will be carried out by way of tag 1.

Such an additional immobilization step (d) (ii) has the effect that only phages with the tag not used in the initial immobilization step will be captured, i.e. only the library 1-library 2 phage complexes will be captured.

Such a separation step (d) (iii) has the effect of separating library 1-library 2 complexes (i.e. separating members of the second library which have become bound to members of the first library, i.e. separating interacting binding partners) from non-complexed (non-bound) library members, i.e. only library 1-library 2 complexes are isolated as phage dimers.

Said elution step (i) can be carried out by any suitable method, generally depending on the type of tag used for immobilization. The specific elution conditions for each particular tag are well known and documented in the art. For example, if a His tag is used than phages can be eluted from the solid phase by for example adding an excess of imidazole (e.g. 250 mM), or lowering pH. In the case of antigen peptide tags (or other protein tags) as described elsewhere herein, elution can be effected by, for example, using alkaline TEA treatment as described elsewhere herein, or any other treatment which breaks non-covalent bonds, followed by neutralization to allow the interacting binding partners to refold and bind each other. In the case of biotin tags, generally, the library constructs containing such tags are engineered to contain some kind of site for cleavage, e.g. a protease site or a restriction enzyme site, or a cleavable S—S linker which can be opened with Dithiotreitol (DTT). TEA might also be used. A cleavage site such as those described above can be used with any type of tag in order to enable or facilitate elution.

In preferred methods of the invention in which the library 1-library 2 complexes are subjected to an additional immobilization step by way of a different tag (i.e. the method is a two step purification method), it is further preferred that the library 1-library 2 complexes (i.e. the interacting binding partners) are eluted from the second solid phase before any subsequent analysis or manipulation methods are carried out. Said elution from the second solid phase can take place by any suitable means as described above for step (i).

Alternatively, it is also preferred that if the second immobilisation step is via a HIS-tag on one of the phage populations, then after first removing the first phage population which is not complexed (i.e. not bound to another phage; meaning phage-phage associated) using e.g. washing steps, the next steps could involve a simultaneous detachment of phage 1-phage 2 complexes in TEA while maintaining one of the phage libraries still immobilised on immobilized metal affinity chromatography (IMAC) beads in the presence of TEA. (TEA provides a high pH (~pH 10) which increases the binding strength of $His_6$ in IMAC). This facilitates a separation of the different phage libraries for further downstream characterisation, improved phage infectivity, or assaying.

After elution step (i) the reaction mixture will contain a mixture of non-complexed library members and library 1-library 2 complexes. Only the complexes will have a different tag (i.e. a tag not used in the initial immobilization step) available for immobilization. This tag can then be used to immobilize the complexes onto a second solid phase and allow the removal of non-complexed library members, e.g. by washing the solid phase.

In all embodiments of the invention it is preferred that the library 1-library 2 complexes (i.e. the interacting binding partners), are detached from each other, i.e. the phage-phage complexes are broken and the phage dimers are separated into single phage particles, before any subsequent analysis or manipulation methods are carried out.

Appropriate methods for detaching phage-phage complexes, i.e. library 1-library 2 complexes are described elsewhere herein. A preferred method is TEA treatment and an especially preferred method is treatment with a protease, most preferably trypsin. This protease/trypsin elution strategy will work with all full length pIII fusions irrespective of if they are produced with hyperphage or not (as for using the pSEX81 phage system). However, if the pIII fusions are made with deleted pIII this method is not preferred unless a trypsin cleavable site is incorporated to improve on detachment. Alternatively, a complete removal of the pIII fusion protein is also possible if the phages are re-amplified in bacteria (Løset et al. Biotechniques 44(4), 551-553 (2008)). The separation of the phage-phage complexes is preferred as it allows more ready analysis of the individual interacting binding partners encoded within the phage particles, e.g. by PCR amplification and analysis. In addition, the detaching of phage-phage complexes and the formation of single phage particles, makes it easier for the phages to reinfect bacteria cells, which is generally an important step for further manipulation and analysis of the interacting binding partners and is required if a further round of panning is to be carried out.

Thus the libraries to be screened in accordance with the present invention are in the form of phage display libraries. One or more of such libraries and preferably two or more or all of such libraries are bispecific phage display libraries in that more than one, preferably two, of the different types of coat proteins of the phage, display exogenous or heterologous molecules in the context of the same virus particle. Thus, exogenous molecules (preferably in the form of fusion proteins) are displayed on the surface of the phage particles at different positions (e.g. as fusions to more than one type of coat protein). In accordance with the invention, in such bispecific phage particles, a library member is displayed at a first position on the phage (e.g. as a fusion protein with one type of phage coat protein) and a tag is displayed at a second position on the phage (e.g. as a fusion with a different type of phage coat protein). The library members will generally be different from phage particle to phage particle, thereby providing the diversity of the library.

In some embodiments of the invention however a "standard" or "normal" phage display library can be used in conjunction with a bispecific phage display library. In such "standard" or "normal" phage display libraries the exogenous or heterologous molecules are displayed on one type (a single type) of coat protein, i.e. the molecules are displayed at one position (a first position) on the phage (e.g. as a fusion protein with one type of phage coat protein). In such embodiments a library member is displayed at such a first position on these phage particles. Again, the library members will generally be different from phage particle to phage particle, thereby providing the diversity of the library.

The methods of the invention involve the screening of at least two phage display libraries which are sometimes referred to herein as "first phage display library", "first bispecific phage display library", "bispecific library 1", "phage library 1", "second phage display library", "second bispecific phage display library", "bispecific library 2", "phage library 2", etc. Each of these libraries display different populations/libraries of candidate binding partners (herein also referred to as "first library"/"library 1", "second library"/"library 2", etc) at one (a first) position on the phage particles (i.e. in association with one type of phage coat protein). Where bispecific libraries are concerned, in addition, a tag molecule (herein also referred to as "first tag"/"tag 1", "second tag"/"tag 2", etc.) is displayed at another (second) position on the phage particles (i.e. in association with a different type of phage coat protein).

The library molecules and tags can be displayed at any appropriate position on the phage particles and are thus generally displayed in association with any of the five structural coat proteins of the phage, i.e. any of pIII, pVI, pVII, pVIII, and pIX. Preferred positions for display are pIII and/or pVII.

In bispecific phage display libraries, it is generally preferred that the tag molecules are displayed at opposite ends of the phage to the library molecules. Thus, preferred combinations of positions for display are pVII or pIX with pIII or pVI, e.g. pVII with pIII, pVII with pVI, pIX with pIII, or pIX with pVI, and any of these combinations may be used. Preferred combinations are pIII and pIX, or pIII and pVII, especially pIII and pVII. In addition, however, either the library molecules or the tag molecules may be displayed at the pVIII position on the phage particles. Preferred combinations are pVIII with pIII or pVIII with pVII. In addition, display at three or more positions is also possible. For example, a preferred combination of positions would be pIII, pVII and pVIII. In such phage particles, two or more different types of tags could be displayed at different positions in conjunction with a library displayed at a further position. Alternatively, two or more different libraries could be displayed at different positions in conjunction with a tag displayed at a further position.

In all the embodiments of the invention the library molecules or tags are preferably displayed at the given positions on the phage particles as fusion proteins with the relevant phage coat protein.

In preferred embodiments of the invention the library molecules are displayed at the pIII position on the phage particles, preferably as a pIII fusion protein.

In other preferred embodiments of the invention the tag molecules are displayed at the pVII position on the phage particles, preferably as a pVII fusion protein.

In most preferred embodiments the library molecules are displayed at the pIII position on the phage particles and the tag molecules are displayed at the pVII position on the phage particles.

In other embodiments of the invention the library molecules are displayed at the pVII position, preferably as a pVII fusion protein and/or the tag molecules are displayed at the pIII position, preferably as a pIII fusion protein.

The term "fusion protein" as used herein refers to an exogenous or heterologous peptide functionally fused to a coat protein, or fragment thereof, of a phage.

The term "exogenous" or "heterologous" molecule, e.g. protein or peptide molecule, as used herein refers to a molecule, e.g. a protein or a peptide, not originally part of the particular phage coat protein to which it is functionally fused or otherwise associated.

In all the fusion proteins described herein the exogenous molecule can be fused to the phage protein at any appropriate location in the phage protein as long as this location allows the exogenous molecule to be displayed at the appropriate position on the phage particle in a functional form (a functional fusion), i.e. able to act as a binding partner or a tag molecule as appropriate. It is also preferable that infectivity and viability of phage particles are not affected by the presence of the exogenous molecule. Thus, the exogenous molecules may be fused to the phage protein at or near either the C-terminus or the N-terminus of the phage protein or at some location within the phage protein, e.g. between functional domains. Appropriate locations in phage proteins for display of exogenous molecules are discussed in the art and any of these may be used. Equally, the skilled person could incorporate the exogenous molecules at a different position and readily test whether functional display still occurred at the appropriate position on the phage.

In preferred embodiments of the invention the exogenous molecules are positioned at or near, and preferably at, the N-terminus of the phage proteins, for example, in the case of the pIII phage protein, at or near, and preferably at, the N1 domain of the pIII phage protein. It is not necessary for the exogenous molecules to be fused directly to the phage proteins, for example, an indirect fusion can be employed, e.g. via a linker sequence, e.g. a linker amino acid sequence.

In addition, although the use of full length (or essentially full length) structural phage proteins is generally preferred for the fusion proteins described herein, fragments can equally be used providing that the use of such fragments still allows functional display of the exogenous molecule at the appropriate position on the phage surface. Examples of appropriate fragments are well known and described in the art, e.g. the use of the C-terminal fragments of pIII.

In addition, the fusion proteins of the invention (or the nucleic acid molecules encoding said fusion proteins) may or may not comprise a signal peptide (or a sequence encoding a signal peptide), e.g. an N-terminal signal peptide, which is located or attached N-terminally to the fusion proteins. In preferred embodiments where pIII phage proteins are used then a signal peptide, more preferably an N-terminal signal peptide, is present in the pIII fusion proteins (or at least in the nucleic acid molecules encoding said pIII fusion proteins). However, in preferred embodiments where pVII phage proteins are used then a signal peptide, e.g. a N-terminal signal peptide, is preferably not present in the pVII fusion proteins (or in the nucleic acid molecules encoding said pVII fusion proteins). Thus, in preferred embodiments of the invention the pVII protein or fusion protein does not contain a signal peptide at the N-terminal end (i.e. does not comprise an N-terminal signal peptide).

Such preferred pVII proteins and other preferred pVII fusion proteins for use in the methods of the invention are described in more detail elsewhere herein.

Thus, described herein for use in the methods of the present invention is a pVII fusion protein originating from a filamentous phage, said fusion protein does not comprise an N-terminal signal sequence and thus is a direct fusion to an exogenous peptide.

Another aspect described herein for use in the methods of the present invention relates to nucleic acids encoding the fusion proteins.

Another aspect described herein for use in the methods of the present invention relates to filamentous phages comprising the fusion proteins.

Another aspect described herein for use in the methods of the present invention relates to a library of such filamentous phages.

Another aspect described herein for use in the methods of the present invention relates to a phage display system comprising a phagemid and a helper phage, wherein the helper phage comprises a nucleic acid encoding the pVII fusion proteins described herein.

Another aspect described herein for use in the methods of the present invention relates to a phage display system comprising a phagemid and a helper phage, wherein the phagemid comprises a nucleic acid encoding the pVII fusion proteins described herein.

Another aspect described herein for use in the methods of the present invention relates to a kit comprising a phage display system comprising a phagemid and a helper phage, wherein the helper phage comprises a nucleic acid encoding the pVII fusion proteins described herein. In alternative kits the phagemid comprises a nucleic acid encoding the pVII fusion proteins described herein.

Libraries

The term "library" as used herein refers to a collection of different molecules, in particular a collection of different proteins or proteinaceous molecules. Appropriate first and second libraries of molecules to be used in the methods of the invention and displayed on the surface of the phage particles can be any population of molecules which give rise to potential interacting binding partners. The libraries are generally made up of proteins or any other proteinaceous molecules which can be encoded within the phage genome and be expressed on the surface of the phage.

The proteins or proteinaceous molecules expressed by the libraries used in the methods of the invention can be of any appropriate length providing that said length is sufficient to enable the molecule to act (or potentially act) as an interacting binding partner, e.g. as a binding partner, for a ligand. Thus, said proteins may be short peptides e.g. linear peptides, which are for example of the order of 5-50 or 7-30 amino acids in length, or longer peptides or polypeptides which may be folded or comprise folded domains rather than being linear. Thus, the proteins expressed by the libraries may be encoded for by whole genes or fragments thereof, e.g. the nucleic acids encoding the library members may be a cDNA or mRNA library or fragments thereof, for example generated from a particular cell or species or disease type or may be a genomic DNA library or fragments thereof.

Preferred libraries express protein or proteinaceous binding partners which are candidate ligands, receptors, enzymes, substrates, antigens, antibodies, etc., or fragments thereof.

Thus, first and second libraries can for example be selected from the group consisting of general protein or peptide libraries, synthetic, random or recombinant protein or peptide libraries, libraries from a particular cell, species or disease type, cell surface proteins or peptides, e.g. cell surface antigens, antibody libraries, receptor libraries, antigen libraries and ligand libraries.

Any appropriate combination of first and second libraries can be used. Preferred first and second libraries are antibody libraries and antigen libraries. Other preferred combinations of first and second libraries are ligand and receptor or substrate and enzyme. Alternatively, the first and second libraries can both be antibody libraries. In particular, such embodiments can be used to select or identify anti-idiotypic antibodies from a second library which bind to antibodies of the first library. For example, a relatively small panel of candidate antibodies, e.g. candidate therapeutic antibodies, can form the first library and the methods of the invention can be used to screen a larger second antibody library (e.g. a large scFv library) to select, preferably in one step, anti-idiotypic antibodies against at least one and preferably all the candidate antibodies. Such anti-idiotypic antibodies are valuable tools. For example, they can be used to characterize the candidate antibodies both in vitro and in vivo (e.g. in animal models such as mouse models), can be used to measure the amount of candidate antibody present in a sample, and also have the potential to act as antagonists to the candidate antibodies both in vivo and in vitro.

Thus, preferred libraries for use herein are antibody libraries. Said antibody libraries may express antibodies in any appropriate form and may comprise whole antibody molecules or antibody fragments such single chain antibodies (e.g. scFv), Fab, Fv, Fab'2, diabodies, bispecific antibodies, minibodies, heavy chains or light chains, triabodies, tetrabodies, cameloid antibodies, single domain antibodies, etc. A preferred format of antibody fragments are scFv fragments.

The antibody molecules or fragments may be of any Ig isotype, such as IgG, IgM or IgA and so forth, and the expression libraries may comprise antibodies of one or more of these subtypes. Many antibody libraries are known and described in the art and any of these, or a newly derived library, may be screened using the methods of the invention.

Other preferred libraries are libraries produced from disease associated entities, e.g. disease associated cells or cell lines, for example cancer cells or cell lines, or lymphocytes (e.g. peripheral blood lymphocytes) obtained from a diseased patient, or libraries produced from pathological agents such as viruses or bacteria. A particularly preferred library is a tumour cell library (e.g. a cDNA library) or a viral cell library (e.g. a cDNA library) to enable candidate binding partners to tumour or viral associated proteins to be identified.

Although the methods of the invention can conveniently be used to screen two phage display libraries against each other, they can equally be used to screen more than two libraries against each other, i.e. at least two libraries against each other, particularly in scenarios where some of the libraries are closely related. For example, in a preferred embodiment where libraries are prepared from patients, e.g. cancer patients, it would be advantageous to prepare libraries of molecules from each patient, e.g. antibody libraries, and then to simultaneously screen all these libraries against another library comprising candidate binding partners, e.g. an antigen library or a cDNA library prepared from a cell (e.g. a cancer cell) or virus associated with the disease the patients are suffering from. The libraries can readily be engineered in order that the origin of any selected interacting binding partner can be ascertained, e.g. the constructs of the different libraries can be engineered with different tags or markers. Thus, once particular interacting binding partners have been identified or selected by the methods of the present invention they can still be analysed, even if multiple libraries have been screened against each other.

The size and complexity of the libraries to be used in the methods of the present invention may be varied. For example, the methods of the invention can be used to screen libraries with up to 500 000 different members, or libraries with $1\times10^6$, $1\times10^8$ or more members. Typical phage display libraries have $1\times10^8$ to $1\times10^{13}$ members, and such libraries can be screened using the methods of the invention. Indeed, such libraries are preferred, although the methods can clearly also be used for screening much smaller libraries, e.g. libraries with 1000 to 50,000, 50 to 1000, or 100 to 500, or 10 to 100, or 5 to 100 members. The size and complexity of the first and second libraries used in the methods of the invention can be the same or different.

When libraries of molecules are referred to herein, the term can be used to refer to such a library at the nucleic acid or protein level, i.e. before or after expression of the encoded proteins has taken place. Clearly however, such expression libraries must be present at the protein level in order for the selection of interacting binding partners to take place. Thus, in order for the contacting step (b) to successfully occur, the libraries have to be present at the protein level (although initially they may be present at the nucleic acid level).

Methods for constructing the libraries for use in the present invention and nucleic acids encoding them are well known and described in the art and any known expression library or newly developed or constructed expression library can be used in this regard. For example such libraries may be comprised of naturally occurring peptides or proteins or fragments thereof or may be wholly or partially random or synthetic. For example, in the case of antibody libraries, the libraries may be derived by cloning nucleic acids from a naive population of lymphocytes from a healthy donor or from an enriched population of lymphocytes, e.g. lymphocytes derived from a patient which has been exposed to antigen or immunized with a vaccine (e.g. as described in WO03/095491 of Affitech AS), or for example from tumour cells, or from lymphocyte populations which have been enriched by panning on particular antigens. Indeed, any antibody library known and described in the art may be used.

The libraries and in particular the antibody libraries may be derived from any appropriate source, preferably from a mammalian source, more preferably a human source. Chimeric expression libraries or humanized expression libraries may also be used. The libraries may also be created by choosing a naturally occurring scaffold and including randomized sequences at appropriate places. Alternatively, the scaffold may be based on one or more consensus sequences derived from a variety of naturally occurring frameworks.

Generally, the techniques used to prepare constructs allowing display of the libraries and tags in conjunction with the selected phage coat proteins will be based on known genetic engineering techniques. In this regard, nucleic acid sequences encoding the library members which are to be displayed and which will generally vary between different members of the phage libraries, thereby providing the library diversity, are incorporated into expression vectors appropriate for the phage display system to be used. Appropriate tags can also be incorporated into such constructs.

Once the appropriate library constructs have been obtained at the nucleic acid level, these can then be expressed in an appropriate phage display system for use in the methods of the present invention. Appropriate conditions and methods of phage display are well known and described in the art.

Appropriate expression vectors for use in phage display are well known and described in the art. In the methods of the present invention either phage or phagemid vectors or combinations of both may be used. For example, in preferred embodiments of the invention, a phagemid construct is used to encode one of the types of exogenous molecules (either library or tag), preferably as a pIII fusion protein, and a helper phage construct is used to encode the other type of exogeneous molecules (either library or tag, as appropriate depending on the phagemid construct), preferably as a pVII fusion protein. In such embodiments it is preferred that the library members are displayed as a pIII fusion protein and the tags are displayed as a pVII fusion proteins, although other combinations can be used, as described elsewhere herein. In embodiments of the invention where the libraries are antibody libraries, an appropriate design of phage or phagemid vector to enable the expression of antibodies or antibody fragments in the desired format would be well within the normal practice of a person skilled in the art.

Once generated the nucleic acid molecules encoding different library members (i.e. encoding the library molecules which vary between the library members) can also be further diversified using standard techniques, for example by mutation involving the addition, deletion and/or substitution of one or more nucleotides in a controlled (e.g. site directed mutagenesis) or random manner, or by domain swapping, cassette mutagenesis, chain shuffling etc. Synthetic nucleotides may be used in the generation of the diverse nucleic acid sequences. Thus, all or part of the nucleic acids encoding the expression peptides can be synthesized chemically or be derived from various organisms or cell types.

The phage display constructs may optionally additionally contain other appropriate components, for example origins of replication, inducible or non-inducible promoters for initiating transcription, enhancers, termination sequences, antibiotic resistance genes and markers, signal sequences, linkers, protease sites, general tags or reporter molecules, restriction sites to enable cloning and other manipulations, primer binding sites to enable amplification of the constructs by e.g. PCR, or other desirable sequence elements, for example, DNA sequences to allow the discrimination between different libraries by e.g. PCR. Appropriate sources and positioning of such additional components within the phage display constructs so that they perform their desired function would be well within the normal practice of a skilled person in the art.

Tags

The inclusion of tags in the phage display library constructs for use in the present invention is important and such tags can be used to enable or to mediate, either directly or indirectly, the binding of library members to a solid phase in the immobilization step(s) of the methods of the invention, or can be tags that can be labelled with fluorescent antibodies for FACS sorting. Thus, such tags can be used to purify library members or complexes. Such tags can also be used to facilitate, mediate or enable detection of library members with which they are associated.

Any appropriate tag may be used in this regard providing it can enable or mediate the binding of the library members/phage particles to a solid phase or to allow the library members/phage particles to be detected in FACS, e.g. by way of a fluorescently labelled antibody. However, conveniently such tags (e.g. appropriate first tags (tag 1), second tags (tag 2), etc.) are affinity tags/molecules which can enable or mediate binding to a solid phase by binding to a partner affinity molecule or a predetermined target which is present on or provided by the solid phase, for example said partner or target immobilized directly or indirectly onto the solid phase, or which allow the library members/phage particles to be labelled with fluorescent labelled antibodies against the specific tag. The affinity tag or molecule may e.g. bind to a predetermined antibody. Pairs of affinity tags or molecules and partner affinity molecules or predetermined targets are well known to the skilled person and any of these can be used in the methods of the invention. Exemplary tags may be His tags, e.g. $HIS_6$ (hexahistidin) tags (which can for example be immobilized by binding to a Nickel surface provided by a solid phase), biotin tags (which can for example be captured by binding to streptavidin or avidin or avidin-like molecules on a solid phase), or antigen peptide tags such as c-myc, FLAG, HA (haemaglutinin), HAT or V5 tags which may be recognized and thereby immobilized by an appropriate antibody present on a solid phase. Antigen peptide tags are also preferred for use in embodiments of the invention when FACS techniques are used, as these tags readily allow for labelling by using fluorescently labelled antibodies against the specific tag. Further examples of tags which may be used are an antibody or fragment thereof, T cell receptor or fragment thereof, MHC class I and II, Ankyrin, IgNAR or fragment thereof, fibronectin or fragment thereof, Z domain of protein A, CTLA4 or fragment thereof, ImmE7, GFP and other gene-encoded biological fluorophores.

Preferred tags are protein tags or peptide tags which can readily be incorporated into the phage display constructs of the invention, e.g. using standard recombinant and cloning techniques.

Appropriate tags may directly mediate the interaction with a partner molecule or target molecule on a solid phase. However, equally, one or more intermediate molecules may be involved. For example, the tag could act as a substrate or a binding partner for such an intermediate molecule. Some of the preferred biotin tags of the invention are examples of this.

Biotin tags are preferred for use in the present invention. Appropriate biotin tags for use in the methods of the present invention would be well known to a skilled person. Biotin tags for use in the methods of the present invention may comprise biotin molecules per se, e.g. biotin molecules which are attached, e.g. via chemical conjugation, to the library members, or may comprise moieties, e.g. peptides, which can act as substrates for biotinylation reactions and thereby become attached to biotin molecules. Such biotinylation reactions to result in the biotinylation of the phage particles can take place in vitro using biotin-protein ligase (EC 6.3.4.15), which is an enzyme that activates biotin to form biotinyl 5' adenylate and transfers the biotin to biotin-accepting proteins, or in vivo, for example in host cells, e.g. bacterial cells, in which the libraries are used.

For example, a preferred biotin tag for use in the present invention is AviTag™ (MSGLNDIFEAQKIEWHE, SEQ ID NO:4), which is a commercially available tag from Avidity LLC, Aurora, Colo., USA which becomes biotinylated in vitro or in vivo by biotin ligase. For in vivo biotinylation of the phage particles, the biotin ligase enzyme, BirA, is found endogenously in all *E. coli*, and this endogenous enzyme can be used for biotinylation of e.g. an AviTag™. Alternatively, the biotin ligase can be provided to host cells, e.g. bacterial host cells such as *E. coli*, by way of a plasmid encoding an appropriate gene which can trigger the biotinylation, for example encoding the BirA gene. Appropriate *E. coli* strains are well known in the art and commercially available, e.g. the AVB101 strain from Avidity LLC. Alternatively, in vivo biotinylation could be carried out using an appropriate modified bacterial host strain with an appropriate biotinylation inducing gene, such as the BirA gene, stably integrated into the chromosome of the bacteria, e.g. *E coli* MC1061-derived AVB100 strain (Avidity, Colo., USA). A preferred example of such a strain is the F-positive *E coli* AVB100FmkII strain as described elsewhere herein. In this strain overexpression of the BirA protein is accomplished by induction with L-arabinose.

An especially preferred tag is a prokaryotic codon optimized version of AviTag, a preferred example of which is described elsewhere herein and has the sequence defined in FIG. 2B or SEQ ID NO:4.

Another example of a preferred biotin tag is Strep-tag, which is also commercially available from IBA GmbH, Göttingen, Germany, and which is capable of binding to the biotin binding pocket of streptavidin. Preferably, the Strep-tag comprises the 8 amino acid sequence Trp-Ser-His-Pro-Gln-Phe-Glu-Lys (SEQ ID NO:51). Any other protein or peptide tags which are capable of binding to streptavidin or avidin could equally be used.

As mentioned above, FLAG tags are also preferred tags for use in the methods of the present invention. Such tags are octapeptide tags and comprise the sequence DYKDDDDK (e.g. SEQ ID NO:9) as reviewed by Einhauer & Jungbauer, J. Biochem. Biophys. Methods 49,455-465, 2001. Appropriate FLAG tags are well known and described in the art (e.g. internal, processed N-terminal, unprocessed N-terminal, or C-terminal) and any of these may be used. In addition, antibodies which can recognise the various FLAG tags and can thus be used as partner molecules or target molecules therefor are also well described in the art, e.g. M1, M2 and M5 antibodies. A preferred FLAG tag for use in the present invention is an unprocessed N-terminal FLAG tag. An especially preferred tag is a prokaryotic codon optimized version of the FLAG tag, a preferred example of which is described elsewhere herein, e.g. in FIG. 2C.

A feature of using an unprocessed N-terminal FLAG tag is that it has its formyl-Met residue intact and hence allows for the Ca2+ dependent interaction with the anti-FLAG MAb M1. The phage particles can thus be bound (that is immobilized) on M1 and liberated merely by chelating the cation by e.g EDTA, hence offering a very mild elution with no extreme pH that denatures the heterologous fusion(s). By using the M1 antibody this also means that the system can be used with other FLAG fusions present (internal, processed N-terminal, or C-terminal) without interference as these are not recognized by M1, or by simply keeping the [Ca2+] low.

Thus, a preferred anti-FLAG antibody for use in the present invention is M1 which is commercially available e.g. from Sigma.

As mentioned above, HIS (histidine) tags and in particular $HIS_6$ (hexahistidine) tags (HHHHHH—e.g. SEQ ID NO: 12) are preferred tags for use in the methods of the present invention. Appropriate HIS tags comprising HHHHHH residues, e.g. SEQ ID NO: 12 are well known and described in the art and any of these may be used. An especially preferred HIS tag is a prokaryotic codon optimized version of a HIS tag, a preferred example of which is described elsewhere herein, see e.g. FIG. 2D. Appropriate partner affinity molecules or targets for use with HIS tags comprise metal ions (e.g. nickel or cobalt) to which the polyhistidine tag binds with micromolar affinity.

In contrast with the extremely strong immobilization mediated by a biotin-avidin, biotin-streptavidin interaction, a HIS tag allows for milder elution using e.g. imidazole or a slightly acidic pH. The HIS tag has the further advantage that it is compatible with all available IMAC (immobilized metal affinity chromatography) matrixes. Since the HIS-tag is active in binding to metals at high pH it can most conveniently be used together with TEA elution (pH ~10) which combines the detachment of phage-phage interactions (via their library interaction member pairs) but maintain the HIS-tag association in IMAC column/bead.

The tags for use in the methods of the invention are typically general tags which are present in all the library constructs of the relevant library, e.g. in all the constructs of the first bispecific phage display library (tag 1) or in all the constructs of the second phage display library (tag 2), etc., i.e. each of the members of these libraries have the same tag, and can be used to capture the library members onto a solid phase or to detect or separate the phage particles using FACS techniques. In certain embodiments of the invention the first tag (tag 1) and the second tag (tag 2) are the same. However, in preferred embodiments the first tag (tag 1) and the second tag (tag 2) are different. Such tags or markers can, if desired, be used to detect the presence of library members.

The steps of the methods described herein can be carried out in any appropriate order. Thus, although the specific order set out herein is generally preferred, some of the steps can be reordered. A particular example of this is that the immobilization step (if one is carried out) in which the first or second phage display library is initially immobilized on a solid phase, i.e. the first immobilization step, can be carried out before or after the contacting step (b).

Immobilization

The initial immobilization step is generally carried out to enable more easy manipulation of the assay components and to enable the isolation, separation, removal or purification of the library 1-library 2 complexes from other components of the reaction mixture. Such isolation, separation, etc., can be carried out by any appropriate method, for example, by separating or isolating the solid phase from the reaction mixture and/or carrying out one or more steps of washing the solid phase.

Appropriate solid phases for use in the methods of the present invention are well known and described in the art and it is well within the normal practice of a skilled person to select the most appropriate solid phases for use in the methods of the invention. However, preferred solid phases to which the library members become attached are particulate (for example beads, e.g. polymeric beads). Non-magnetic or labelled particles can be used. For example, if the beads or particles are labelled with a fluorescent tag, they can be separated by flow cytometry. More preferred particles are magnetic or magnetizable (e.g. magnetic beads or particles, e.g. polymeric beads carrying superparamagnetic particles). Suitable magnetic beads are available commercially from Dyno Specialty Polymers AS of Lillestrøm, Norway and Dynal Biotech ASA. Particular examples of magnetic beads which can be used in the methods described herein are the M-450, M-270 or M-280 beads from Dynal Biotech ASA, Norway. Particulate solid phases, e.g. beads, are particularly preferred as they facilitate easy manipulation and washing. Alternative solid phases are non-particulate, e.g. a planar surface such as a plate, a dish or a filter. The surface may be made of any appropriate material which is suitable for immobilization of phages via tag molecules, e.g. glass, plastic or a filter material such as nylon, nitrocellulose, etc. A preferred example would be a planar surface, most preferably a filter such a nitrocellulose filter, coated with an anti-tag antibody.

Members of the first (or second) phage display library are immobilized or captured onto a solid phase by way of the first tag (or second) which is incorporated into all members of said first or second phage library, as appropriate. Thus, immobilization is facilitated by the interaction of the tag molecule with the solid phase. Said interaction can be direct or indirect, e.g. via an intermediate molecule or moiety. A preferred method of immobilization involves the interaction of a capture molecule (e.g. a partner affinity molecule or predetermined target molecule as described elsewhere herein) on the solid phase with the first (or second) tag associated with the members of the first (or second) phage display library.

As described above, the interaction between a capture molecule on the solid phase and the first (or second) tag associated with the members of the first (or second) phage display library is conveniently based on an affinity interaction, although any other appropriate reaction may be used. For example, the members of the phage display library can be engineered to express one component of the affinity interaction (in the form of tag 1 or tag 2) and the other component (e.g. the partner affinity molecule or predetermined target molecule) can be attached to the solid phase by any appropriate means which would be well known to a person skilled in the art depending on the molecules in question. Preferred examples of such affinity interactions are antibody-antigen interactions, streptavidin/avidin-biotin interactions, His tag-nickel interactions etc.

Streptavidin or avidin coated supports can readily be generated for use in the present invention and indeed some are commercially available. For example, streptavidin or avidin coated beads are commercially available and these can be used to capture or immobilize the phage display library members via the presence of a biotin molecule in or associated with the library member. Alternatively the phage display library members may be engineered to express a tag which is recognized by an affinity partner that facilitates binding to the solid phase. Examples of appropriate tags are c-myc, FLAG, HA, HAT or V5 (or other antigen peptide tags) which can be recognized by appropriate antibodies, or His tags, e.g. $His_6$ tags which can be recognized by metal ions, for example $Ni^{2+}$, $Zn^{2+}$ or cobalt ions, which can in turn facilitate capture and immobilization to the solid phase. Appropriate metal ion matrices (e.g. on beads (including magnetic beads) or agarose) are well known to the skilled person and are commercially available, e.g. from QIAGEN GmbH, Hilden, Germany.

Where antibodies are used to facilitate immobilization or capture, these can be attached to the solid phase either directly or indirectly, e.g. via an appropriate secondary or tertiary antibody such as an anti IgG antibody.

Immobilization or capture can be effected in any appropriate way depending on the reagents used. Thus, the antibodies or other capture molecules may be attached to the solid phase, which is then brought into contact with the first (or second) phage display library or a mixture containing library member complexes obtained by allowing contact between the first and second phage display libraries before immobilization takes place. Alternatively, the antibodies or other capture molecules may be allowed to bind to the library members of the first (or second) phage display libraries or a mixture of the first and second phage display libraries before the antibodies or other capture molecules are bound to the solid phase (e.g. via a secondary antibody) to facilitate immobilization or capture.

Appropriate immobilization or capture conditions in terms of temperature and time can readily be determined by a person skilled in the art. However, exemplary conditions may comprise incubation for 15 minutes to 4 hours, e.g. 1 hour, at 4° C. to 37° C., e.g. at room temperature (depending on the stability of the library members), preferably with gentle rocking, mixing or rotation. The amount of solid phase to include, or the ratio of solid phase to library members to include, in order to facilitate immobilization of the relevant phage display library can be readily determined by a person skilled in the art.

Contacting

The step of contacting (or incubating) said first bispecific phage display library with a second phage display library can be carried out in any appropriate way under conditions such that appropriate binding partners in the first phage display library can interact with or bind to appropriate binding partners which are present in the second phage display library. Such conditions will generally vary depending on the nature of the library members, i.e. the nature of the interacting binding partners. However, appropriate conditions to facilitate binding can be readily determined by a person skilled in the art. Such a “contacting” or “incubation” step will generally occur in an appropriate solution or aqueous medium, e.g in PBS (phosphate buffered saline).

Exemplary “contacting” conditions may comprise incubation for 15 minutes to 4 hours, e.g. one hour, at 4°-37° C., e.g. at room temperature. However, these may be varied as appropriate depending on the nature of the interacting binding partners, etc. The mixture of the first and second libraries may optionally and preferably be subjected to gentle rocking, mixing or rotation. In addition, other appropriate reagents such as blocking agents to reduce non specific binding may be added. For example 1-4% BSA or other suitable blocking agent (e.g. milk) may be used. It will be appreciated however that the contacting conditions can be varied and adapted by a skilled person depending on the aim of the screening method. For example, if the incubation temperature is, for example, room temperature or 37° C., this may increase the possibility of identifying binders which are stable under these conditions, e.g. in the case of incubation at 37° C., are stable under conditions found in the human body. Such a property might be extremely advantageous if one or both of the binding partners was a candidate to be used in some sort of therapeutic application, e.g. an antibody. Again such adaptations to the conditions are within the ambit of the skilled person.

Separation

Once the contacting step (b) has been carried out then the phage-phage complexes can be separated from other components of the reaction mixture by suitable methods. One such suitable method is by way of one or more steps in which the phage-phage complexes are attached or immobilized onto a solid phase. The solid phase is then separated from the other components of the reaction mixture thereby separating members of the second library which have become bound to members of the first library from certain other components of the reaction mixture. Alternatively, as described elsewhere herein, different fluorescent labeled anti-Tag detecting antibodies can be added to the phage-phage complexes and the phage-phage complexes can be isolated using FACS. The double labeled phage complexes can be sorted using two different fluorescent labels which can be gated and correlated with the phage size corresponding to the double phage complex. To improve on the effectiveness of FACS sorting, one of the anti-tag antibodies can be attached to a non-magnetic bead, or fluorescent bead, in order to increase the size of the phage-phage complex and thereby aid the separation of the phage-phage complexes from unbound phage by both increasing the size differential and sorting on two fluorescent labels.

Said separation step can refer to a physical separation (e.g. on beads or FACS) or removal of the solid phase from the reaction mixture, or can refer to a step in which the solid phase is subjected to one or more washing steps in order to remove the other components of the reaction mixture. In embodiments where physical separation or removal of the solid phase is carried out then preferably the solid phase is also subjected to one or more washing steps.

The washing steps may be carried out in any appropriate way depending on the nature of the solid phase and the interacting binding partners attached thereto. Appropriate methods of washing particulate solid phases are well known to a person skilled in the art. For example, if the solid phase is particulate, then conveniently said washes take place by centrifuging the particles under conditions such that they form a pellet, removing the supernatant, and then resuspending the particles in an appropriate aqueous medium (for example the same medium as the contacting step was carried out in). The stringency of the washes (or indeed the contacting step) can be modified by adding appropriate reagents well known to a person skilled in the art, e.g. Tween, in order to e.g. decrease background or unspecific binding. Such steps of pelleting and resuspension would constitute one wash and any appropriate number of washes could be carried out. If however, the solid phase was magnetic, then the wash steps could conveniently be carried out by applying a magnetic field to the vessel in which the contacting step had been carried out, removing the supernatant and resuspending the solid phase in an appropriate aqueous medium. Again such steps of magnetic separation and resuspension would constitute one washing step and any appropriate number of washes could be carried out. If the solid support is non-particulate, e.g. is a planar surface such as a plate, a dish or a filter, etc., then again appropriate methods of washing such solid phases are well known to a person skilled in the art.

As well as the above described optional washing steps, it should be noted that one or more washing steps can also be carried out at any other appropriate stage in the screening method. For example, one or more steps of washing the solid phases, might also be carried out after any immobilization step which is carried out, e.g. in order to remove phage display library members which have not become bound to the solid phase. Indeed, such washing steps are preferred. Also, one or more washing steps may be carried out on the solid phases at other appropriate times during the course of the method, e.g. to remove non bound entities. How many wash steps to include can readily be determined by a person skilled in the art.

Steps (a) to (c) or (a) to (d) of the method of the invention can be regarded as constituting one round of panning (selection) for interacting binding partners. Although after the separation step (c) or (d) in the first round of panning, the interacting binding partners can be subjected to further analysis, generally however, in order to obtain a suitably enriched population of candidate binding partners to enable a productive and time effective further analysis, one or more further panning (selection) rounds will generally be carried out (i.e. the method steps will be repeated one or more times). Such multiple rounds of panning will generally have the advantage of enriching the selected complexes for true (bona fide) interacting binding partners and also amplifying the number of the different interacting binding partners present.

In general, to allow further rounds of panning to be carried out, between panning rounds it is advisable that the complexes formed between the library 1 and library 2 members are disrupted or broken, i.e. that the phage dimers are separated into single phage particles. It is also advisable to disrupt any remaining interactions with any solid phases which are present, i.e. to detach or elute all library members from solid phases. Such disruption of the complexes and/or detachment or elution from the solid phase, can be carried out using any appropriate reagent which can disrupt protein structure or otherwise disrupt library-library or library-solid phase binding interactions, for example using a protease enzyme such as trypsin (e.g. tryptic elution, Loset et al., 2008) or using an agent which disrupts non-covalent bonds such as TEA under alkaline conditions.

Alkaline TEA treatment or elution is milder. However, once the single phage particles are placed under neutralisation conditions, which will generally take place once the phage particles are placed in standard buffers for further manipulation (e.g. Tris pH8 or PBS) then the interacting binding partners are likely to refold and may rebind each other again. This might have an impact on infectivity of bacteria or may lead to a biased amplification of phages. However, if one of the libraries is tagged with HIS-tag, this can with advantage be used in combination with TEA to separate the different phage libraries. TEA having a pH at ~10 detaches the phage-phage interactions but increases the reactivity of His by deprotonating the imidazole group. This increases the metal affinity of the imidazoles towards $Zn2+$, $Ni2+$ etc. If one of the libraries is carrying HIS-tags these first members can be separated from the second library members by the means of IMAC. A more severe treatment such as trypsin or any other protease treatment which will irreversibly disrupt or destroy the interaction between the binding partners, e.g. by destroying the non-phage proteins (i.e. the interacting binding partners) is preferred and should give rise to an increased number of true interacting binding partners being selected. It should be borne in mind that even though the interacting binding partners displayed on the surface of the phage particles are disrupted by this treatment, the genetic material encoding the binding partners is still present within the phage particles and the binding partner can thus be displayed on the phage surface again in subsequent panning rounds. Moreover, the phage particles are still capable of infection.

For each round of selection (with an ideal separation of libraries before infection of the bacteria), the enrichment will increase. However if the different libraries are very diverse it may require several panning round to enrich for interacting binding pairs. For example, if one library has a diversity of $1:10^6$ (1 unique member per $10^6$ non members) and the other likewise has a diversity of $1:10^6$, the pooled complexity of interacting libraries will be $1:10^{12}$. This may require up to 10-15 steps of successive panning rounds in order to detect enrichment.

It is possible to perform several rounds of enrichment of specific binders. To this end, the phage particles eluted after one round of enrichment are amplified in *E. coli*. This is done by infecting said *E. coli* with said phages followed by production of new phage particles. If the phage particles are generated with the help of phagemid DNA vectors not coding for the full phage genome, additional infection with helper phage is needed for generation of new phage particles (packaging). The exact protocol needed for amplification and packaging of eluted phages will depend on the vectors used, and there is an abundance of protocols described in the literature, e.g McCafferty et al (Antibody Engineering, IRL Press, Oxford, 1996) and in McCafferty, J. & Johnsson, K. S., pp 79; (Phage Display of Peptides and Proteins; academic Press, San Diegio; Kay, Winter & McCafferty (eds); 1996).

Of special interest in many embodiments might be the use of Hyperphage as helper phage. Hyperphage is a helperphage which have the advantage that they can infect F+ *E. coli* with high efficiency due to their wild-type pIII phenotype. They lack their functional pIII gene so that the phagemid encoded antibody-fusions to pIII is the only source of pIII. This increases the active concentration of pIII-antibody fusion proteins with increased antibody displayed on phage and improved avidity towards the antigen by up to 400-fold (Rondot S., et al. Nat. Biotechnol. 19, 75-78; 2001).

The phage particles generated by the packaging process are purified and used as starting material for the next round of selection.

A skilled person can readily determine the number of rounds of panning, if any, which are required or desired. Once the appropriate number of panning (selection) rounds have been carried out then the selected interacting binding partners can be subjected to further analysis or uses. By isolating the different phage populations completely before re-infection and allowing a separate packaging of the different phage libraries, the enrichment may proceed faster and with a better outcome than just re-infecting with the mixed phage-phage complex library. First of all if the phage-phage interaction is very strong it may inhibit re-infectivity of phages for *E. coli*. Possibly only weak interacting pairs will be able to re-infect. In addition, if both interacting phage populations are packed together in the same bacteria, it is very likely that interacting library members will be complexed already during this packaging process and may results in less efficient display. By using a Hyperphage more copies of the fused library member, e.g. the pIII-library member, will be displayed on the phage. In this respect even weakly interacting library members will affect infectivity and it is more important to separate phage populations.

It is also advisable that such a disruption of the interacting binding partners with each other and/or a disruption of the phage library members interacting with any remaining solid phases, i.e. a detachment from solid phases, takes place before any downstream analysis or manipulation of the members of the interacting binding partners is carried out. Thus, treatments such as those described above can be carried out after which phages can, if desired, be amplified by infecting and growth in bacteria.

Analysis

Once one or more sets of interacting binding partners have been selected or isolated in accordance with the methods of the invention, these can be subjected to further analysis. This may involve a further processing or analysis of either or both of the interacting binding partners, e.g. the members of the library which have bound to the ligands or the ligands themselves. Thus, the methods of the invention allow for the screening and identification of both novel binding partners and novel ligands, e.g. novel cell surface molecules or proteins such as novel antigens, at both the polypeptide and the nucleic acid level.

Said further analysis or uses generally require the candidate binding partners to be detached, removed, isolated or eluted from the other member of the interacting binding partner and preferably the candidate binding partners are expressed or produced in isolation from each other. Thus, the methods of the present invention may comprise a further optional step wherein said interacting binding partners are detached, removed, eluted, or preferably isolated from each other, or are expressed or produced in isolation from each other. For example in the case of phage display libraries such as those used in the present invention, said further analysis generally involves the isolation of individual interacting binding partners by infection of bacteria as amplification step, isolating the phage or phagemid DNA and cloning the DNA sequence encoding the candidate binding partner contained in said phage or phagemid DNA into a suitable expression vector. Such an infection step can also allow the amplification of the individual interacting binding partners. Alternatively, individual interacting binding partners can be amplified at this stage by other appropriate methods, for example by PCR of the nucleic acids encoding said individual interacting binding partners or the transformation of said nucleic acid into an appropriate host cell (in the context of a suitable expression vector).

Once the DNA encoding the binding partners are cloned in a suitable expression vector, the DNA encoding the binding partner can be sequenced or the protein can be expressed in a soluble form and subjected to appropriate binding studies to further characterize the candidates at the protein level. Appropriate binding studies will depend on the nature of the binding partners, and include, but are not limited to ELISA, filter screening assays, FACS or immunofluorescence assays, BiaCore affinity measurements or other methods to quantify binding constants, staining tissue slides or cells and other immunohistochemistry methods. Such methods are well established in the literature and one or more of them may be used to analyse the interacting binding partners.

As mentioned above, appropriate methods for analyzing the individual interacting binding partners would be well known to a person skilled in the art. One preferred method will be to use PCR, for example to amplify and analyse nucleic acids encoding individual interacting binding partners.

If there is a need to detect different phage populations it is also possible to insert PCR tags into the phage genome so that mutual enrichment of binding pairs can be detected with the help of Polymerase chain reaction (PCR). In general, also the different sizes of amplified DNA of two interacting members from different libraries may reveal a binding pair.

Each of the library members may most conveniently be detected in a single PCR reaction. However, also by double fluorescent labelling of tags via labelled antibodies binding to each respective tag in FACS machine it is possible to detect phage complexes.

Each of the different libraries can be recloned into an expression vector and individual library monoclonal members (without its phage molecule) can be expressed in *E. coli*. By using standard gridding methods known to the person skilled in the art (e.g. filter screening analysis) it is possible to use arrays of 300-30,000 individual library member clones on a surface and express protein from them. The use of the second enriched bispecific polyclonal phage library (still encoded as a fusion to phage protein) can be used as a detection molecule to find its complementary library binding partner on the filter. The tag of this phage library can be used as detection tag. After detecting the position for interaction of the clone array, the corresponding monoclonal phage can be isolated from the filter and amplified by used of PCR or phage display.

Another method is to express individual monoclonal library members in solution (e.g in 384-well plates), then couple library members onto magnetic beads (via an expression tag) in each well and add polyclonal phage preparation to each of the wells. The beads can be washed to remove unwanted phage preparations and positive phages can be detected with ELISA or PCR.

The expressed proteins can also be gridded onto a suitable surface, leading to protein arrays well known to people skilled in the art.

Another method to label each library individually is to use dsDNA linkers with unique restriction enzymes. dsDNA can be synthesized with a specified restriction enzyme digestion sites e.g. NcoI, HindIII or NotI, having biotinylated 5' and 3' ends. By using biotin tag on the bispecific phage library members it is possible to couple them with streptavidin (in 4-5 molar excess to avoid cross-linking of phages) which binds to biotin with femtomolar affinity. This allows crosslinking of restriction digested dsDNA via biotin-streptavidin, and permits specific labelling of different phage libraries with a unique stretch of dsDNA having a specific restriction site. The restricted dsDNA linker can be treated with calf intestine phosphatase (CIP) to avoid that the restricted dsDNA is re-anneling unspecifically. Thus, each different bispecific library can now be attached to solid phase via a complementary immobilised restricted dsDNA immobilised on streptavidin beads. A selective capture of each DNA-tagged phage library can be made by on its respective beads using ligation using T4 ligase. CIP prevents self-ligation of phages, and elution can be performed with specific restriction digestion to gradually elute of specific antigen library-antibody binding pairs.

Methods of the invention can thus be used to select, identify or isolate interacting binding partners, or individual members thereof, which can then be isolated, produced or manufactured for various downstream uses. As such, binding partners identified or selected using the methods of the invention form a further aspect of the invention.

Once appropriate nucleic acid fragments encoding binding partners or ligands with particular properties have been identified, the nucleic acids encoding the polypeptides can, if desired, be subjected to affinity maturation, for example to try and identify binding partners with further improved properties. Such affinity maturation can be performed by carrying out any conventional form of mutagenesis, including but not limited to the addition, deletion and/or substitution of one or more nucleotides in a controlled (e.g. site directed mutagenesis) or random manner, error-prone PCR, domain swapping, cassette mutagenesis and chain shuffling, etc., prior to rescreening.

When one or more interacting binding partners, or individual members thereof, have been selected, identified, isolated and/or purified using the methods of the invention, these entities, or a component, fragment, variant, or derivative thereof may be manufactured and if desired formulated with at least one pharmaceutically acceptable carrier or excipient. Such manufactured molecules, or components, fragments, variants, or derivatives thereof, are also encompassed by the present invention. Alternatively, these molecules may take the form of nucleic acids encoding said protein molecules, which nucleic acids may in turn be incorporated into an appropriate expression vector and/or be contained in a suitable host cell. Thus, nucleic acid molecules encoding said binding partners or target entities, or expression vectors containing said nucleic acid molecules form further aspects of the invention.

Once a particular binding partner, or a component, fragment, variant, or derivative thereof, has been selected, identified, etc., in accordance with the present invention, the expression vector encoding the selected binding partner can readily be used (or adapted for use) to produce sufficient quantities of the molecule by expression in appropriate host cells or systems and isolating the binding molecules from the host cell or system or from the growth medium or supernatant thereof, as appropriate. Alternatively, said binding partners may be produced by other appropriate methods, e.g. by chemical synthesis of the nucleic acid encoding the binding partner and expression in a suitable host or in an in vitro transcription system.

Thus, a yet further aspect of the invention provides a method of manufacturing a binding partner comprising the steps of identifying or selecting a binding partner according to the methods of the invention as described above, manufacturing said identified binding partner, or a component, fragment, variant, or derivative thereof and optionally formulating said manufactured binding partner with at least one pharmaceutically acceptable carrier or excipient.

Said variants or derivatives of a binding partner or ligand include peptoid equivalents, molecules with a non-peptidic synthetic backbone and polypeptides related to or derived from the original identified polypeptide wherein the amino acid sequence has been modified by single or multiple amino acid substitutions, additions and/or deletions which may alternatively or additionally include the substitution with or addition of amino acids which have been chemically modified, e.g. by deglycosylation or glycosylation. Conveniently, such derivatives or variants may have at least 60, 70, 80, 90, 95 or 99% sequence identity to the original polypeptide from which they are derived.

Where the binding partner is an antibody molecule, said variants or derivatives further include the conversion of one format of antibody molecule into another format (e.g. conversion from Fab to scFv or vice versa, or the conversion between any format of antibody molecules described elsewhere herein), or the conversion of an antibody molecule to a particular class of antibody molecule (e.g. the conversion of an antibody molecule to IgG or a subclass thereof, e.g. IgG1 or IgG3, which are particularly suitable for therapeutic antibodies).

Said variants or derivatives further include the association of binding partner molecules or ligands with further functional components which may for example be useful in the downstream applications of said binding partners or ligands. For example the binding partners or ligands may be associated with components which target them to a particular site in the body, or detectable moieties useful for example in imaging or other diagnostic applications.

Clearly, the main requirement for such components, fragments, variants, or derivative binding partner molecules or ligands is that they retain their original functional activity in terms of binding ability or have improved functional activity.

The binding partner molecules (preferably antibody molecules) or ligands isolated, detected, selected, identified or manufactured using the methods of the present invention may be used in any methods where binding partners specific to a ligand (for example antibodies specific to a particular antigen) are required. Thus, the binding partners (preferably antibody molecules) or ligands can be used as molecular tools and a further aspect of the invention provides a reagent which comprises such binding partner molecules or ligand molecules as defined herein. In addition, such molecules can be used for in vivo therapeutic or prophylactic applications, in vivo or in vitro diagnostic applications, or in vitro assays. For example, such molecules can be used to monitor disease progression or to monitor therapy.

The binding partners may be used in therapeutic applications, either in the form isolated from the expression libraries or engineered or converted forms, e.g. it may be desirable to convert an scFv molecule to an IgG or to multimerize peptides.

Where the binding partners selected or identified, etc., are antibody polypeptides then these can be used for in vivo therapeutic and prophylactic applications, e.g. to confer passive immunity to particularly susceptible individuals (e.g. immunocompromised patients, small children, the fetus of pregnant women, people in endemic areas for disease, etc). For example if the antibodies are capable of neutralizing infective or disease related agents then these can be administered to an appropriate subject to combat disease. Alternatively, antibodies (or other forms of binding partner) can be attached to other therapeutically effective molecules, e.g. to cytotoxic agents (small molecule or protein), pre-toxin or other drugs and targeted to disease tissue or specific cell types, e.g. tumour cells or virus infected cells. Further therapeutic effects might be achieved by other functions engineered into the agent to be administered like the ability to activate macrophages, complement or cytotoxic T cells conferred for example after changing an scFv to an Ig, generation of bispecific molecules, e.g. linking tumour cells and killer cells.

Alternatively such antibodies (or indeed other types of polypeptide which interact with ligands associated with particular tissue or body sites, or cell types, e.g. tumour cells or virus infected cells) can be conjugated to labels, e.g. dyes, fluorescent or radioactive labels or enzymatically detectable labels, and used for in vitro or in vivo diagnosis, for example by imaging or standard immunohistochemical procedures. Other preferred uses include theranostic uses (i.e. antibodies or binding partners used in both diagnosis and therapy). In addition, such antibody molecules or other binding partners may be used in affinity chromatography procedures to isolate ligands.

In particular, antibodies to cell surface expressed proteins provide a well described starting point for the successful development of new diagnostic and therapeutic drugs. This is particularly the case in the cancer field, where the knowledge of specific cell surface markers as well as antibodies binding to them, is a clear bottleneck in drug development, and the methods of the invention can be used to identify or select both novel cell surface markers (ligands) and antibodies (binding partners). Currently, only a very limited number of cell surface expressed tumor-associated or tumor-specific epitopes are known. Thus, every new epitope of such type—and of course specific antibodies binding to them—would open new possibilities in the treatment of cancer. Possible applications span from naked whole IgG antibody products for ADCC-based therapy, over recombinant oligo-specific/oligo-valent constructs, to fusion-protein immunotoxins and radio-labeled antibody fragments for tissue-specific and targeted therapy, as well as dye- or radio-coupled antibodies for in vitro and in vivo diagnosis.

The ligands, or fragments thereof could be used as vaccines, in particular vaccines for use in the treatment for cancers and infectious diseases (depending of course on the ligand in question). The ligand may be used as target for agonists and antagonists, in form of peptides, proteins or small molecule drugs, which may for example block or induce functions like apoptosis or regulating cell growth. The ligands may also be used as a target for further screening, to identify even more molecules able to do some of the things described above. In some cases, the ligands or fragments thereof might also have an effect in itself, like competitively binding of molecules naturally binding to it.

Suitable and appropriate adaptations of the antibody molecules, if necessary for such uses, e.g. the conversion to IgG1 or IgG3 classes for therapy, the incorporation or addition of an appropriate label for imaging, etc., would be well known to a person skilled in the art.

Yet further aspects of the invention provide such isolated, detected, identified, selected or manufactured binding partners, for use in therapy or in vivo diagnosis or for use in any of the other applications mentioned above. Also covered is the use of such binding partners in the manufacture of a medicament or composition for use in therapy or in vivo diagnosis or for use in any of the other applications mentioned above. Methods of treatment of a patient comprising the administration of an appropriate dose of such a binding partner are also provided.

When said antibody molecules (or other binding partners), or ligands, are used in the above described uses and methods then these may be administered in any appropriate way. For example such antibody molecules (or other binding partners), or ligands, may be administered locally at the site where action is required or may be attached or otherwise associated with entities which will facilitate the targeting of the antibody molecules (or other binding partners), or ligands, to an appropriate location in the body.

Pharmaceutical compositions comprising the binding partners as identified or selected by the methods of the present invention, together with one or more pharmaceutically acceptable carriers or excipients form a yet further aspect of the invention.

Yet further aspects are methods of diagnosis or imaging of a patient comprising the administration of an appropriate amount of a binding partner as identified or selected by the methods of the present invention to the patient and detecting the presence, location and/or amount of the binding partner in the patient.

The binding partners identified, selected, etc., using the methods of the invention may equally be used in methods of diagnosis which are carried out in vitro, if appropriate, e.g. carried out on a tissue sample or some other kind of sample, e.g. blood, obtained or derived from a patient.

Other Steps

The methods of the present invention may involve further additional steps. For example, one or more of the libraries which are to be screened in the methods of the invention may be pre-panned to remove some non-desired library members or to reduce the complexity of the library. Said pre-panning may be a negative panning step wherein the library is contacted with one or more non-relevant entities before step (a) of the method. For example, if the method is designed to identify library members which bind to a particular type of cancer cell, pre-panning may be carried out by contacting the library members with one or more different or irrelevant cell types, e.g. a different type of tumour cell or a non-tumour cell type or "normal" cell type such as lymphocytes or endothelial cells or other cells which are not of interest. The aim of said negative pre-panning steps is to remove a proportion of the library members which will not bind the ligands of interest.

Alternatively, said pre-panning steps can be positive panning steps wherein the library is panned/contacted with the target ligand in order to enrich the library for members which bind to the target ligands and thereby reduce the complexity of the library to be screened in accordance with the methods of the present invention. For example, if the screening method is designed to identify library members which bind to a particular type of cancer cell, pre-panning may be carried out by contacting the library members with the particular target cell in order to enrich the library for members which bind. One or more pre-panning steps can be carried out on the same or different relevant or non-relevant entities.

In embodiments of the invention where positive panning is used to enrich the expression library, an appropriate number of rounds, preferably 1, 2, 3 or 4 rounds, of panning are carried out in order to enrich the expression library and to reduce the complexity of the library to be screened. Any appropriate method of panning may be used and these would be well known by a person skilled in the art.

It should be noted that throughout this description of the invention embodiments and features described in the context of one of the aspects of the present invention also apply to the other aspects of the invention.

All patent and non-patent references cited in the present application, are hereby incorporated by reference in their entirety. In particular, the contents of PCT application number, PCT/EP2008/060908 (WO09/024,591), are incorporated by reference in their entirety.

Also presented herein is a concept, in which the structural coat protein pVII of the filamentous phage virion is genetically altered such that the modified version encodes an N-terminal sequence tag. Depending on which type of tag that is fused to pVII, the virions are given the property of specific tag detection, as well as flexible purification and immobilization avenues as an inherent property of the system. The approach is directly compatible with all existing pIII and pVIII display systems whether phage genome-based or phagemid vectors are applied, including new library generation on pVII. This concept therefore offers an unprecedented expansion of the already high versatility of phage display technology.

The current report shows that the filamentous phage genome tolerates an N-terminal peptide modification, not harbouring a signal sequence, of pVII without interfering with viability and functionality of the phage. This was true for both the M13K07 (SEQ ID NO: 31), VCSM13 (SEQ ID NO: 32) and fUSE5 (SEQ ID NO: 30) genomes as well as phagemids and as the sequence and phenotypic conservation between the various phage strains are very high, This most likely applies to all filamentous phages.

One of the pVII fusions chosen was a prokaryotic codon optimized version of the AviTag, a peptide which is the most efficient BirA substrate reported to date. By combining this pVII peptide display with pIII display we show that bispecific virions are produced. This was true for the phage-genome based vector fUSE5 (SEQ ID NO: 30) and from phagemid-based display when rescued with a modified M13K07 helper phage. It is easily conceivable that this bispecific nature can be used in combination with pVIII display as well. Particularly in the case of the phagemid-derived virions, the endogenous biotinylation level was very low.

However, if high biotinylation levels are desirable, this can easily be achieved by in vitro biotinylation of these virion, as well as by the use of in vivo biotinylation through the use of the novel F-positive *E. coli* AVB100FmkII strain.

Hence, the current concept allows for the combination of avidin-biotin technology (and other capture systems) with both dominating phage display platforms (phage and phagemid) and display systems (pIII and pVIII). It allows a controlled, site specific attachment of the biotin moiety to the phage particle without interfering with the pIII and/or pVIII fusion, hence ensuring preserved functionality. The system is directly compatible with existing platforms without further modifications, only rendering the choice of use or not.

In conclusion, both genome-derived and phagemid-derived virions can tolerate the pVII modification, yielding virions with seemingly normal functionality and viability.

Phage Coat Proteins and Fusion Proteins

Described herein for use in the methods of the present invention is a pVII fusion protein originating from a filamentous phage, said fusion protein comprising a fusion of an exogenous or heterologous peptide to the N-terminus of pVII. Such a fusion protein is useful e.g. in the context of phage display.

When referring to an exogenous or heterologous peptide, what is meant is a peptide not originally part of the relevant phage coat protein, e.g. the pIII, pVII or pVIII protein, etc., which is fused with or without any linker amino acids to the N-terminal end of the phage coat protein part, e.g. the pIII, pVII or pVIII amino acid part of the fusion protein. In a preferred embodiment, in particular where pVII fusion proteins are concerned, the fusion protein does not comprise an N-terminal signal sequence. As used herein, the term "peptide" encompasses both short peptides, polypeptides, proteins and fragments thereof.

The term "pIII protein" refers to a pIII protein originating from or derived from a filamentous phage, or a pIII protein with a sequence which corresponds to the sequence of such a pIII protein. Preferred pIII proteins comprise the amino acid sequence disclosed in SEQ ID NO: 2.

In one embodiment the pIII protein comprises the amino acid sequence with a sequence identity of at least 80% to that of SEQ ID NO: 2, such as 80% identity, 81% identity, 82% identity, 83% identity, 84% identity, 85% identity, 86% identity, 87% identity, 88% identity, 89% identity, 90% identity, 91% identity, 92% identity, 93% identity, 94% identity, 95% identity, 96% identity, 97% identity, 98% identity, or 99% identity.

The term "pVIII protein" refers to a pVIII protein originating from or derived from a filamentous phage, or a pVIII protein with a sequence which corresponds to the sequence of such a pVIII protein. Preferred pVIII proteins comprise the amino acid sequence in SEQ ID NO: 3.

In an embodiment the pVIII protein comprises the amino acid sequence with a sequence identity of at least 80% to that of SEQ ID NO: 3, such as 80% identity, 81% identity, 82% identity, 83% identity, 84% identity, 85% identity, 86% identity, 87% identity, 88% identity, 89% identity, such as 90% identity, 91% identity, 92% identity, 93% identity, 94% identity, 95% identity, 96% identity, 97% identity, 98% identity, or 99% identity.

The term "pVII protein" refers to a pVII protein originating from or derived from a filamentous phage, or a pVII protein with a sequence which corresponds to the sequence of such a pVII protein. Preferred pVII proteins comprise the amino acid sequence in SEQ ID NO: 1.

In an embodiment the pVII protein comprises the amino acid with a sequence identity of at least 80% to that of SEQ ID NO: 1, such as 80% identity, 81% identity, 82% identity, 83% identity, 84% identity, 85% identity, 86% identity, 87% identity, 88% identity, 89% identity, 90% identity, 91% identity, 92% identity, 93% identity, 94% identity, 95% identity, 96% identity, 97% identity, 98% identity, or 99% identity.

The term "pVIII fusion protein" refers to a pVIII protein, or fragments thereof, fused to an exogenous peptide.

The term "pIII fusion protein" refers to a pIII protein, or fragments thereof, fused to an exogenous peptide.

The term "pVII fusion protein" refers to a pVII protein, or fragments thereof, fused to an exogenous peptide.

In another preferred embodiment, the pVII fusion protein of the invention comprises a sequence selected from the group consisting of pos. 1-33, 2-33, 3-33, 4-33 and 5-33 of SEQ ID NO:1 or a sequence with a sequence identity of at least 80%, etc., as described above, to that sequence.

SEQ ID NO:1 (MEQVADFDTIYQAMIQISVVLCFALGIIAGGQR) is the amino acid sequence of structural coat protein pVII of the filamentous phage (wild type pVII). Most preferably, the pVII fusion protein comprises positions 1-33 of SEQ ID NO:1.

Sequence Identity

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See the wesbite having an URL that begins with "www" and ends with "ncbi.nlm.nih.gov". Alternatively, sequence identity may be calculated after the sequences have been aligned e.g. by the BLAST program in the EMBL database (the wesbite having an URL that begins with "www" and ends with "ncbi.nlm.gov/cgi-bin/BLAST"). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

Folded Proteins

In a preferred embodiment, the term peptide refers exclusively to folded proteins such as antibody derived domains. The skilled addressee would recognise folded proteins could be antibodies or fragments thereof, covering Fv, scFv, Fab, single domains, Z domain of protein A (Affibody), Ankyrin or fragments thereof, T cell receptor or fragment thereof, MHC class I and II, Fibronectin or fragment thereof, Avimers, Anticalins, PDZ-domains, IgNAR or fragment thereof, CTLA4 or fragment thereof, ImmE7, Knottins, GFP and other gene-encoded biological fluorophores.

In principle, one can make a library of anything as long as it is displayed, hence at the highest level one can only separate between something that has only a non structured configuration, as compared to a ordered structure, that is a fold.

In another preferred embodiment, the term peptide refers exclusively to short peptides between 2 to 50 aa. At some length a short random coil peptide will be long enough to adopt a defined secondary or tertiary fold and hence enter the folded domain definition. Obviously this will depend on chemical composition, hence one peptide of 20 aa will still be random coil, whereas another 20 aa peptide could be folded and hence fall into the folded domain definition.

Signal Sequence

Preferably, in embodiments where a pVII fusion protein is used, the exogenous peptide is fused directly with or without any linker amino acids to the N-terminal end of the pVII sequence of the fusion protein. In yet another preferred embodiment, the pVII fusion protein does not comprise an N-terminal leader sequence.

The term "leader sequence" is used interchangeably with the terms "signal peptide" and "signal sequence", and refers to an amino acid sequence that targets the protein (of which the leader sequence is part) to the periplasmatic membrane space of gram negative bacteria. Any appropriate leader sequence can be used and examples of such sequences would be well known to a person skilled in the art. Examples of leader sequences often used are pelBss, OmpAss, TorAss (e.g. TorA7I or TorA7II), malEss, phoAss, lamBss, Blass, and DspAss, mglBss, sfmCss, tolBs, TorTss and pIIIss. Such signal sequences are known to target the complete protein to the secretory machinery of *E. coli* which is known to include at least SRP-dependent, SEC-dependent, TatABC-dependent or YidC-dependent translocation from the cytosol to the periplasmic space (Baneyx et al., 2004). Hence, the term N-terminal signal sequence refers to a signal sequence that is in the N-terminal part of the protein. Preferred signal sequences for use herein are pelB and TorA7II.

Signal sequences harbouring the property of targeting a protein (of which it is part) to the secretory machinery of *E. coli* and thereby translocate it from the cytosolic to the periplasmic compartment can be partly identified through signatures, or motifs, defined by the chemical property of their amino acid composition.

The variety of functional signal sequence existing is as of yet, however, exceeding the current knowledge in identifying them, hence current state of the art in defining a peptide as a cognate signal sequences are typically done through data mining using knowledge based data based as template by e.g. neural network or heuristic methodology. There are several such tools available to the community through open access channels as of today, such as SignalP, PPSEARCH of PROSITE (EMBL-EBI), SecretomeP, TatP.

The challenge is even higher with the class of secretory proteins, in the sense that they are exported from the cytosolic compartment, that deviate from the rules such that no signal sequence motif can be identified, but through data mining one can also here define signal sequence features or get the probability of the secretory capacity of the eukaryotic protein in question. As of yet, no such tool exist for the prokaryotic taxa.

The only method currently available that irrevocably identified a peptide as a signal sequence is therefore by experimental means to validate the property of a peptide to establish whether or not it is a real signal sequence. It is also clear that engineering may be performed in such peptides such that the given amino acid positions in the signal sequence may be altered, yet retain its function as a signal peptide, either by native functionality, or by altered functionality, such as increased transport capacity. Also deletion or addition of amino acids may be employed. Such analysis and engineering have indeed been done with the Ff pVIII signal sequence, g8pss targeting the Sec-pathway, and the TorAss targeting the Tat-pathway. Especially the results of Shen et al may serve as well-founded guide lines for engineering of functional, but altered mutants, of the pIII signal sequence and the bacterial pectate lyase signal sequence.

The functionality of a signal sequence may be further broken down into the two following properties:

1. Targeting a protein (of which it is part) to the secretory machinery of *E. coli* and thereby translocate it from the cytosolic to the periplasmic compartment and in the course of this process, being proteolytically separated from the remaining protein by specific proteases, such as Lipoprotein signal peptidase, or leader peptidases.

2. Targeting a protein (of which it is part) to the secretory machinery of *E. coli* and thereby translocate it from the cytosolic to the periplasmic compartment and after translocation still remain as a part of the protein.

Though the vast majority of signal sequences map to situation 1) given above, it is clear that these proteins may be easily engineered into situation 2). Therefore, any currently known signal sequences e.g. a mutant pelBss and other that originally belong to the situation 1), but are altered into situation 2), are still regarded as cognate signal sequences.

Moreover, it is conceivable to either alter a signal sequence of situation 1) into situation 2), or directly choose a signal sequence that map to situation 2) and then after translocation remove the signal sequence. This can be done either by endogenous proteases of the host and/or in the case of e.g. phage display, when the protein is fused to a capsid protein. One would then engineer into the proper region of the signal sequence, or the protein of which it is a part, an artificial protease site, such that a defined cleavage can be performed. One can here envision two different types of protease sites chosen:

A. The protease site does not cleave the protein of interest, only the predicted site, such as e.g. carboxypeptidase A, or 3C rhinovirus protease site in combination with antibodies or other scaffolds of interest, such as major histocompatibility complex molecules or T cell receptors. By using this approach one can envision e.g. phage display of the protein of interest by use of a signal sequence mapping to the situation 2) above and before used in selection etc, artificially remove the signal peptide to obtain functionality and homogeneity to the capsid fusion.

B. The protease site cleaves the protein of interest in addition to the engineered site, such as e.g. trypsin.

Both situations will still be regarded as signal sequence-dependent phage display.

Wild Type Complementation

Hitherto, it was believed that pVII fusions without signal sequence were nonfunctional with respect to sustaining production of phage particles (Endeman et al, 1995; Gao et al, 1999). Therefore, pVII fusion proteins with an exogenous peptide fused directly to its N-terminus had to be complemented by wt pVII protein either from a second gene on the phage genome or by donation from a helper phage.

The term wild type, sometimes written wildtype, wild-type or wt, is the typical form of an organism, strain, gene, or characteristic as it occurs in nature. Wild type refers to the most common phenotype in the natural population. Wild type also refers to the allele at each locus required to produce the wild-type phenotype. Wild type is the standard of reference for the genotype and phenotype. In biology it relates specifically to the difference between a naturally occurring organism, and one that has been deliberately mutated. Site-directed mutagenesis is a research technique that allows for the mutation of specific nucleotides in the gene sequence of a wildtype gene. Wildtype proteins are written as wt-(name of protein) e.g. a wildtype pVII protein is written wt pVII, wt-pVII or wildtype pVII.

It is shown herein that such pVII fusion proteins are indeed functional and need not necessarily be complemented by wt pVII protein.

Thus, embodiments of the present invention relate to the use of pVII fusion proteins that are functional in a phage display without complementation by wt pVII protein.

Kwasnikowski et al. reported pVII fusion proteins that did not have to be complemented by wild type pVII protein. However, the pVII fusion proteins of Kwasnikowski et al., comprised a signal peptide at the N-terminal end of the exogenous peptide. Said signal peptide was assumed to be necessary to direct the N-terminal pVII fusion protein into the periplasmic space and prevent its accumulation in the cytoplasm.

The absence of a signal peptide at the N-terminal end of the pVII fusion protein has various advantages. Signal peptides are normally proteolytically removed and this processing is often not complete which generates different N-terminal ends of the processed protein when a collection of proteins are expressed, thus introducing a random heterogeneity in the system, that may affect functionality of the proteins still harbouring the leader peptide leading to unwanted errors in the processed protein. This is prevented when no signal peptide is present.

Moreover, when a library of peptides are displayed, some of the peptides may prevent or affect proteolysis, which in turn will affect activity of the displayed protein and thus functional library diversity. Yet another surprising advantage of not including a signal peptide is that viability and functionality of the phage is not affected, as opposed to when using a signal peptide. Kwasnikowski et al., reported a reduced titer for phages with the pVII fusion protein comprising a leader sequence (signal peptide) at the N termini Exogenous Peptide In one embodiment, the exogenous peptide is an affinity tag that binds to a predetermined target. The affinity tag or molecule may e.g. bind to a predetermined antibody. Pairs of affinity tags or molecules and partner affinity molecules or predetermined targets are well-known to the skilled person.

Protein tags are peptide sequences genetically grafted onto a recombinant protein. Often these tags are removable by chemical agents or by enzymatic means, such as proteolysis or intein splicing. Tags are attached to proteins for various purposes.

Affinity tags are appended to proteins so that they can be purified from their crude biological source using an affinity technique.

A feature of using an unprocessed N-terminal FLAG tag is that it has its formyl-Met residue intact and hence allows for the Ca2+ dependent interaction with the anti-FLAG MAb M1. The virion can thus be bound (that is immobilized) on M1 and liberated merely be chelating the cation by e.g EDTA, hence offering a very mild elution with no extreme pH that denatures the heterologous fusion(s). By using the M1 antibody this also means that the system can be used with other FLAG fusions present (internal, processed N-terminal, or C-terminal) without interference as these are not recognized by M1, or by simply keeping the [Ca2+] low.

In a preferred embodiment, the exogenous peptide of the pVII fusion protein is selected from the group consisting of Avitag (SEQ ID NO:4), FLAG tag (SEQ ID NO:9), HIS tag (SEQ ID NO:12), HAT tag, HA tag, c-Myc tag, Strep tag, V5 tag, antibody or fragment thereof, T cell receptor or fragment thereof, MHC class I and II, Ankyrin, IgNAR or fragment thereof, fibronectin or fragment thereof, Z domain of protein A, CTLA4 or fragment thereof, ImmE7, GFP and other gene-encoded biological fluorophores.

SEQ ID NO:4 (MSGLNDIFEAQKIEWHE) is a substrate sequence of the *E. coli* enzyme BirA sequence that enables enzyme mediated site-specific coupling of a biotin moiety to the substrate sequence. Thus, the assets of phage display technology and avidin-biotin technology are combined. Any fusion library in which the library is not displayed on pVII may e.g. first be fractionated against a target for identification of high-affinity library members and then immobilized using biotin binding to avidin, or an avidin-like matrix by means of also including the pVII fusion on the virions. Alternatively, any fusion library in which the library is not on pVII may e.g. first be immobilized, either randomly or in a predefined array on an avidin or avidin-like matrix, in a controlled, directional manner followed by target screening such as in e.g. SEREX, by means of also including the pVII fusion on the virions. Similarly, any member of such a pIII or a pVIII fusion library may be detected, either in bulk or as single clones, before or after target interaction by use of any avidin- or avidin-like-reporter complex the term reporter herein describes e.g. enzyme, nucleic acid species or synthetic or biological fluorophore.

Essentially the same rational as outlined for the AviTag, but whereas the latter results in a close to irreversible immobilization, the HIS6 allows for mild elution using imidazole. The HIS tag is compatible with all available IMAC matrixes, In another preferred embodiment, the exogenous peptide of the pVII fusion protein is a library member. A library as used in the present context refers to a collection of different peptides. The peptides may be folded domains or short peptides of e.g. 2-50 amino acids. Such libraries are of interest because they can be used to identify new ligands binding to a given target. There are several advantages of using pVII for displaying a library as compared to libraries displayed using pIII or pVIII. pVII display contain the same assets as pIII display with respect to directionality and valence, but will not affect infectivity, a phenomenon known to occur with pIII display, which introduced uncontrolled and unwanted heterogeneity into the system upon e.g. rescue after affinity selection. Moreover, pVII display may be achieved without the need of an N-terminal leader peptide, which are prerequisites for both pIII and pVIII display. Finally, any target immobilised species in pIII display normally requires disruption (normally by competitive, or high or low pH elution) of this target-phage bond. This is e.g. known to severely hamper retrieval of high-affinity, or stable binders in pIII display. As pIII required for infection is unaltered and readily available for alternative interactions in pVII display even after phage-target interaction, this completely eliminates the need for bond disruption, e.g. acidic elution, as immobilised phages retain full infectivity and hence may be retrieved simply by infection whilst bound to target.

Nucleic Acid

Another aspect described herein for use in the methods of the present invention is a nucleic acid encoding the fusion proteins described herein. The nucleic acid may be comprised within a phage genome or within a phagemid.

The term "nucleic acid" refers to a macromolecule composed of chains of monomeric nucleotides. In biochemistry these molecules carry genetic information or form structures within cells. The most common nucleic acids are deoxyribonucleic acid (DNA) and ribonucleic acid (RNA). In addition, the term nucleic acids include artificial nucleic acids such as peptide nucleic acid (PNA), Morpholino and locked nucleic acid (LNA), as well as glycol nucleic acid (GNA) and threose nucleic acid (TNA). Each of these is distinguished from naturally-occurring DNA or RNA by changes to the backbone of the molecule.

A phagemid or phasmid is a type of cloning vector developed as a hybrid of the filamentous phage Ff and plasmids to produce a vector that can propagate as a plasmid, and also be packaged as single stranded DNA in viral particles. Similarly to a plasmid, a phagemid can be used to clone DNA fragments and be introduced into a bacterial host by a range of techniques (transformation, electroporation). However, infection of a bacterial host containing a phagemid with a 'helper' phage, for example VCSM13 or M13K07, provides the necessary viral components to enable single stranded DNA replication and packaging of the phagemid DNA into phage particles.

Filamentous Phage

Another aspect described herein for use in the methods of the present invention is a filamentous phage comprising the fusion proteins described herein. The filamentous phage may comprise a phage genome or a phagemid.

Phage, often called bacteriophage, is here meant as a virus infecting, replicating and which is secreted from bacteria. A filamentous bacteriophage, or filamentous phage, is a phage with a single stranded DNA genome (ssDNA genome) which is packaged with phage coat proteins. The secreted filamentous phage particle has phenotypically a filamentous structure.

The term "filamentous phage" as used herein encompasses both phage genome derived virions and phagemid-derived virions.

In one embodiment, the filamentous phage does not comprise a gene encoding the fusion protein, as the fusion protein may have been donated by a helper phage.

The term "helper phage" refers to a virus which helps a separate and unrelated defective virus, defined as e.g. a phagemid which in itself is not a phage genome or a functional virus, but merely a plasmid containing one or several elements derived from a phage genome, to reproduce by infecting the same host cell that is already occupied by the defective virus and providing the proteins which the defective virus is missing and needs to complete its life cycle and form virions containing the phagemid.

Preferred helper phage for use in the described screening methods or kits are described elsewhere herein and include M13K07 (Stratagene), Hyperphage (Progene), VCSM13, or a BirA helper phage which contains a tag such as AviTag™ which can be biotinylated by the Bir A gene product. Preferably the tag, e.g. the AviTag™, is fused to pVII in the helper phage. A particularly preferred example of a BirA helper phage is the AviTag™ modified VCSM13 helper phage (BirA-VCSM13) containing an AviTag™ fused to pVII, as described in Examples 1 to 4. (BirA is endogenously expressed in all *E. coli*. VCSM13 contains only the AviTag™ sequence fused to pVII providing a substrate for the BirA enzyme).

In another embodiment, the filamentous phage does comprise a nucleic acid encoding the fusion protein. The filamentous phage may comprise a phage genome or a phagemid. Particular preferred is a phage that comprises a phage genome or a phagemid comprising the nucleic acid encoding the fusion protein of the invention. In yet another embodiment, the filamentous phage of the invention further comprises a gene encoding wt pVII and/or wt pVII protein. I.e. the number of fusion proteins displayed by the filamentous phage may be adjusted by modulating the ratio of wt pVII to pVII fusion protein. Such a system may also be referred to as a 77 system or 7+7 system depending on whether the wt pVII protein is donated from a helper phage (7+7) or from a second gene on the phage genome (77).

In still another embodiment, the filamentous phage does not comprise wt pVII gene and/or wt pVII protein. I.e. the filamentous phage comprises only pVII fusion protein and no wt. pVII protein.

In a preferred embodiment, the filamentous phage for use in the methods of the present invention further comprises a pIII fusion protein or a pVIII fusion protein, most preferably a pIII fusion protein. A library may e.g. be displayed at pIII or pVIII, preferably pIII, and the pVII fusion protein may be used for affinity purification, immobilization or detection using e.g. avidin or an avidin-like matrix as described elsewhere herein. Preferably, the filamentous phage comprises pIX protein solely in wild type form.

Another aspect described herein for use in the methods of the present invention is a library of filamentous phages as described herein, said filamentous phages displaying exogenous peptides or proteins as fusions to pIII, pVII or pVIII.

A library is a collection of filamentous phages displaying peptides or proteins as part of one or more of the filamentous phage coat proteins. Such libraries can comprise two or more phages displaying different peptides or proteins. In a preferred embodiment, peptides are displayed simultaneously at pVII and either pIII or pVIII, more preferably pIII.

In another preferred embodiment, the exogenous peptide displayed at pVII is selected from the group consisting of Avitag (SEQ ID NO:4), FLAG tag (SEQ ID NO:9), HIS tag (SEQ ID NO:12), HAT tag, HA tag, c-Myc tag, Strep tag, V5 tag, antibody or fragment thereof, T cell receptor or fragment thereof, Ankyrin, IgNAR or fragment thereof, fibronectin or fragment thereof, MHC class I and II, Z domain of protein A, CTLA4 or fragment thereof, ImmE7, GFP and other biological gene-encoded fluorophores. In this embodiment, the peptides displayed at pIII or pVIII are preferably library members. In an alternative embodiment, the library members are displayed at pVII, while pIII or pVIII displays an exogenous peptide, e.g. a tag as described elsewhere herein, selected from the group consisting of an Avitag (SEQ ID NO:4), FLAG tag (SEQ ID NO:9), HIS tag (SEQ ID NO:12), HAT tag, HA tag, c-Myc tag, Strep tag, V5 tag, antibody or fragment thereof, T cell receptor or fragment thereof, MHC class I and II, Ankyrin, IgNAR or fragment thereof, fibronectin or fragment thereof, Z domain of protein A, CTLA4 or fragment thereof, ImmE7, GFP and other biological gene-encoded fluorophores.

Phage Display System

Another aspect described herein for use in the methods of the present invention is a phage display system comprising a phagemid and a helper phage, wherein the helper phage comprises a nucleic acid encoding the pVII fusion proteins as described herein.

Phage display system, phage display technique, phage display technology or simply phage display refers to a method for the discovery and study of proteinprotein, protein-peptide, and protein-DNA interactions that utilizes bacteriophage to connect proteins with the genetic information that encodes them.

Displaying protein or displayed protein refers to a protein fused to a phage coat protein that is accessible for detection or immobilisation by a ligand Another aspect described herein for use in the methods of the present invention is a phage display system comprising a phagemid and a helper phage, wherein the phagemid comprises a nucleic acid encoding the pVII fusion proteins as described herein.

Kits

Another aspect described herein for use in the methods of the present invention is a kit comprising a phage display system composed of a phagemid and a helper phage, wherein the phagemid comprises the nucleic acid encoding the pVII fusion proteins as described herein. The kit could include a phagemid with a pVII encoding gene with a multiple cloning site N-terminally in the coding region and a helper phage (e.g. M13K07, VCSM13 or other). The kit could be supplemented with protocols for infection, expression, immobilisation, selection and detection of phage clones. The kits could also be accompanied with necessary recipes for buffers and media for performing the specific assays.

A kit is here referred to a collection of reagents for generating phage particles with a single or bispecific fusion proteins either as a phage display library or as single phage particle. A kit could include phagemids, helper phages, bacterial strains and protocol with recipes for reagents and assay description. A kit can be used for the development of research, diagnostic and therapeutic reagents.

Another aspect described herein for use in the methods of the present invention is a kit comprising a phage genome-based phage display system, wherein the phage genome comprises a nucleic acid encoding the pVII fusion proteins described herein.

The kit could include a phage genome vector (M13K07, VCSM13, fUSE5 (SEQ ID NO: 30)) with a pVII encoding gene with a multiple cloning site N-terminally in the coding region. The kit could be supplemented with protocols for infection, expression, immobilisation, selection and detection of phage clones. The kits could also be accompanied with necessary recipes for buffers and media for performing the specific assays.

Another aspect described herein for use in the methods of the present invention is a kit comprising a helper phage for production of pIII fusion phagemid libraries or single pIII fusion phagemid clones with a tag as a pVII fusion. The kit could include a Helper phage (M13K07, VCSM13) with a pVII encoding gene with inserted sequence encoding a short peptide suitable for capture and/or detection purposes. The kit could be supplemented with protocols for infection, expression, immobilisation, selection and detection of phage clones. The kits could also be accompanied with necessary recipes for buffers and media for performing the specific assays.

Another aspect described herein for use in the methods of the present invention is a kit comprising a phage genome vector for generating a phage genome library for display of fusion proteins on both pIII and pVII. Such a kit could include a phage genome vector (Ff) with genes encoding both PIII and PVII with multiple cloning sites N-terminally in each of the coding regions. Alternatively the kit could contain a phage genome vector with inserted sequence N-terminally in pVII encoding a short peptide suitable for capture and/or detection and a multiple cloning site N-terminally in pIII. The kit could be supplemented with protocols for infection, expression, immobilisation, selection and detection of phage clones. The kits could also be accompanied with necessary recipes for buffers and media for performing the specific assays.

A yet further aspect of the invention is a kit comprising two bispecific phage display libraries as defined herein. Said kits thus comprise a first phage display library, wherein phages of said first phage display library are bispecific and comprise a member of a first library displayed at a first position and a first tag displayed at a second position, together with a second phage display library, wherein phages of said second phage display libary are bispecific and comprise a member of a second library displayed at a first position and a second tag displayed at a second position. Preferred bispecific libraries for inclusion in the kits are as described elsewhere herein. Solid phases could be supplied as optional components and again preferred solid phases are described elsewhere herein. The kit could be supplemented with protocols for infection, expression, immobilisation, selection and detection of phage clones. The kits could also be accompanied with necessary recipes for buffers and media for performing the specific assays.

Another aspect described herein for use in the methods of the present invention is a method comprising the steps of:

1) Providing a bispecific phage display library, wherein phages comprise a peptide displayed at a first position and an affinity-tag at a second position;

2) Selecting the phage display library against a target;

3) Immobilizing the phage display library against a capture group of the affinity-tag.

The invention will now be described in more detail in the following non-limited Examples with reference to the following Figures in which:

FIG. 1: Schematic drawing of the filamentous phage structure. The virion is built up by five structural proteins that coat a single-stranded DNA molecule. In the wild type (wt) phage there are about 2700 copies of pVIII and approximately 3-5 copies of either of the four proteins pIII, pVI, pVII and pIX, which are found at each tip of the virion. Virion size is dependent on the genome size at approx. 2.3 nucleotides per pVIII coat protein and thus the length of the particle is accommodated by an increase or decrease in the inserted copies of pVIII. Notably, the pIII and pVIII structures have been characterized by x-ray fiber diffraction, crystallography and NMR. The minor coat protein pIII contains three distinct domains separated by glycin-rich regions: N1 (binds to TolA), N2 (binds to the F pilus) and CT (integrated into the virion and is important for normal virion assembly).

Figure 2:
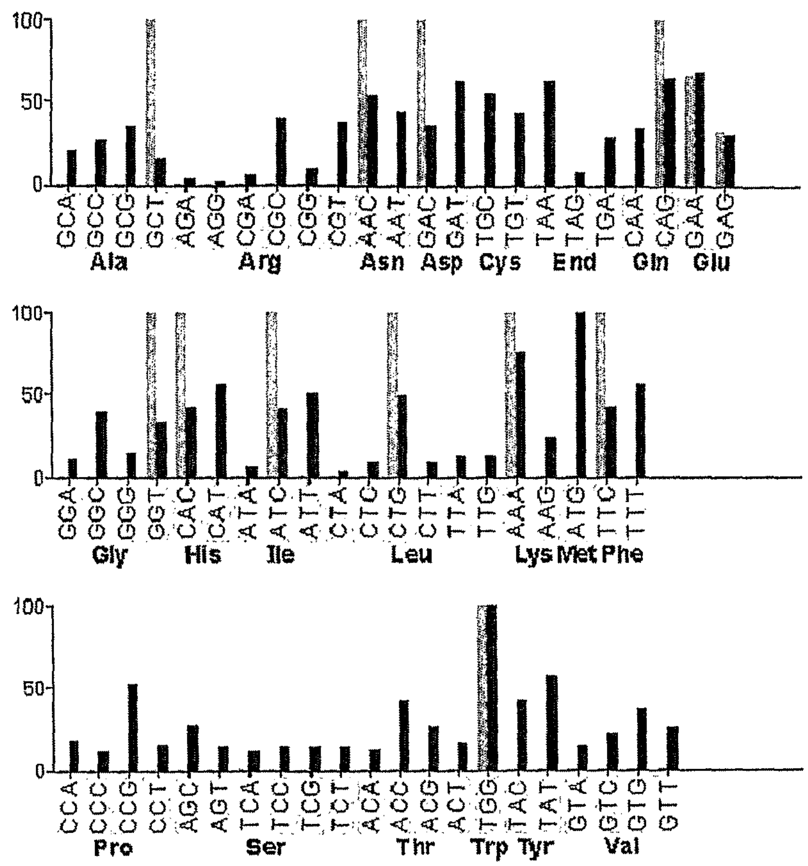

FIG. 2: *E. coli* K12 codon optimisation of AviTag™, HIS6-tag and FLAG-tag. (A) Comparison of the commercially available AviTag™ DNA sequence with the *E. coli* K12 codon usage. Red columns are the submitted sequence and black columns are the reference set. (B) Upper line shows the original AviTag™ (SEQ ID NO:44), whereas the lower line shows the modified sequence adjusted according to the result in A (SEQ ID NO:45) with the amino acid sequence (SEQ ID NO:46) below. (C) codon optimised FLAG peptide (nucleotide sequence—SEQ ID NO:47; amino acid sequence—SEQ ID NO:48). (D) codon optimised HIS6 peptide (nucleotide sequence—SEQ ID NO:49; amino acid sequence—SEQ ID NO:50).

Figure 3:
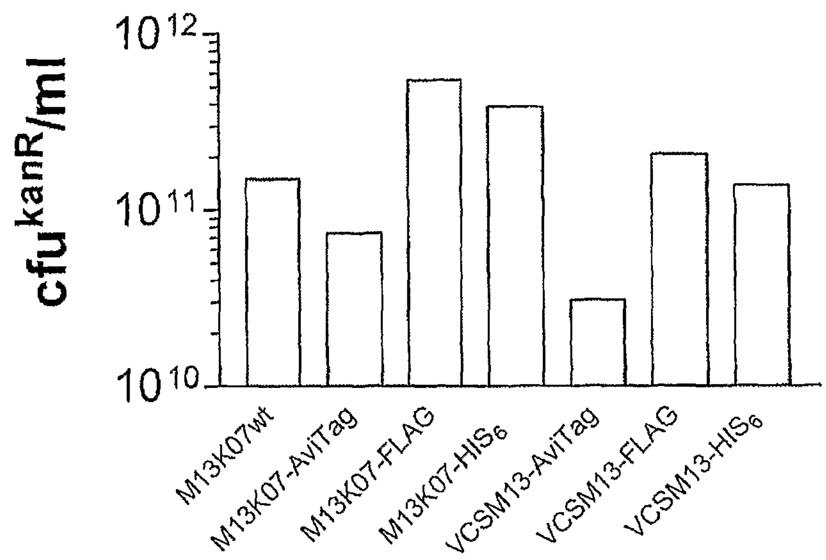

FIG. 3: Titer of modified helperphages compared to wt helperphage.

Figure 4:
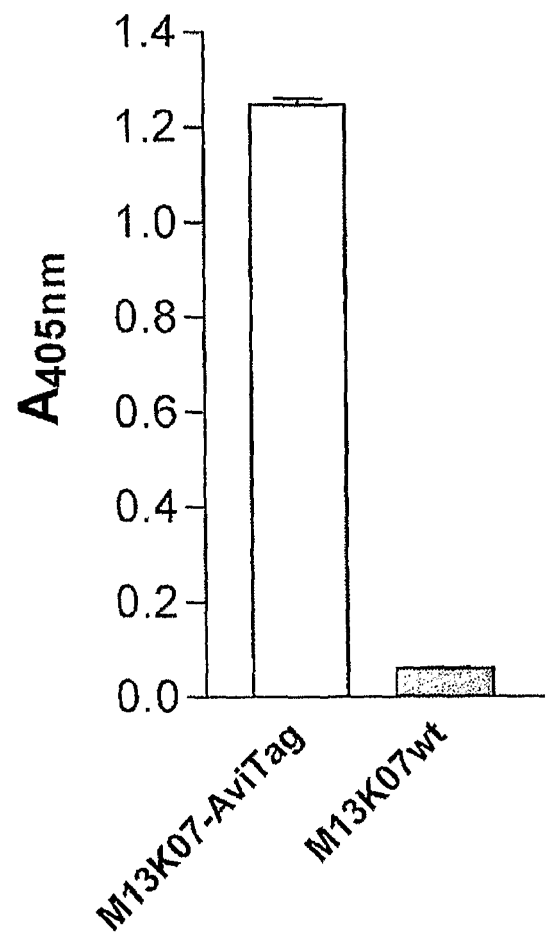

FIG. 4: ELISA analysis M13K07 AviTag-pVII. Normalised phage preparations were mixed with Streptavidin (SA) beads to absorb biotinylated virions and ELISA was performed as described in example 1.

Figure 5:
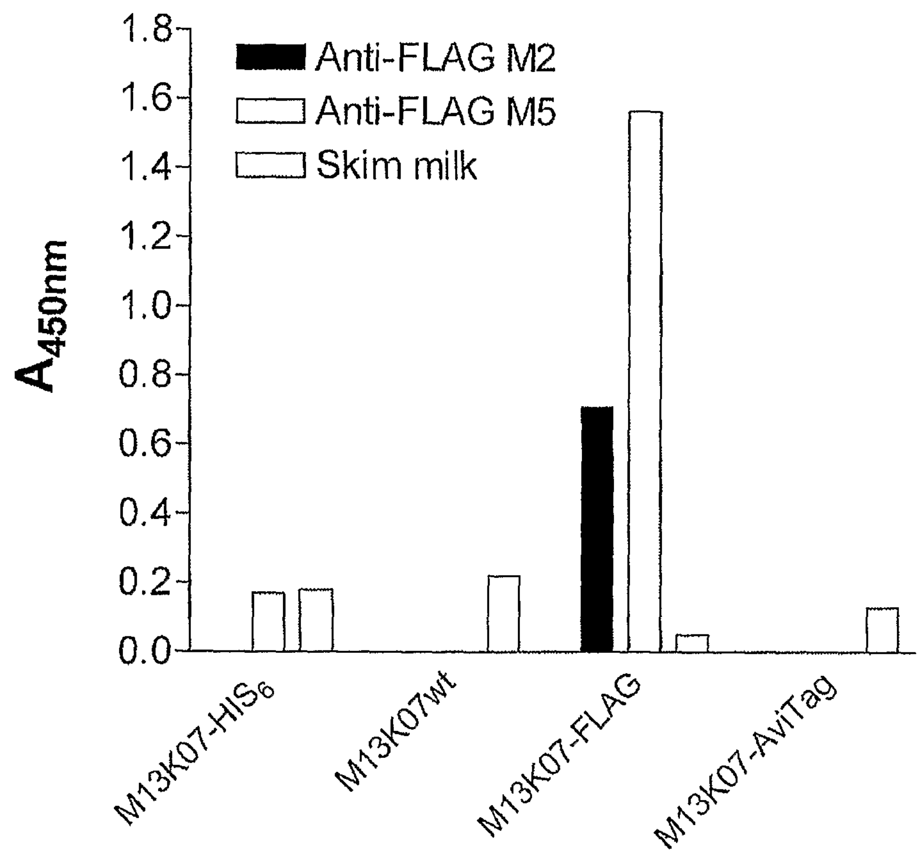

FIG. 5: ELISA analysis showing the accessibility of the FLAG-tag as a pVII fusion in M13K07. Normalised phage preparations were used in the ELISA assay. There is a specific FLAG-tag detection only of the M13K07-FLAG both for the M2 and M5 MAb. There is a stronger detection of the FLAG-tag by the M5 MAb.

Figure 6:
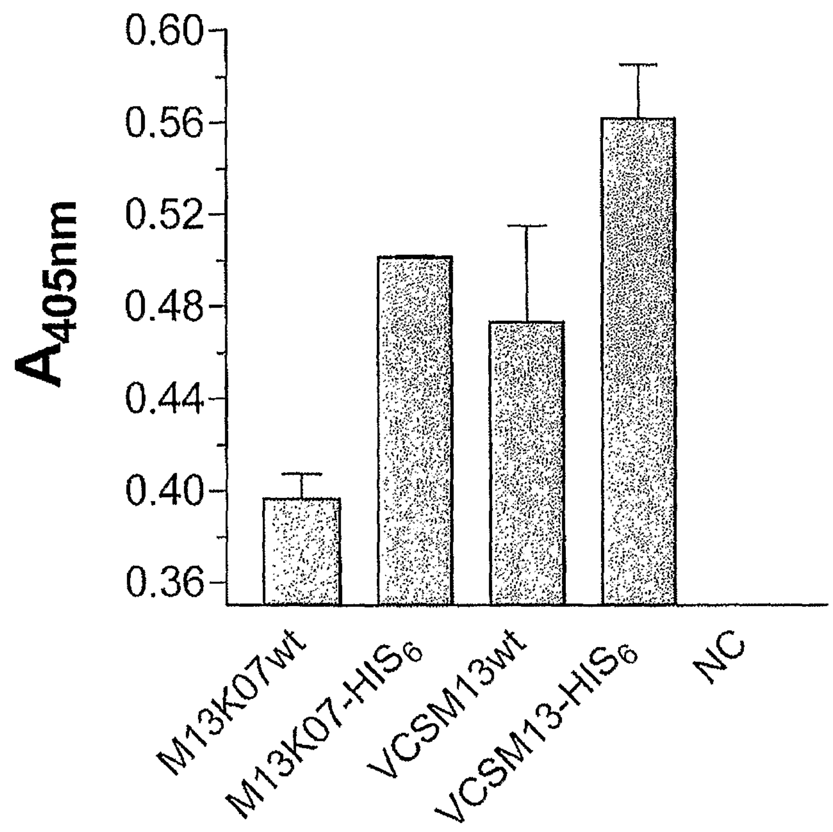

FIG. 6: Analysis showing the accessibility of HIS-tag as a pVII fusion to both M13K07 (SEQ ID NO: 31) and VCSM13 (SEQ ID NO: 32). Normalised phage preparations were mixed with Talon Dynabeads to absorb HIS6-tagged virions and ELISA was performed as described in example 1.

Figure 7:
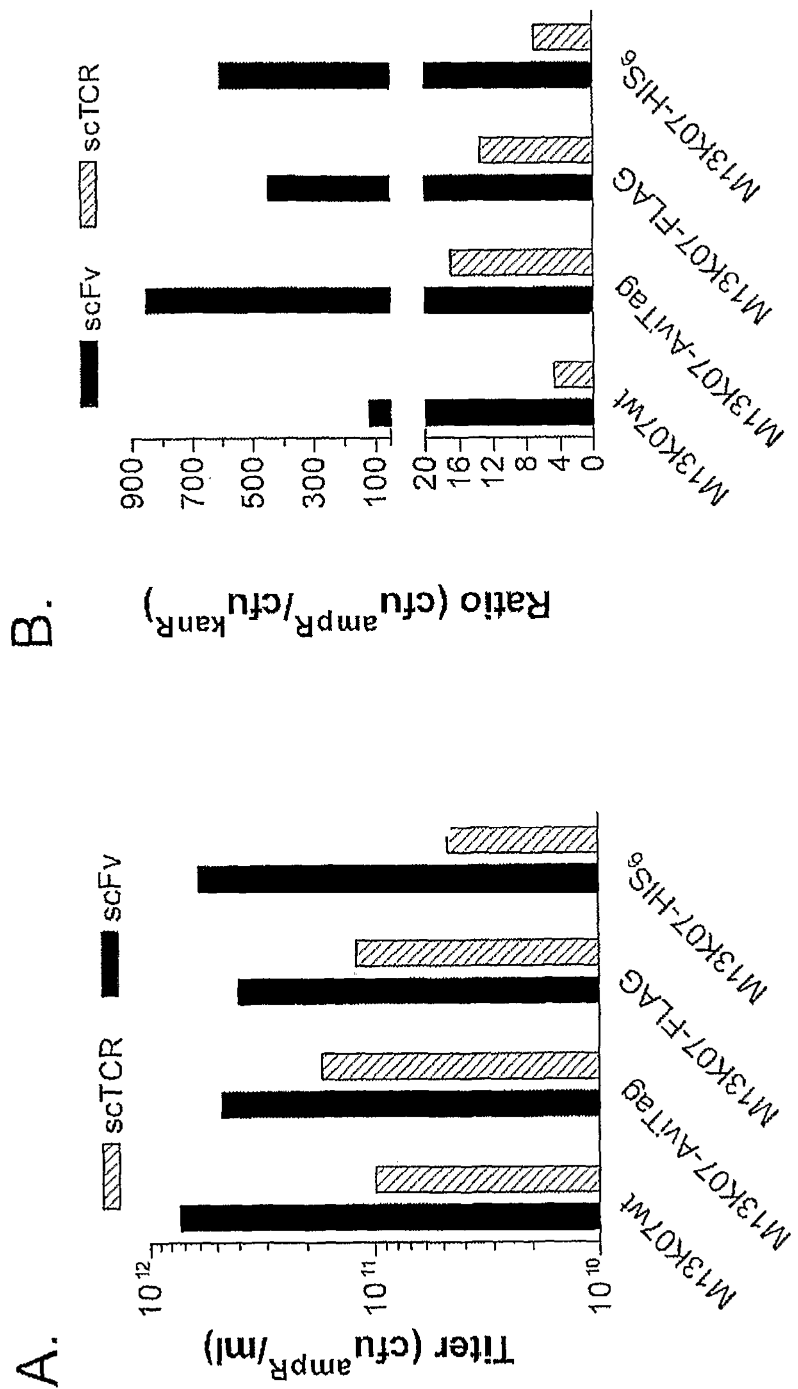

FIG. 7: (A) Phagemid titers of scTcR and scFv-pIII displayed phagemids shown as cfuampR/ml. (B). Phagemid to helper phage ratios shown as the ratio of the phagemid titer (cfuampR/ml) divided by helper phage titer (cfukanR/ml).

Figure 8:
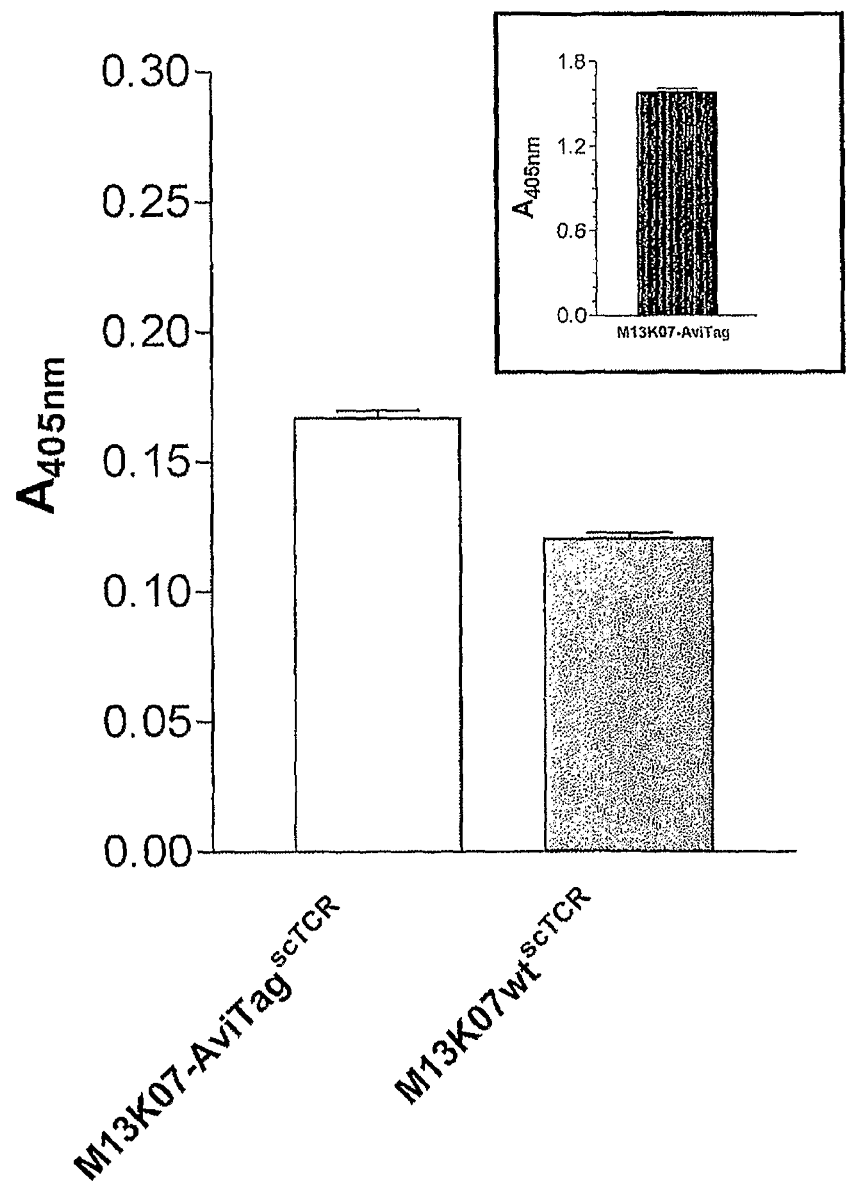

FIG. 8: ELISA analysis of scTCR phagemid AviTag showing specific accessibility of AviTag after phage rescue by streptavidin coated dynabeads. Inset show signal value of M13K07-AviTag helperphage. Normalised phage preparations were used.

Figure 9:
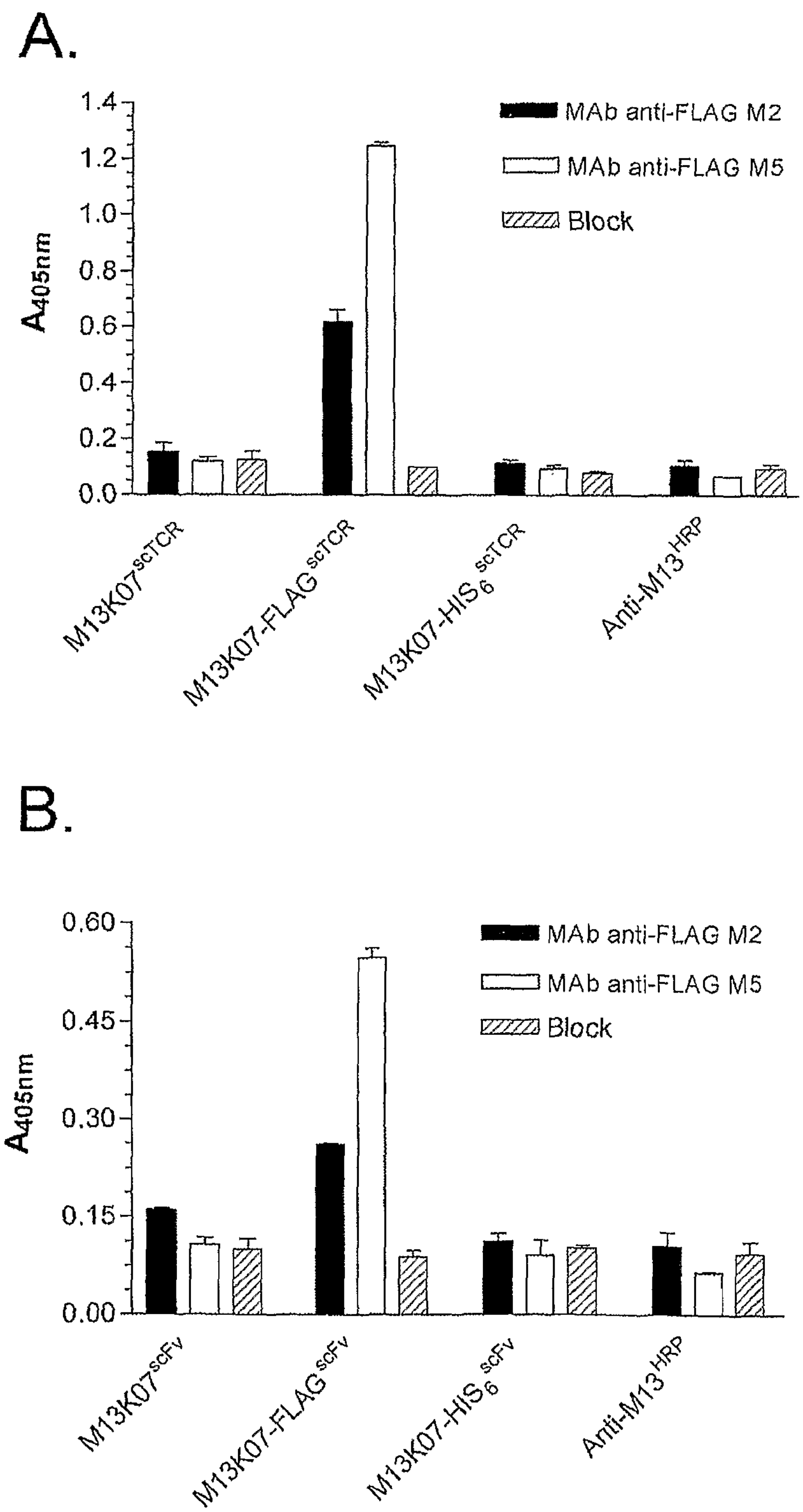

FIG. 9: ELISA analysis showing the accessibility of the FLAG-tag as a pVII fusion in two different phagemids, pFKPDNscTCR Vαβ4B2A1 (A) and pSEX-scFv anti-phOx (B) by capturing of phagemid virions by two anti FLAG antibodies, M2 and M5. Normalised phage preparations were used.

Figure 10:
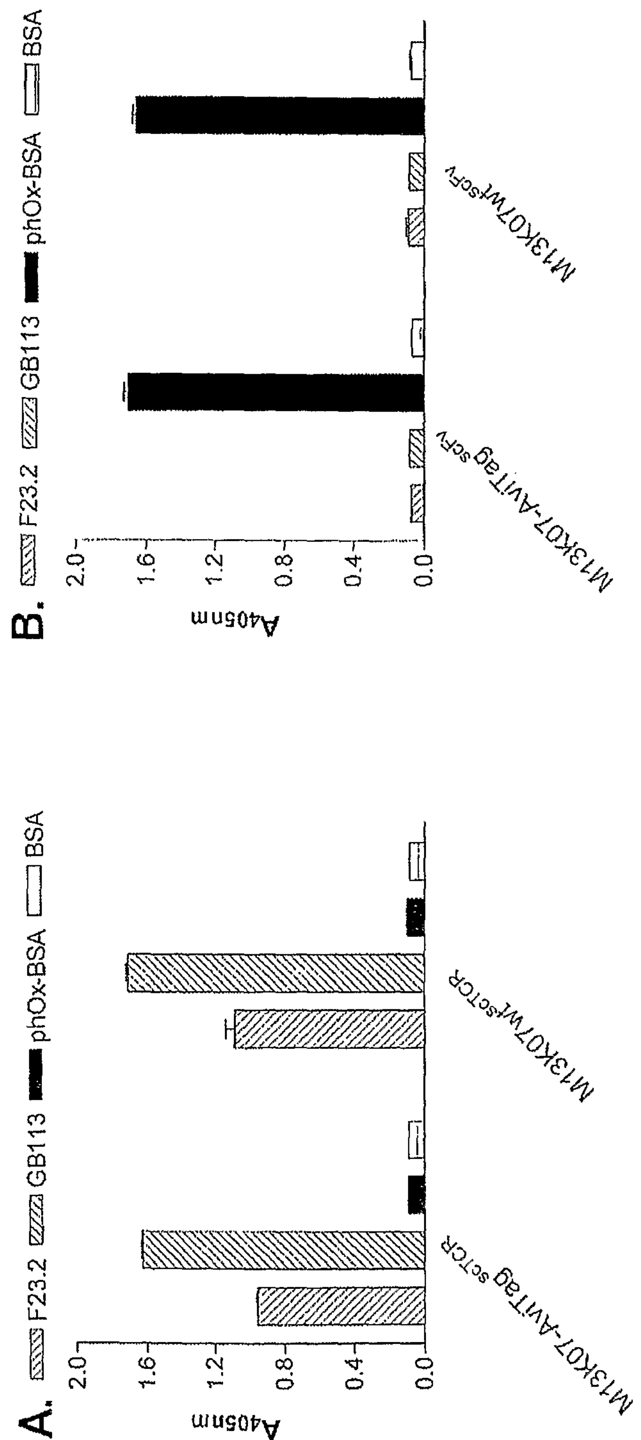

FIG. 10: ELISA analysis showing functionality of scTCRpIII (A) and scFvpIII (B) displayed on phagemid-derived virions with pVIIAviTag. Normalised phage preparations were used.

Figure 11:
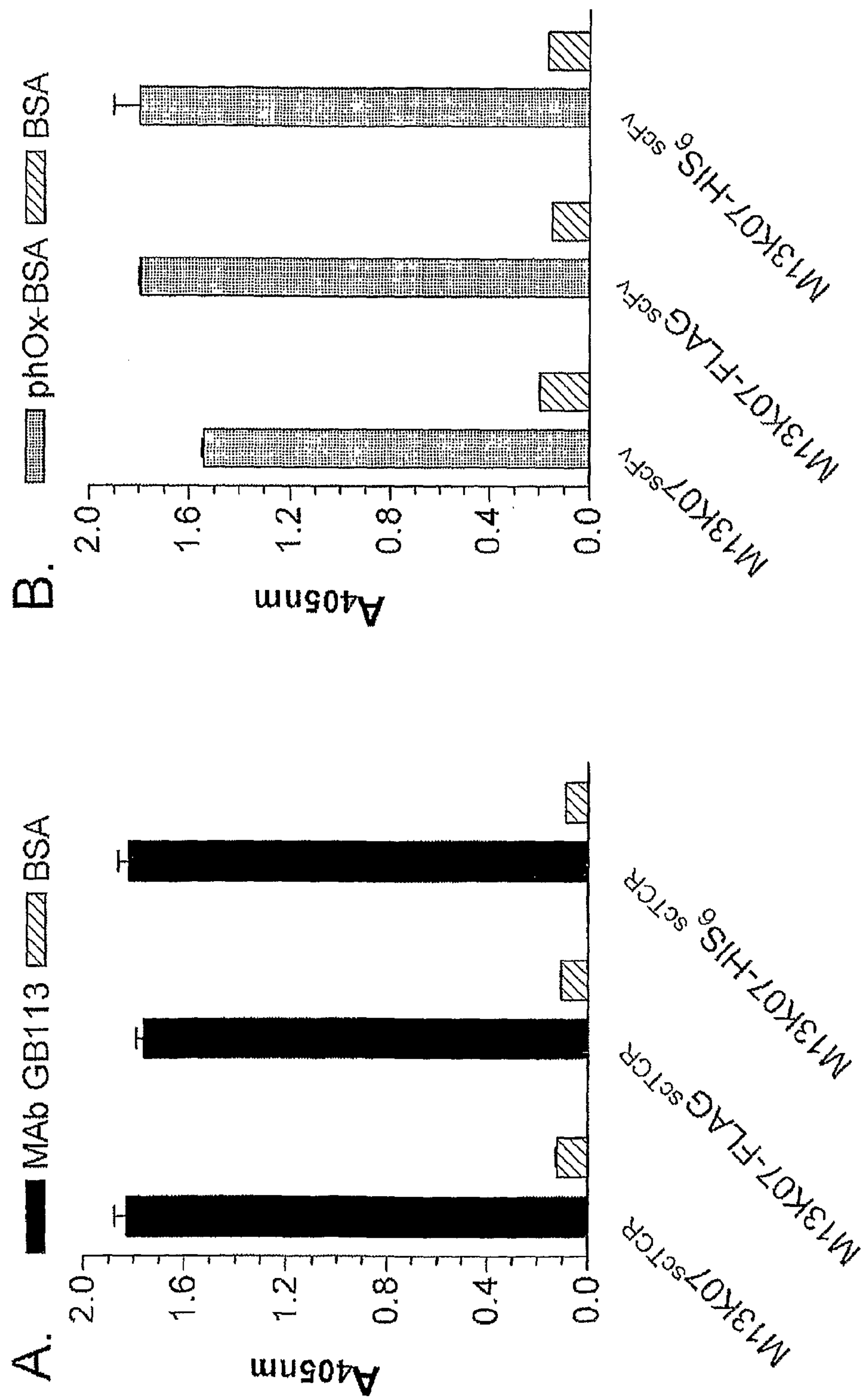

FIG. 11: Analysis showing functionality of scTCR (A) and scFv (B) displayed on phagemid derived virions with FLAG-tag and HIS6-tag. Normalised phage preparations were used.

Figure 12:
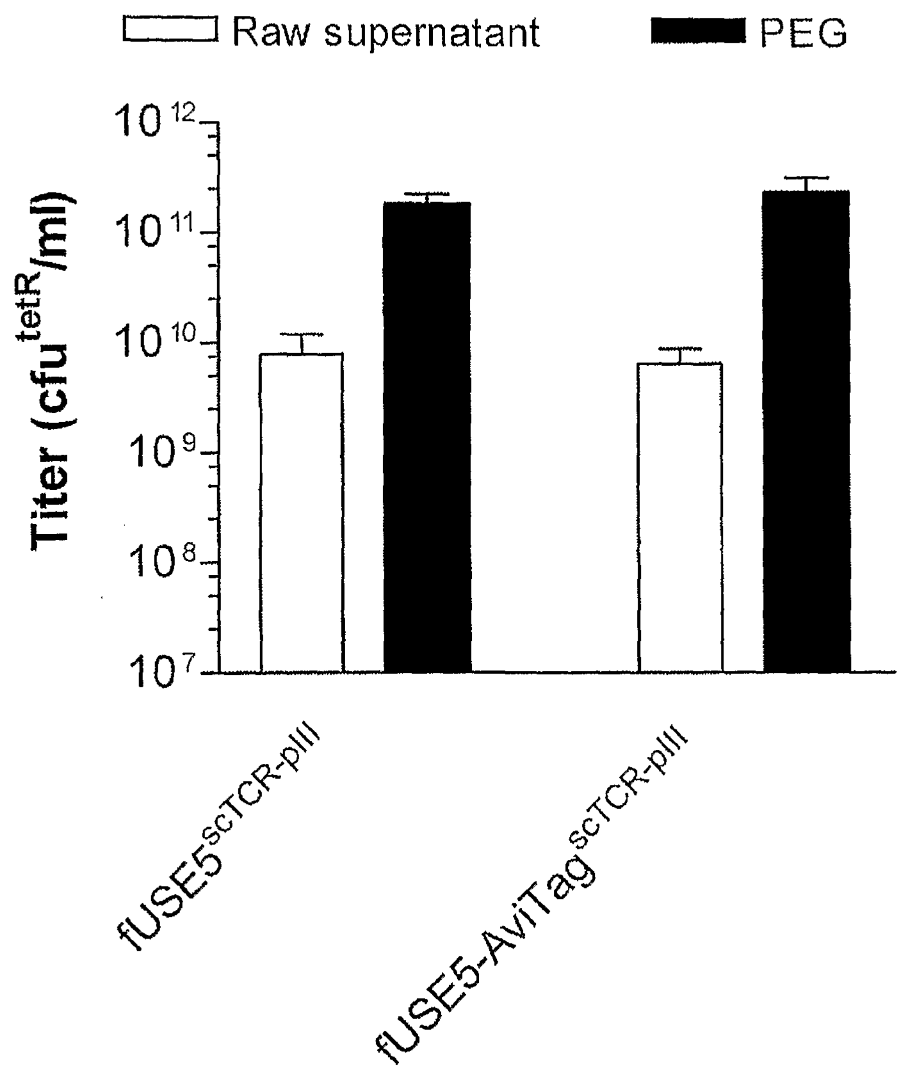

FIG. 12: Titre of genomic phage fUSE5-scTCRpIII with and without pVIIAviTag.

Figure 13:
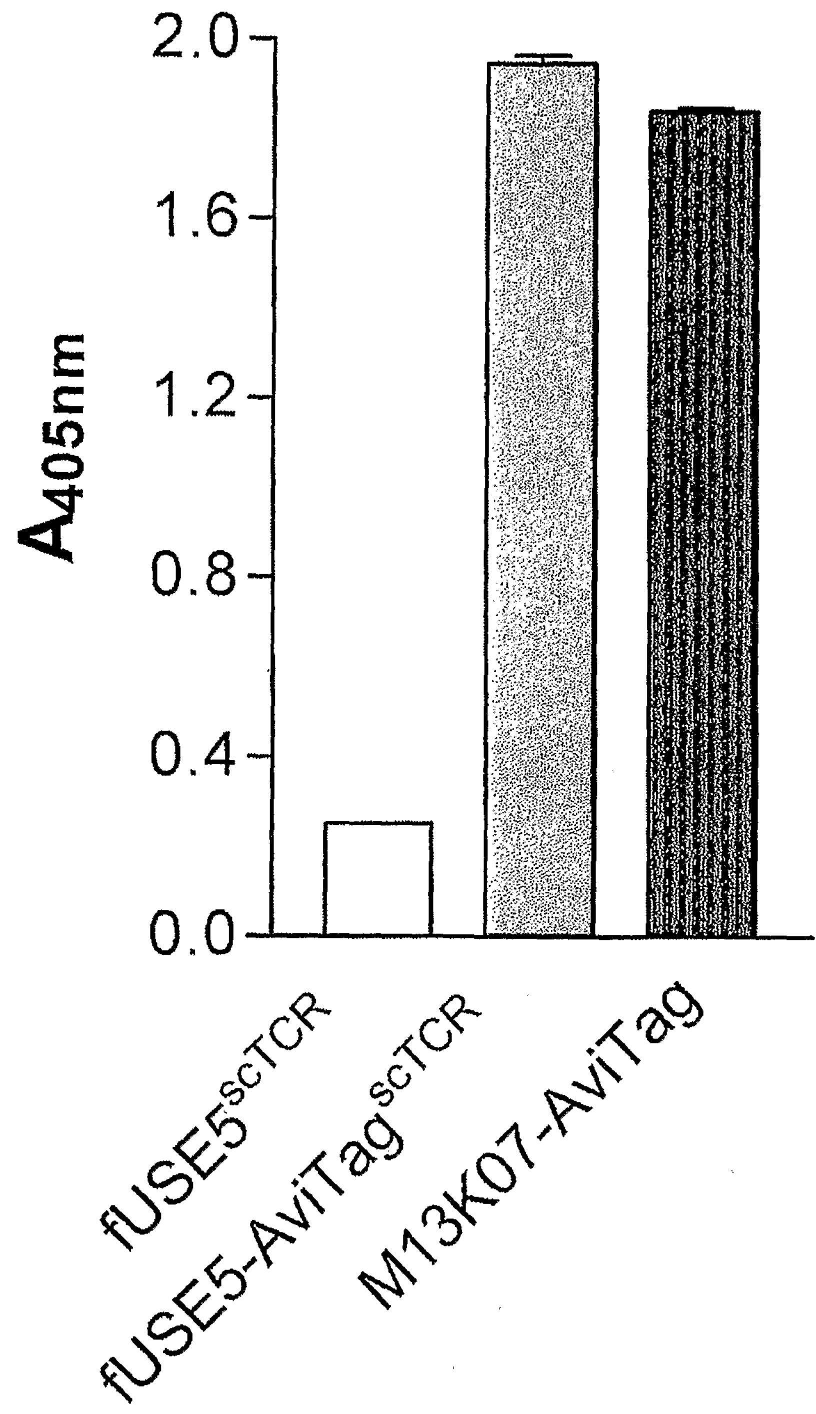

FIG. 13: ELISA analysis showing the functionality of genomic fUSE5-AviTag phage preparations by capturing phages by streptavidin beads followed by detection of bound phages by anti M13-Antibodies. Normalised phage preparations were used.

Figure 14:
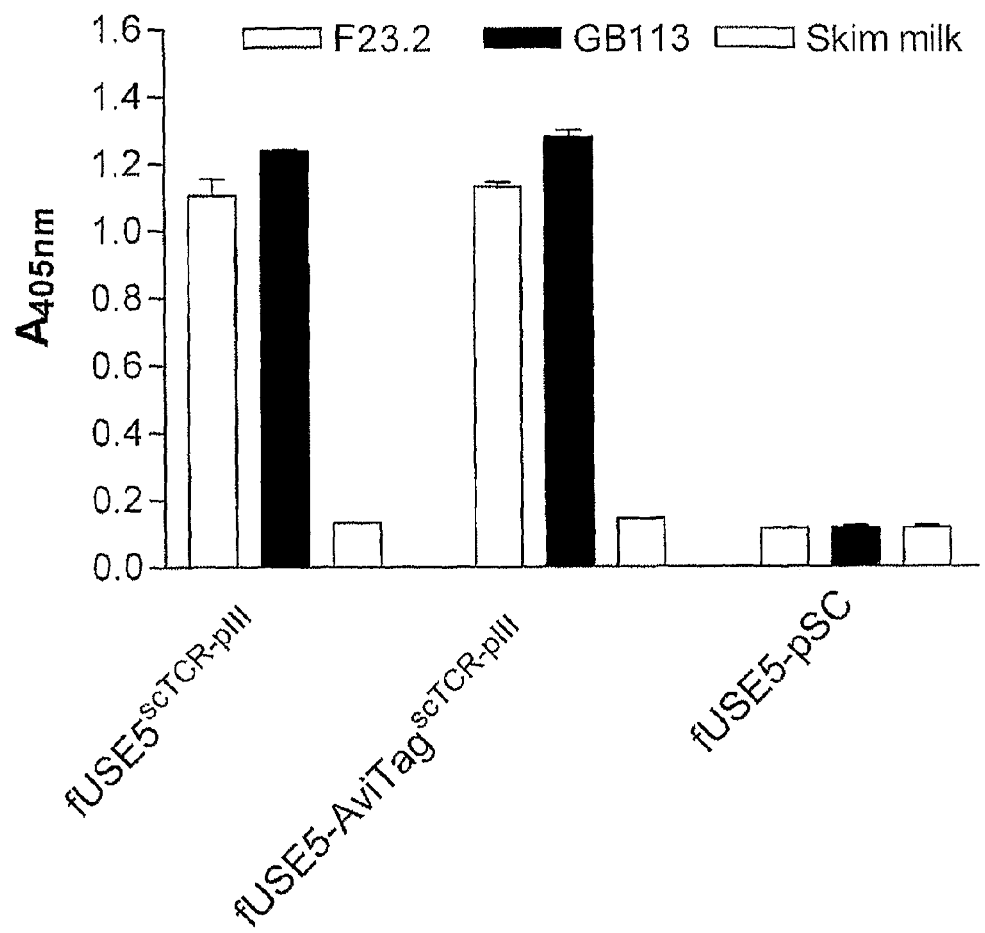

FIG. 14: ELISA analysis showing the functionality of pIII-displayed scTCR on genomic phage fUSE5 with Avitag-pVII. Normalised phage preparations were used.

Figure 15:
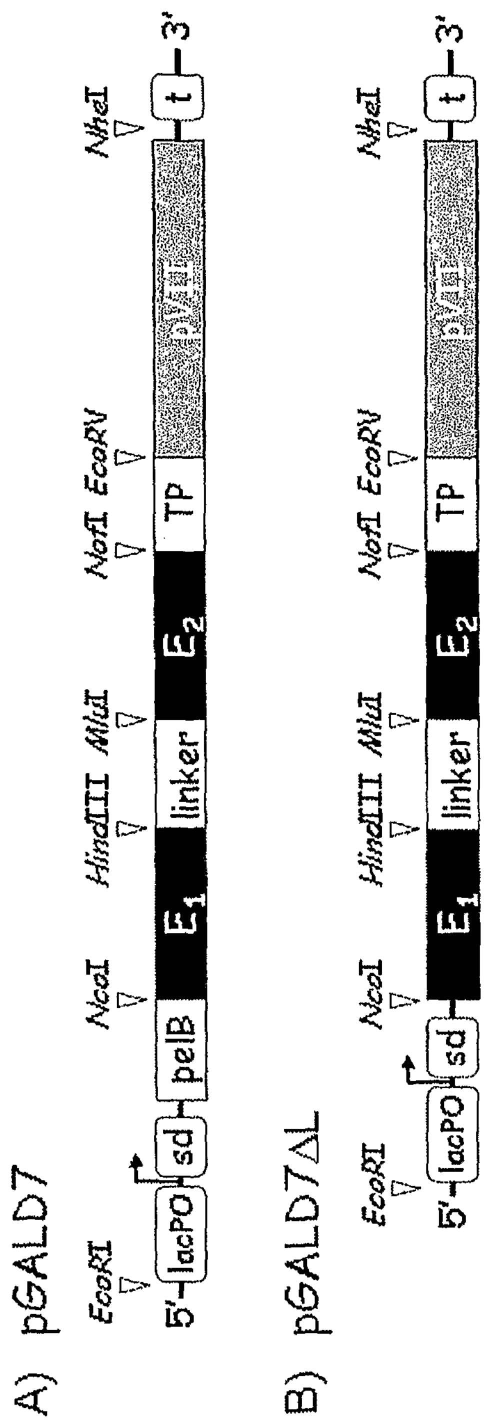

FIG. 15: Schematic drawing of the novel pGALD7 (A) and pGALD7DL (B) pVII display phagemids. The vector backbone of both phagemids was based on the pSEX81 (SEQ ID NO:29), which sequence can be accessed from GenBank accession no.: Y14584, and details on the constructed are described in Material and Methods. Both phagemids can accommodate cassettes of in frame exogenous sequences (termed E1 and E2) through easy cassette exchange of the NcoI/HindIII and MluI/NotI portions respectively. The cassettes are connected by a synthetic linker sequence that vary among the different constructs described herein. Abbreviations: lacPO, lac promoter; sd, Shine-Dalgarno sequence; pelB, signal sequence of bacterial pectate lyase; TP, trypsine protease site; t, T7 transcriptional terminator.

Figure 16:
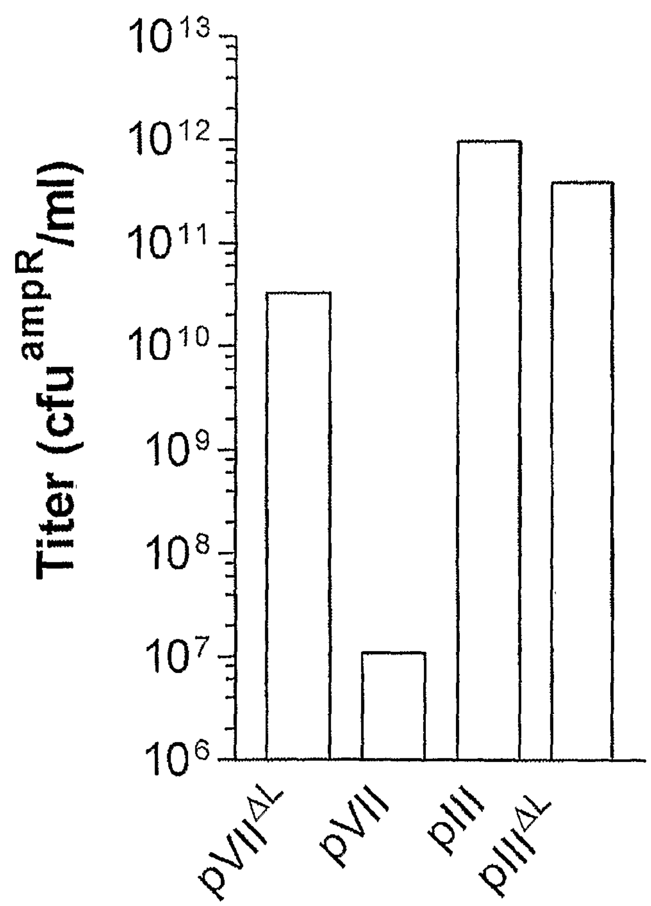

FIG. 16: Phagemid titers of scFv anti-phOx (SEQ ID NO:26) displayed from pGALD7ΔL (pVIIΔL), pGALD7 (pVII), pSEX81 (pIII) and pSEX81ΔL (pIIIΔL). All the phagemids harbour an ampicillin resistance marker, hence the titers are shown as ampicillin resistant colony forming units per milliliter solution (cfuampR/ml).

Figure 17:
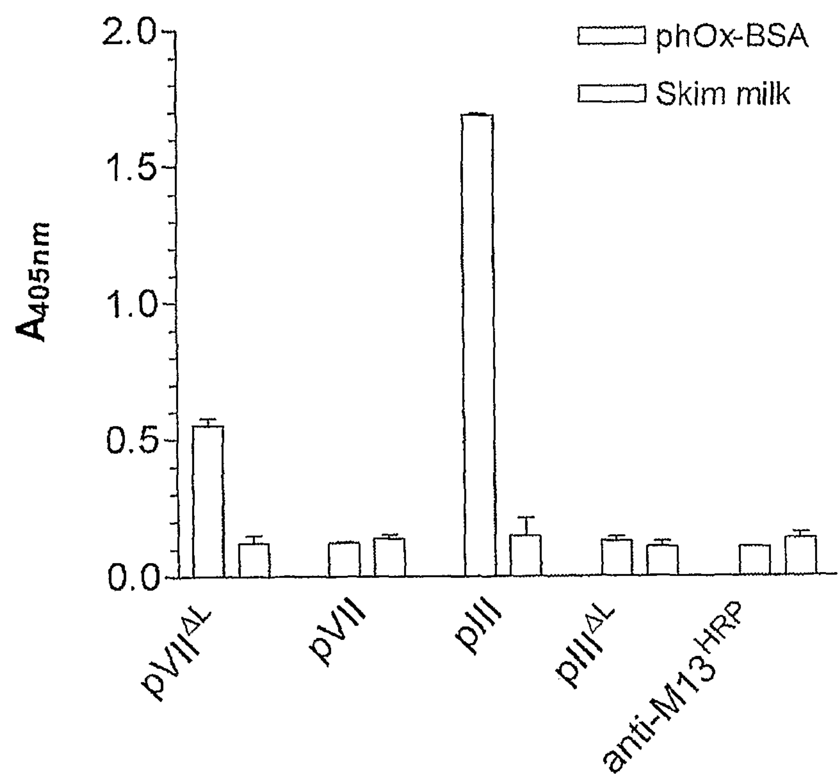

FIG. 17: Antigen specific (phOx-BSA) ELISA comparing functional scFv anti-phOx (SEQ ID NO:26) display between pVII and pIII, and with and without signal sequence (ΔL). The ELISA was conducted as described in materials and methods and the titer input was $2\times10^{10}$ cfuampR/ml for all samples, except for the pGALD7 (pVII), which was used undiluted (corresponding to $1.1\times10^{7}$ cfuampR/ml). The anti-M13HRP is a negative control on unspecific adsorbsion of the virion detection MAb to the antigen and block.

Figure 18:
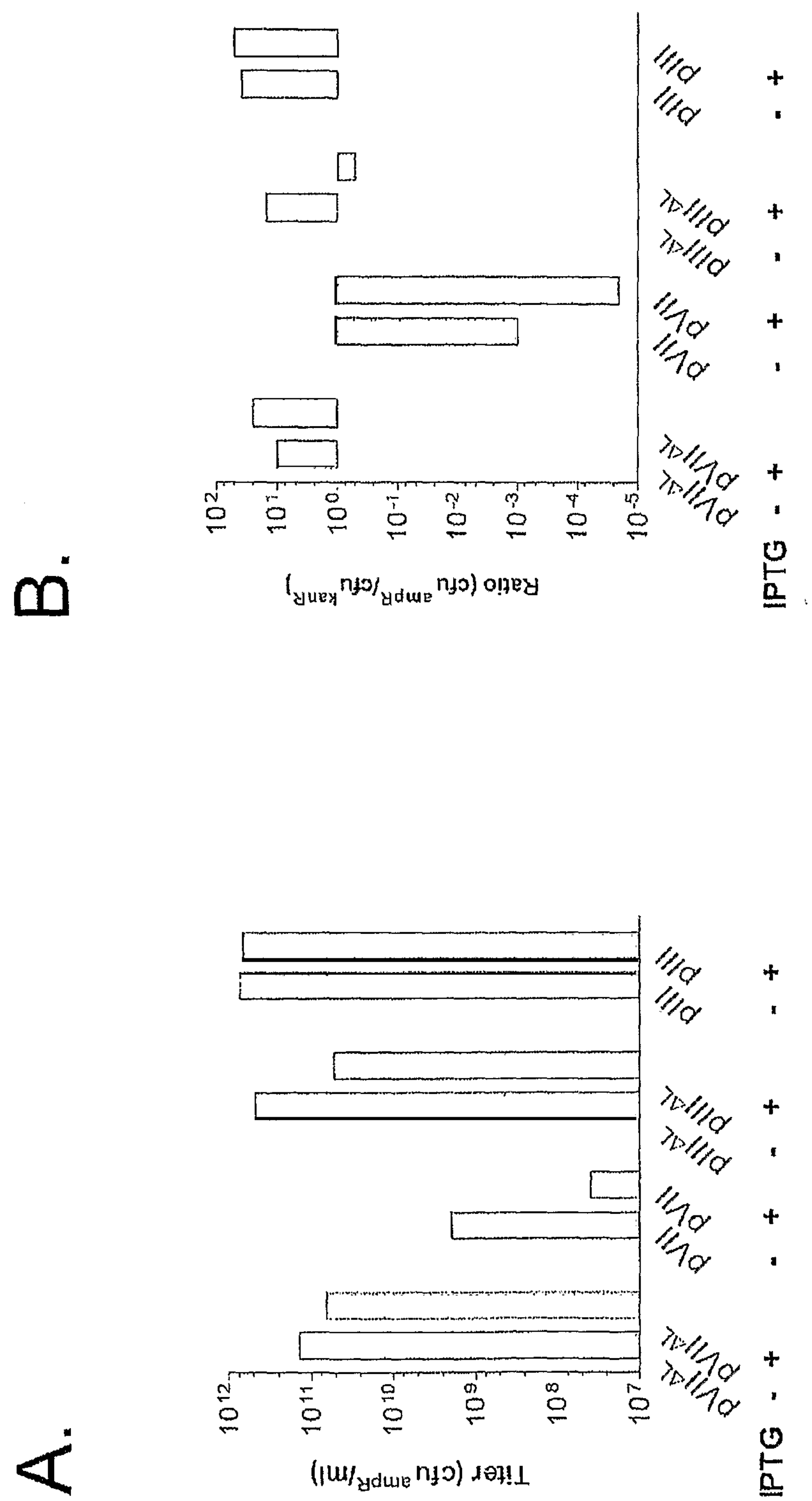

FIG. 18: (A) Phagemid titers of scFv anti-phOx displayed from pGALD7ΔL (pVIIΔL), pGALD7 (pVII), pSEX81 (pIII) and pSEX81ΔL (pIIIΔL) shown as cfuampR/ml. (B). Phagemid to helper phage ratios shown as the ratio of the phagemid titer (cfuampR/ml) divided by helper phage titer (cfukanR/ml). The virion packaging was done as standard phagemid rescue as described in materials and methods (−), or with a final concentration of 0.1 mM IPTG present after super infection in both A and B.

Figure 19:
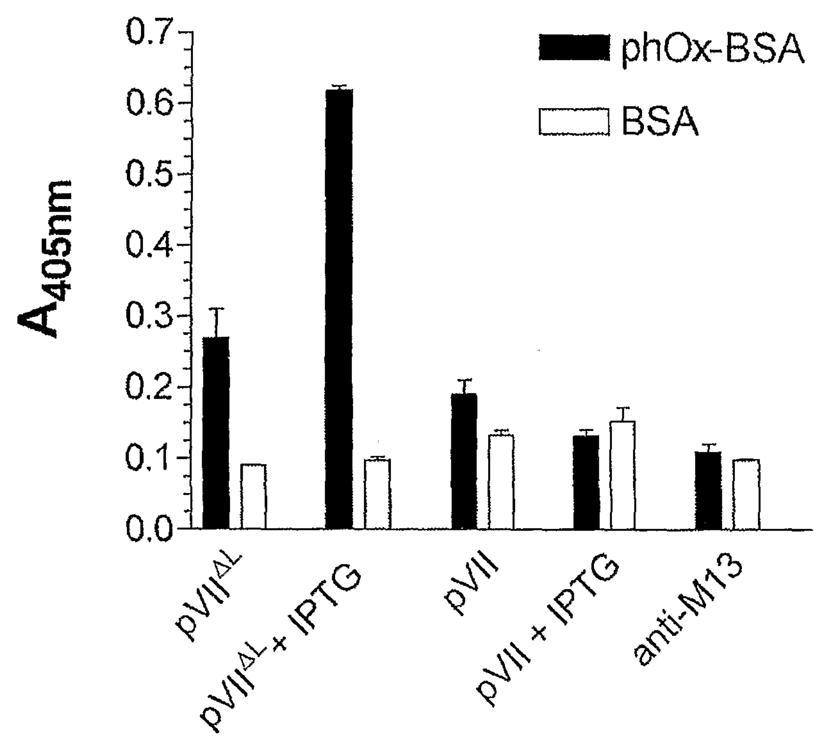

FIG. 19: Antigen specific (phOx-BSA) ELISA comparing functional scFv anti-phOx pVII display with and without signal sequence (ΔL) and with and without IPTG induction (0.1 mM) of the pVII fusion expression. The ELISA was conducted as described in materials and methods and the titer input was $2\times10^{10}$ cfuampR/ml for pGALD7ΔL (pVIIΔL), whereas the pGALD7 (pVII) was used undiluted (corresponding to $2.0\times10^{9}$ and $1.1\times10^{7}$ cfuampR/ml without and with IPTG, respectively). The anti-M13HRP is a negative control on unspecific adsorbsion of the virion detection MAb to the antigen and block.

Figure 20:
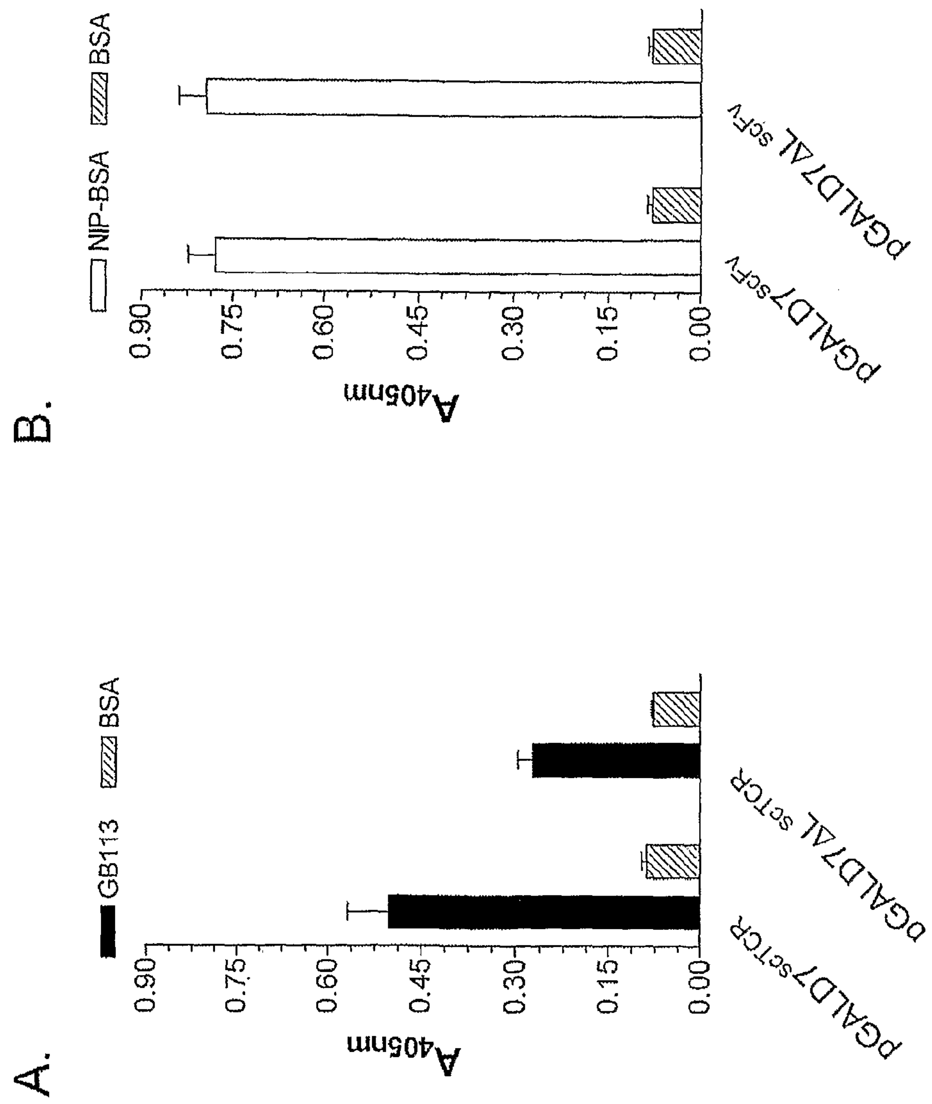

FIG. 20: Antigen specific ELISA comparing functional scTCR (A) and scFv-anti-NIP (B) pVII display with and without signal sequence (ΔL). The ELISA was conducted as described in materials and methods using equal volumes on undiluted cleared supernatant. The anti-M13HRP is a negative control on unspecific adsorbsion of the virion detection MAb to the antigen and block. In (A), the GB113 antibody clone specific for the 4B2A1 T cell receptor (Bogen et al, PMID: 1700755) was used as surrogate antigen substituting for the cognate I-Ed/λ2315 ligand to the scTCR Vαβ4B2A1 (Loset et al, PMID: 17925331).

Figure 21:
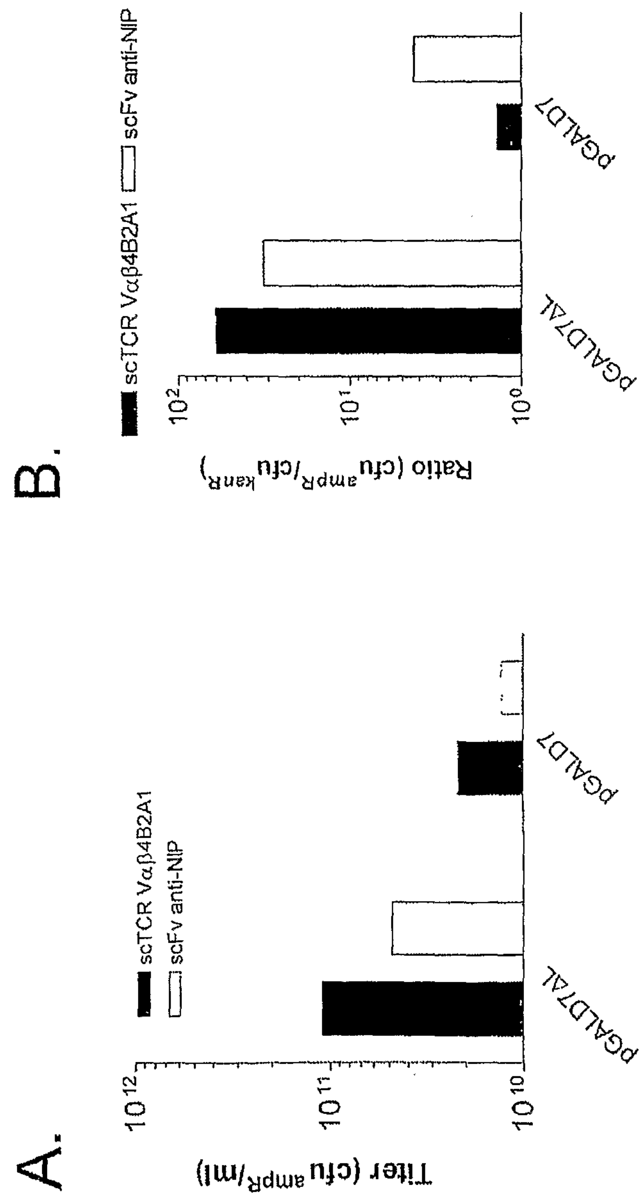

FIG. 21: (A) Phagemid titers of the scTCR Vαβ4B2A1 and the scFv anti-NIP (SEQ ID NO: 27) displayed from pGALD7ΔL and pGALD7 using standard phagemid rescue as described in material and methods. (B) Phagemid-to-helper phage ratios of the same samples as in (A).

Figure 22:
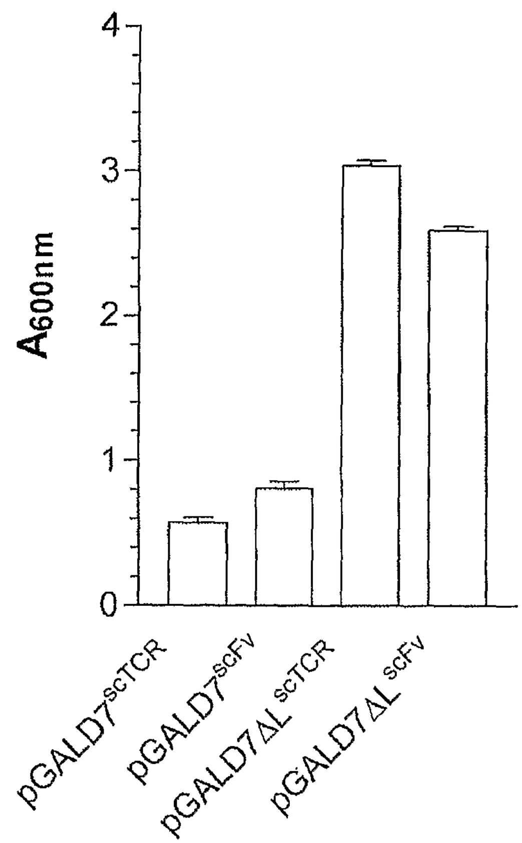

FIG. 22: (A) Cell density of the respective *E. coli* cultures at the end of the virion packaging protocol measure as optical density (OD) at A600 nm Notably, all cultures were initiated an identical density of A600 nm 0.025 and super infected with M13K07 at M015 when A600 nm 0.1 was reached. Packaging was then allowed to proceed ON at 30° C. before end culture OD was measured.

Figure 23:
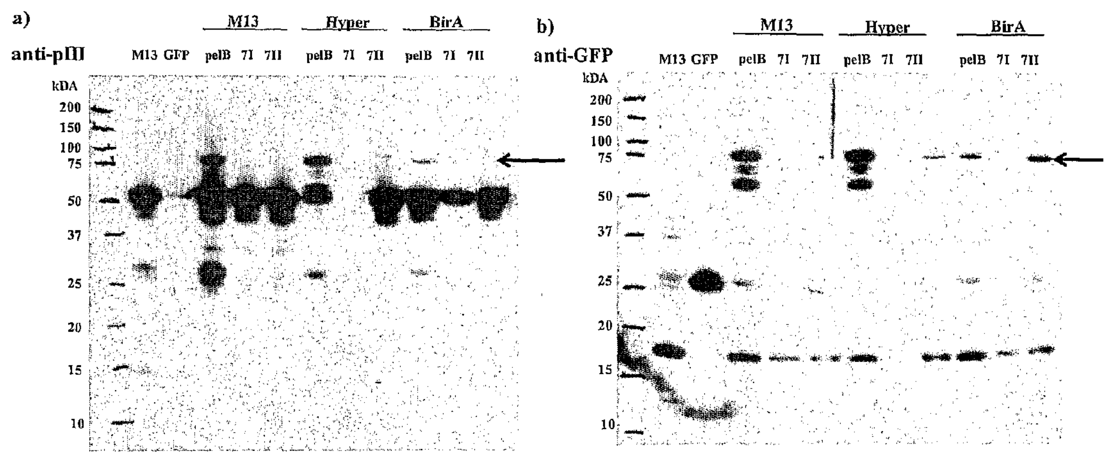

FIG. 23: Western-Blot detection of GFP in fusion to pIII using different leader signal sequences and different helper phages for phage amplification. The fusion protein is indicated with a black arrow and has an approximate size of 75 kDa. Marker sizes are at the left. (a) Anti-pIII detection. M13 helper phage was a positive control; (b) Anti-GFP detection. GFP was a positive control.

Figure 24:
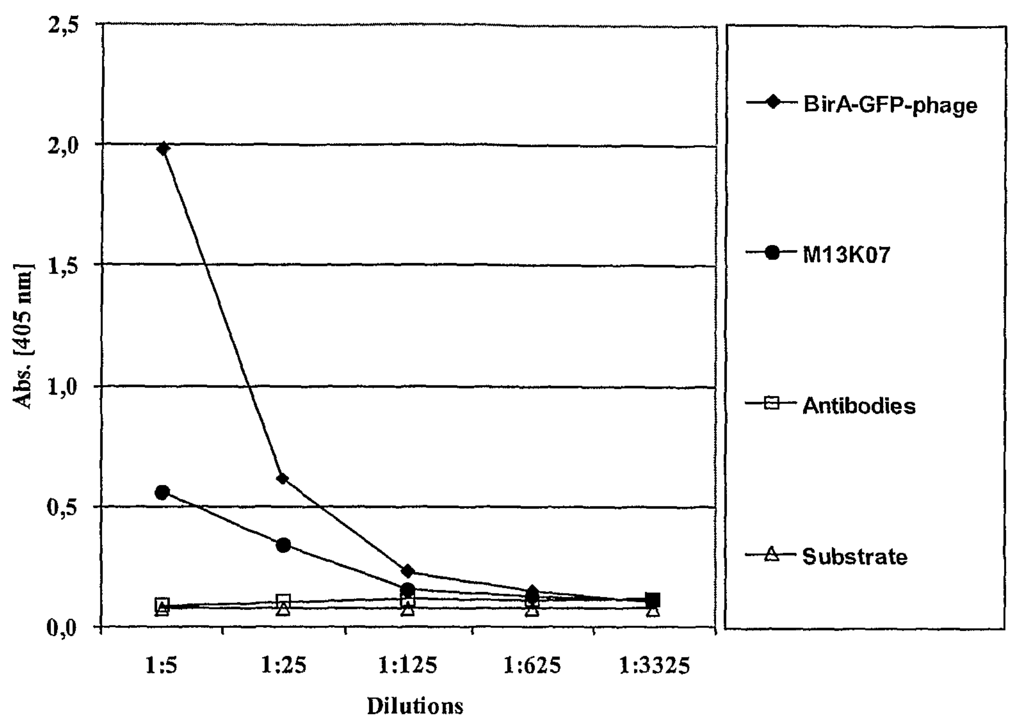

FIG. 24: Coupling of BirA-amplified GFP-phages to streptavidin beads in comparison to M13K07 phages, lacking a Biotin-tag. As a control signals were compared to substrate and the detection antibodies.

Figure 25:
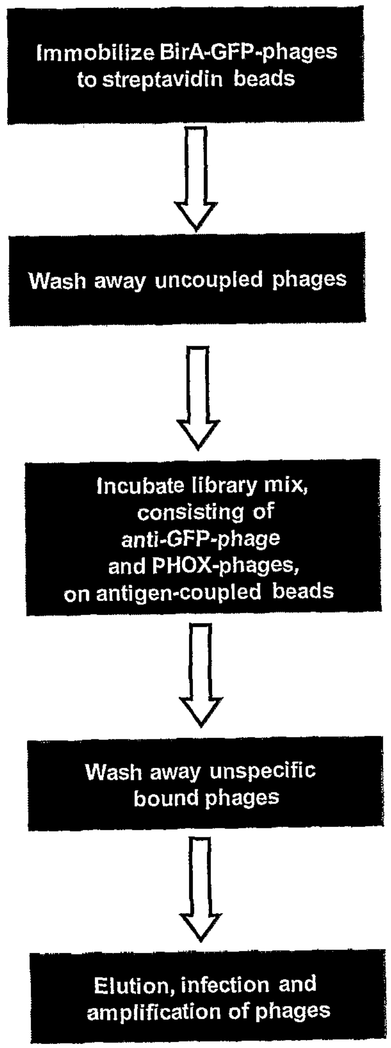
Figure 25:
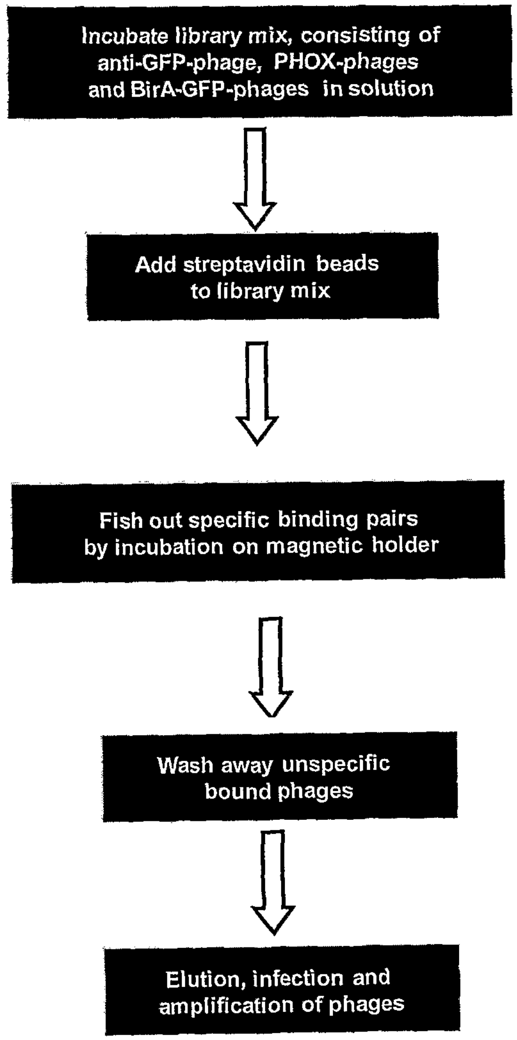

FIG. 25: Schematic representation of two possible scenarios during library vs library panning Scenario I: the antigen-phage is first coupled to streptavidin, followed by incubation of the library mix on the antigen-coupled beads. Scenario II: all library members, including the antigen-phages, are first incubated in solution.

Figure 26:
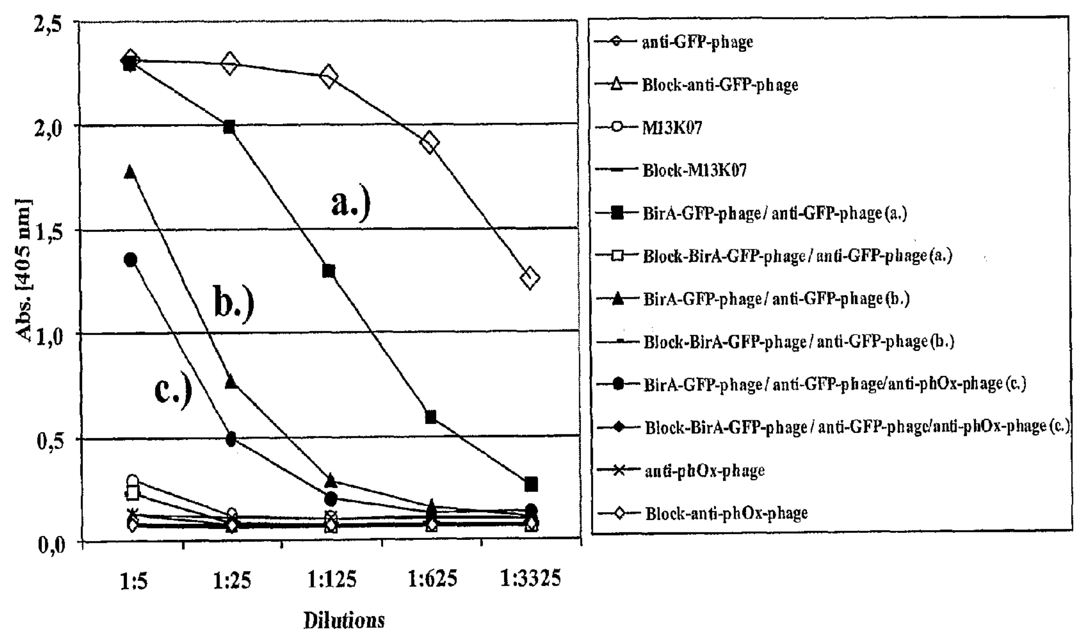

FIG. 26: Phage-ELISA on immobilized GFP (10 μg/ml). Phages were incubated in the presence of 4% milk in PBS pH7.4 and detected with Rabbit-anti-Fd-antibody, followed by incubation with a HRP-coupled secondary antibody. The different set-ups described in the text are indicated with a.), b.) and c.). Binding of phages alone or phage complexes as outlined in legend above is compared to binding on block-only coated wells. Pure anti-GFP-phage served as positive control. M13K07-phages as well as anti-phOx-phages used in setting c.) in a first spiking experiment were also included to test for background binding.

Figure 27A:
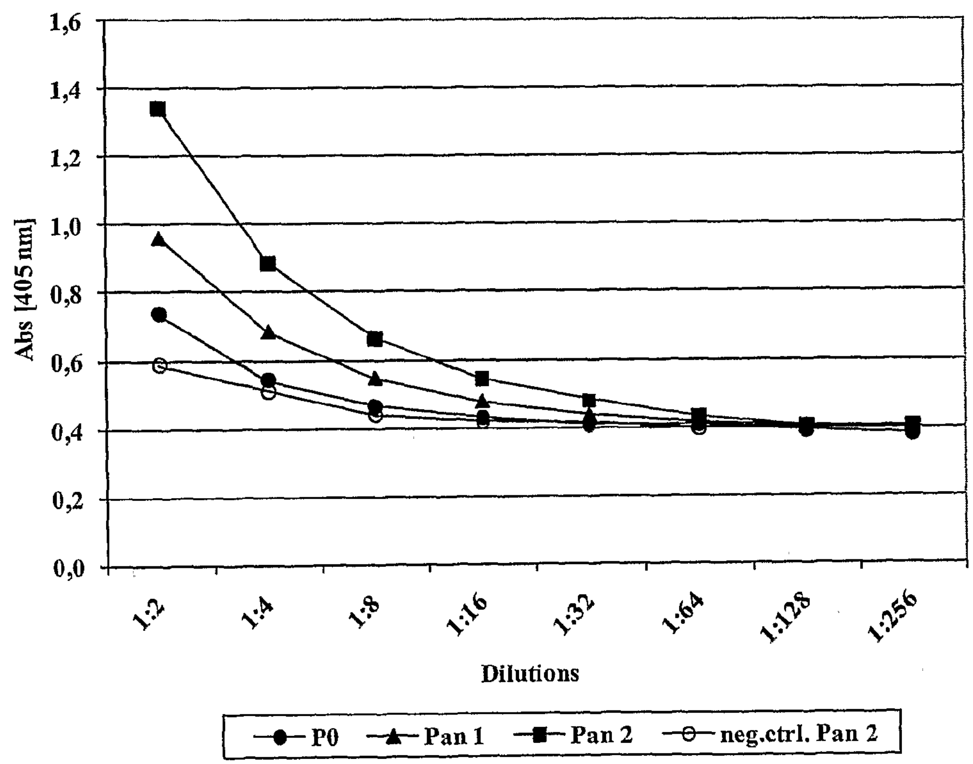
Figure 27B:
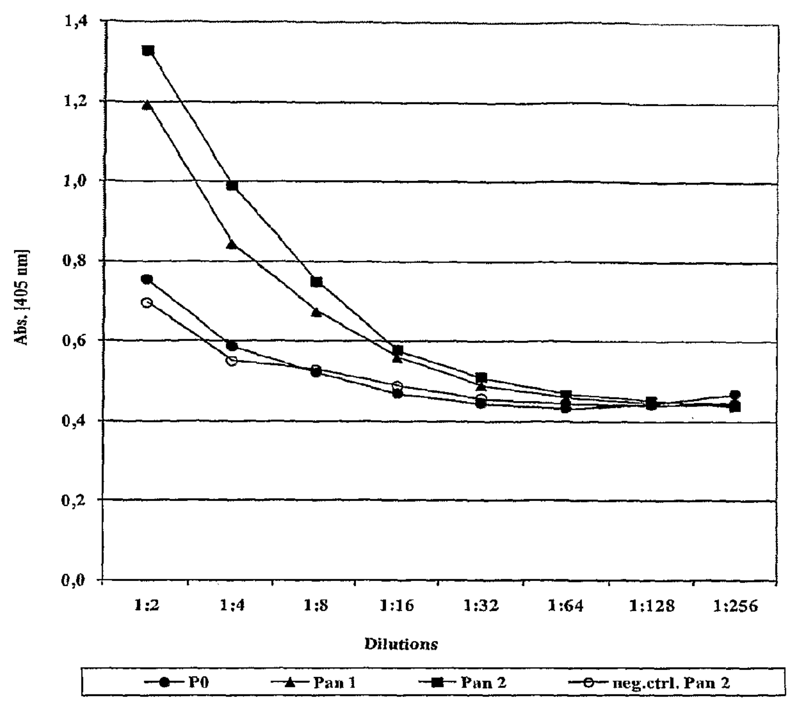
Figure 27C:
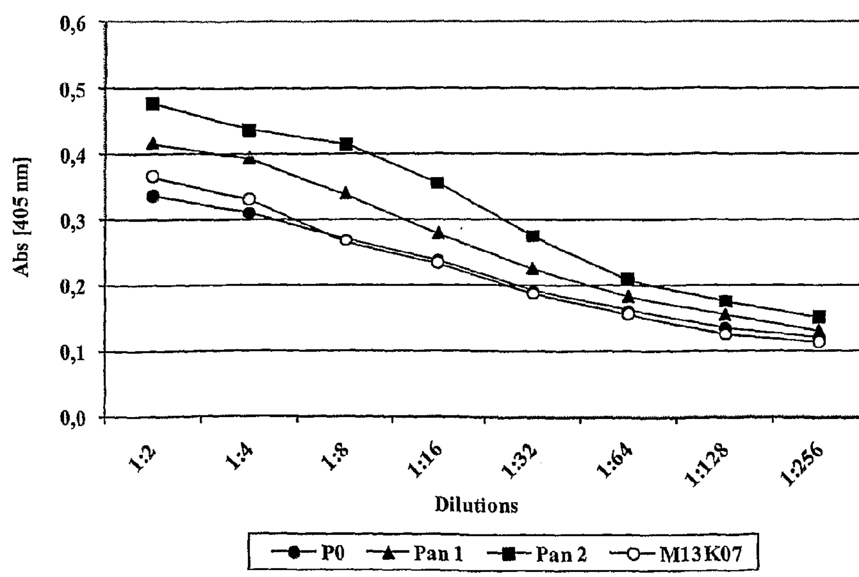

FIG. 27: Evaluation of enrichment of anti-GFP-phage (panels a & b) or GFP-phage (panel c) after 2 panning rounds (Pan 1, 2) by phage-ELISA. Signals were detected by absorbance measurements at 405 nm.

a) Phage ELISA on immobilized GFP for panning round 1 and 2 for $1:10^{6}$ spiking library from scenario I (panning on precoupled beads). Phages were normalized (same amount of phages was tested for each panning round). For comparison, P0 from the $1:10^{6}$ spiking as well as phages from panning round 2 of the neg.ctrl. (no anti-GFP-phage present) were included in the ELISA experiment. Detection was with anti-Fd.

b) Phage ELISA on immobilized GFP for panning round 1 and 2 for $1:10^{6}$ spiking library from scenario II (all library members kept in solution before incubation with beads). Phages were normalized. For comparison, P0 from the $1:10^{6}$ spiking as well as phages from panning round 2 of the neg.ctrl. (no anti-GFP-phage present) were included in the ELISA experiment. Detection was with anti-Fd.

c) Detection of GFP-pIII fusion of amplified phages by ELISA (immobilised phages) from panning round 1 and 2 for $1:10^{6}$ spiking library from scenario I (panning on precoupled beads). For comparison, P0 from the $1:10^{6}$ spiking as well as M13K07 helper phages were included in the ELISA experiment. Detection was with anti GFP IgG.

EXAMPLES

Example 1

Modified Helper Phages with Peptides Fused to pVII

Modified helper phages M13K07 (SEQ ID NO: 31) and VCSM13 (SEQ ID NO: 32), with FLAG-pVII, HIS6-pVII, and AviTag-pVII may show a very broad potential for expanding the use of phage display technology, but it is of crucial importance that the fusion peptides do not compromise the functionality of the helper phage, thus titration of the phages are an important verification parameter. In addition the peptides fused to pVII must be accessible for the subsequent detection and/or immobilisation. This example support the fact that both pVII-modified helper phages can harbor a variety of peptides for detection and/or immobilization purposes and that these fusion peptides do not affect the infectivity of the phages.

Whilst early results from Endemann and Model (PMID: 7616570) indicated that the filamentous phage (Ff) capsid protein pVII did not tolerate exogenous fusions, it has later been shown that both phagemid-based (Gao et al (PMID: 10339535) and phage genome-based (Kwasnikowski et al (PMID: 16277988) peptide and folded domain display may be allowed as N-terminal fusions to pVII. In both cases, it is emphasized that the key to success required periplasmic targeting of the fusion protein by adding a prokaryotic signal sequence, or leader peptide, to the extreme N-terminus of the fusion, thus targeting the fusion to the SEC pathway of the *E. coli* host.

Productive pVII display has previously only been shown in the context of N-terminal fusions encoded on a phagemid harboring a N-terminal leader peptide ensuring transport of the recombinant pVII to the periplasmic compartment (Endeman et al, 1995; Gao et al, 1999).

However, it is known that before being incorporated into the virion, wt pVII is found as an integral membrane protein in the inner membrane of the gram negative *E. coli* host, having its N-terminus facing the periplasmic space. Moreover, as this membrane bound, mature wt pVII retains its amino-terminal formyl group (Simons et al, PMID; 6945579), it does not appear to be N-terminally processed by e.g. the periplasmic leader peptidases, as is the case with the vast majority of signal sequence-directed proteins found outside the cytosolic compartment (Baneyx and Mujacic, PMID: 15529165). As no apparent signal sequence-like motif can be identified in the pVII ORF, its mode of translocation from the cytosol to the periplasm remains elusive, but most likely does not involve the four major secretory machineries identified in *E. coli*, namely the SEC-, SRP- and Tat- and YidC pathways (Baneyx and Mujacic, PMID: 15529165; Samuelson et al, PMID: 10949305). The structure of filamentous phage virion is shown in FIG. 1.

Reagents

All media and buffers were prepared essentially as described in Sambrook et al (Molecular cloning: a laboratory manual (Cold Spring Harbor Laboratory Press)). The anti-M13-HRP antibody and the M2 and M5 antibodies were purchased from GE Healthcare Bio-Sciences AB (Uppsala, Sweden) and Sigma-Aldrich (Oslo, Norway), respectively. Restriction enzymes (RE) were purchased from New England Biolabs (Ipswich, Mass., USA) with the exception of DpnI, which was obtained from Stratagene (LaJolla, Calif., USA). DNA oligos were purchased from MWG Biotech AG (Ebersberg, Germany). Dynabeads MyOne™-Streptavidin magnetic beads and Talon™ Ni-NTA magnetic beads were both purchased from Invitrogen (Oslo, Norway). BSA and Tween 20 was purchased from Sigma-Aldrich (Oslo, Norway). Pfu Ultra DNA and Phusion DNA polymerases were purchased from Stratagene (LaJolla, Calif., USA) and Sigma-Aldrich (Oslo, Norway), respectively. TMB soluble was from Chalbiochem.

Bacterial Strains, Phage

The *E. coli* strains XL1-Blue was purchased from Stratagene (LaJolla, Calif., USA). M13K07 helper phage was purchased from GE Healthcare Bio-Sciences AB (Uppsala, Sweden) whereas VCSM13 (SEQ ID NO: 32) was purchased from Stratagene (LaJolla, Calif., USA).

Design and In Vitro Mutagenesis of AviTag™-, HIS6-, and FLAG-pVII.

The open reading frame (ORF) of the AviTag™ (N-MSGLNDIFEAQKIEWHE-C; SEQ ID NO:4) was compared to the codon usage in *E. coli* K12 strains using the GCUA server (see the website having the URL "gcua.schoedl.de/seqoverall.html"). A prokaryotic codon-optimized version of the AviTag™ peptide sequence (SEQ ID NO:4) was attached N-terminally to the pVII ORF by QuikChange™ in vitro mutagenesis according to the manufacturers' protocol (Stratagen, LaJolla, Calif., USA), using the primer pair BirA-p VII_frwd/BirApVII_rev (5'CCGGCTAAGTAACATGTCCGGCCTGAACGATA TCTTTGAAGCGCAGAAAATTGAATGGCATGAAATGGAGCAGGTC-'3/5' GACCTGCTCCATTTCATGCCATTCAATTTTCTGCGCTTCAAAGATATCGTTCAGGC CGGACATGTTACTTAGCCGG-3') (SEQ ID NO:5 and SEQ ID NO:6, respectively). In the same manner as described above, *E. coli* K12 codon optimized versions of the FLAG-tag (N-DYKDDDDK-C) (SEQ ID NO:9) and the HIS6-tag (N-HHHHHH-C) (SEQ ID NO:12) were attached N-terminally to the pVII ORF using the primer pairs FLAG-pVII-frwd/FLAG-pVII-rev (5'-CCGGCTAAGTAA CATGGACTACAAAGATGACGATGACAAAATGGAGCAGGTCG-3'/5'-CGACCTGCTCCATTTTGTCATCGTCATCTTTGTAGTCCATGTTACTTAGCCGG-3') (SEQ ID NO:7 and SEQ ID NO:8, respectively) and HIS6-pVII-frwd/HIS6-pVII-rev (5'-CCGGCTAAGTAACATGCATCACCATCACCATCACATGGAGC AGGTCG-3'/5'-CGACCTGCTCCATGTGATGGTGATGGTGATGCATGTTAC TTAGCCGG-3') (SEQ ID NO:10 and SEQ ID NO:11, respectively), respectively. The various constructs were verified by DNA sequencing (in-house ABI lab DNA sequencing core facility, Dept. Molecular Biosciences, University of Oslo) in all cases. To ensure a clean vector background, a BsrGI/SnaBI RE fragment containing the modified pVII was moved into either the M13K07 wt or VCSM13 wt genome on compatible RE sites using standard techniques. The DNA constructs were introduced into the various *E. coli* hosts by electroporation. Primer design was based on a sequence alignment of the M13K07 (New England Biolabs sequence) (SEQ ID NO:31) and VCSM13 (GenBank accession no.: AY598820) (SEQ ID NO:32) sequences using ClustalW. The sequence of the modified AviTag™-, HIS6-, and FLAG-sequences are shown in FIG. 2.

Preparation of Phage Particles

Phages were amplified from *E. coli* XL1-Blue transformed with the M13K07 (SEQ ID NO: 31), VCSM13 (SEQ ID NO: 32) constructs essentially as described (Scott and Smith, PMID: 1696028).

SA Bead-Capture of Biotinylated Virions 10 ml/Tube™-Streptavidin beads were transferred to fresh 1.5-ml tubes and 500 ml 2% BSA in PBS (w/v) was added. Likewise, 250 ml of cleared supernatant or the appropriate amount of phages were transferred to 1.5-ml tubes and supplemented with 250 ml of 2% BSA. The tubes were then incubated for 1 h at room temperature (RT) on a rotating wheel. Thereafter, the beads were washed 3× by first immobilizing the beads by using a Dynal tube magnet rack. The supernatant was discarded and 0.5 ml of PBS containing 0.05% Tween 20 (PBST) added to each tube. The tubes were taken out of the rack and briefly vortexed before re-entered into the rack. The supernatant was again cleared and the washing repeated twice. The tubes were removed from the rack and 250 ml of blocked phage and 250 ml PBST were added to each tube. The tubes were then incubated for 1.5 h/RT on a rotating wheel. The tubes were washed 3× in PBST as described above. 0.5 ml of PBST containing anti-M13 MAb-HRP (1:2000) was then added to each tube and the tubes were incubated for 1 h/RT on a rotating wheel. The tubes were washed 3× in PBST as described above. 0.5 ml of ABTS was then added to each tube and the tubes left on the bench for 30 min, before place in the magnet rack and 100 ml supernatant transferred to Maxisorp ELISA strips (Nunc, Roskilde, Denmark). The absorbance was then measured at A405 nm using a TECAN ELISA reader apparatus.

Phage-Capture Enzyme Linked Immunosorbent Assays (ELISAs)

M2 and M5 antibodies were absorbed to MaxiSorpä microtiter plate wells (Nunc, Roskilde, Denmark) in concentrations from 2.5 to 5 mg/ml in PBS, pH 7.4 overnight at 4° C. The wells were blocked with 2% skim milk in PBS (w/v) for 1 h at RT, virion preparations where then added and allowed to react for 1 to 2 h at RT before captured virions were detected with anti-M13-HRP (1:5,000) for 1 h at RT. Between each step, the wells were washed 3× with PBST. The wells were developed with ABTS substrate and the absorbance read at A405 nm after 30 min.

Results

A—Titration of Helperphages.

16 ml 2×YT were inoculated with a fresh XL1-Blue culture and incubated at 37° C./250-rpm to an A600 nm 0.4-0.8. 10 μl of each diluted phage preparations were transferred to a 96-well microtiter plate. 190 μl of the XL1-Blue culture was transferred to each well with the phage diluents. The plate was incubated for 50 min/37° C. BA82/20 membrane was overlaid a LB-kan agar-dish, a volume of 3 μl/sample spotted on the membrane and the dish incubated at 37° C./ON. Colonies were counted (FIG. 3).

B—Accessibility and Functionality of the Inserted Peptides

Avitag:

The BirA enzyme is an acetyl-CoA-carboxylase and is found endogenously in all *E. coli*. It has indeed been shown that the introduction of AviTag in the context of phage into such cells results in a small level (~7%) of target biotinylation by endogenous BirA (Sholle et al, PMID: 16628754). To test whether or not the N-terminal pVII modification actually were functional in that virions were assembled and worked as an enzymatic substrate for BirA, we tested if the resulting virions could be captured from crude supernatant using SA-coated magnetic beads.

Capture of M13K07-AviTag pVII by Dynal Streptavidin beads. Two phages were employed in the assay: M13K07-AviTag which was in vivo biotinylated by the endogenous BirA—from the host and M13K07 wt. The result clearly showed a specific SA capture, whereas the M13K07 (SEQ ID NO: 31) did not bind. Thus, the AviTag-pVII fusion must indeed be functional in the sense that it both accommodate to the virion as wt pVII, whereas the N-terminal AviTag is accessible to the BirA enzyme and is recognized as a substrate for biotinlylation (FIG. 4).

FLAG-Tag

ELISA assays were performed to show the accessibility of the FLAG-tag as a pVII fusion in M13K07 (SEQ ID NO: 31) by capturing of phages by two anti FLAG antibodies, M2 and M5. In the assay wildtype M13K07, M13K07-His and M13K07-AviTag were included (FIG. 5).

His-Tag

Both M13k07-HIS6 and VCSM13-HIS6 were tested for specific binding to DynalTalon Beads (IMAC matrix). Briefly, Talon Beads were blocked by incubation with 2% BSA for 30 minutes with rotation. The beads were washed and added 250 μl of titer matched BSA-blocked phage supernatant (corresponding to $2\times10^{10}$ cfukanR/ml) and further incubated for 30 min/RT on a rotating wheel. After washing the beads in PBST, anti-M13 MAb-HRP (diluted 1:2000) was added to each tube and the tubes were further incubated for 45 min/RT on a rotating wheel. After washing, ABTS was added to each tube and incubated 15 min RT, before placing in the magnet rack. 100 μl volumes of each solution transferred to Maxisorp ELISA strips. The absorbance was measured at A405 nm using a TECAN ELISA reader apparatus. The result is truly indicative that the HIS6-pVII containing virions are preferentially bound to Ni-NTA magnetic beads. Despite the low signals, which can be overcome by assay optimalisation, there is indeed a differential binding of the cognate virions to the Ni-NTA matrix. Of the most attractive applications of this particular pVII fusion is the possibility to exploit it for Ni-NTA purification in combinations with e.g. spin columns, as well as site-specific, and thus homogenous directional immobilization to the Ni-NTA matrixes (FIG. 6).

Example 2

Functionality of Modified Helper Phages in Packaging of Phagemids

The promise of the invention is the use the modified helper phages for functional packaging of phagemids displaying a folded domain on a phage coat protein other than pVII, preferably in pIII or pVIII. The following examples support that modified helperphages with different peptides fused to pVII are able to perform functional phagemid packaging and that these phagemids display both functional pVII peptide fusion as well as functional folded domains fused to their pIII coat-proteins. In this manner the examples also serve for bispecific display using phagemids.

Reagents

All media and buffers were prepared essentially as described in Sambrook et al (Molecular cloning: a laboratory manual (Cold Spring Harbor Laboratory Press)). The anti-M13-HRP antibody and the M2 and M5 antibodies were purchased from GE Healthcare Bio-Sciences AB (Uppsala, Sweden) and Sigma-Aldrich (Oslo, Norway), respectively, whereas the F23.2 and GB113 antibodies were a kind gift from Professor B. Bogen (Institute of Immunology, University of Oslo, Norway).

Dynabeads MyOne™-Streptavidin magnetic beads were purchased from Invitrogen (Oslo, Norway). BSA and Tween 20 was purchased form Sigma-Aldrich (Oslo, Norway). The hapten 2-phenyloxazol-5-one (phOx) conjugated to BSA was prepared essentially as described elsewhere (Makela et al, PMID; 722243).

Bacterial Strains, Phage and Phagemids

The *E. coli* strain XL1-Blue was purchased from Stratagene (LaJolla, Calif., USA). M13K07 helper phage was purchased from GE Healthcare Bio-Sciences AB (Uppsala, Sweden). The pSEX81 (SEQ ID NO:29), phagemid harbouring a scFv with specificity against 2-phenyloxazol-5-one (phOx) coupled to bovine serum albumin (BSA) were kindly provided by Affitech AS (Oslo, Norway). The pFKPDN-scTCR Vαβ4B2A1 is described in (Loset et al 2007, PMID: 17925331) (SEQ ID NO:28).

Preparation of Phage Particles

Phagemid rescue from *E. coli* XL1-Blue using M13K07 helper phages and virion assembly was monitored by spot titration as described (Welschof et al, PMID: 9050877 and Koch et al, PMID: 11126120).

Phage-Capture Enzyme Linked Immunosorbent Assays (ELISAs)

MAb M2, M5, F23.2, GB113, phOx-BSA were absorbed to MaxiSorp™ microtiter plate wells (Nunc, Roskilde, Denmark) in concentrations from 2.5 to 5 mg/ml in PBS, pH 7.4 overnight at 4° C. The wells were blocked with 2% skim milk, or 2% BSA in PBS (w/v) for 1 h at RT, virion preparations where then added and allowed to react for 1 to 2 h at RT before captured virions were detected with anti-M13-HRP (1:5,000), for 1 h at RT. Between each step, the wells were washed 3× with PBST. The wells were developed with ABTS substrate and the absorbance read at A405 nm after 30 min Results:

A—Packaging and Titration of Phagemids by Modified M13K07.

Two phagemids with different folded domains were employed, pFKPDNscTCR Vαβ4B2A1 and pSEX-scFv anti-phOx, displaying a scTcR and a scFv as pIII fusion, respectively. Both were packaged with three modified and wt M13K07 helperphages. Briefly, overnight cultures of the two phagemid clones were infected with modified and wt helperphages. After incubation, the culture were centrifuged and the bacterial pellet was resuspended in YT-medium with ampicillin and kanamycine and further incubated ON at 30° C. Cleared supernatants by centrifugation were used downstream. *E. coli* XL-1 Blue was infected with dilutions of phages and plated on ampicillin and kanamycin plates for the titration of phagemids and helperphages, respectively. (FIG. 7).

Both packaged phagemids show high ratios, indicating successful and functional packaging by all three modified M13K07 helper phage formats.

B—Functionality of pVII Donated by Helper Phage in Phagemid pIII Display:

pVII-Avitag display: With respect to AviTag-pVII functionality, SA capture on beads was conducted essentially as described in example 1. Though the signals are low, there is indeed a specific differential capture of the AviTag-pVII containing virions (FIG. 8). As compared with the positive control (insert), it is clear that the level of biotinylation is lower on the phagemid virions than on the M13K07 virions when both harbour the AviTag-pVII fusion. However, it is known that endogenous AviTag biotinylation in the context of phage is only in the range of 7% at 37° C. (Scolle et al PMID: 16628754). Whereas the M13K07-AviTag indeed is packaged at 37° C., the phagemid rescue is done at only 30° C., which strongly suggests that the difference observed is due to lower endogenous BirA activity per see at the lower temperature. Hence, for future use the virion biotinylation efficiency must be increased to exploit this feature. This can conveniently be done by in vitro biotinylation of the virions, which should render close to 100% biotinylation using standard techniques (Scolle et al PMID: 16628754). Alternatively, one can do in vivo biotinylation by over-expressing the BirA enzyme. It is known that by super-transforming *E. coli* such that more than the phagemid or phage genome vector are in the same cell may lead to the packaging of the by standard plasmid into the virion and hence leading to loss of the genotype-phenotype linkage. This would be the case if the BirA was overexpressed from a plasmid. For single clone evaluation this may be acceptable, but when combining the approach with combinatorial repertoires this is unacceptable as it might lead to loss of phenotypic variants retrieved during panning. Alternatively, the BirA can be over-expressed from a chromosomal integration as offered by the *E. coli* MC1061-derived AVB100 strain (Avidity, Colo., USA). This strain is however lacking the F plasmid encoding the F pili structure indispensable for the phagemid system. AVB100 is however directly compatible with phage genome-based vectors, which do not need to be helper phage complemented. To adopt the AVB100 strain to also suit phagemid-based phage display in combination with the modified M13K07 helper phage, we therefore mated AVB100 with XL1-Blue by standard conjugation (example 5).

pVII-Flag Display:

30 ELISA assays were performed to show the accessibility of the FLAG-tag as a pVII fusion in two different phagemids-derived virions, pFKPDNscTCR Vαβ4B2A1 (FIG. 9A) and pSEX-scFv anti-phOx (FIG. 9B), by capturing of phagemid virions by two anti FLAG antibodies, M2 and M5. Briefly, Antibodies were coated on ELISA plates ON at 4° C. The plates were washed and phagemid preparations were incubated on the plates for 2 hours at room temperature. The plates were washed and further incubated with anti-M13 HRP conjugated antibody. The signals were developed after washing of the plates adding ABTS soluble and incubation at RT/30 min (FIG. 9).

FLAG-specific reactivity is obtained for the phagemid-derived virions packaged with the M13K07-FLAG, whereas all other samples are negative. I.e the packaged phagemid-derived virions display the FLAG tag as a functional pVII-fusion.

A. Functionality of pIII Phagemid Display.

Two different phagemid-derived virions, pFKPDNscTCR Vαβ4B2A1 and pSEX-scFv anti-phOx, both displaying Avi-Tag (FIG. 10), FLAG-tag (FIG. 11) and HIS6-tag (FIG. 11) were assayed for functional display of the scTcR and scFv pIII-fusion, respectively.

ELISA assays were performed by capturing of phagemid virions by their specific targets, MAB GB113 which binds scTCR and phOx-BSA for the scFv anti-phOx (SEQ ID NO:26). BSA was used as block and phagemids rescued by wt M13K07 was used as a control. Briefly, targets were coated on ELISA plates ON at 4° C. The plates were washed and phagemid preparations were incubated on the plates for 2 hours at room temperature. The plates were washed and further incubated with anti-M13 HRP conjugated antibody. The signals was developed with ABTS and incubation at RT/30 min, followed by measuring the absorbance at A405 nm (FIGS. 10 and 11).

The results show that cognate Ag-reactivity is obtained for all packaged phagemids. This analysis thus confirms that the modified helper phages do not affect the pIII display, but merely donates a defined phenotype to the pVII protein on the very same virion.

Example 3

Genomic Phage Display on pIII and pVII

The invention allows for the generation of a genomic phage vector with display properties on pVII coatproteins. Such display will not affect the infectivity of virions like pIII display. Furthermore, the invention fosters bispecific display on pVII and pIII/pVIII, or even all three coat proteins simultaneously. The following example supports bispecific display on pIII and pVII in a genomic phage display system showing that the construct behave completely like wildtype phages with respect to propagation, virion assembly, viron concentration, pIII display phenotype and that it indeed is selectively in vivo biotinylated at the pVII peptide fusion.

Reagents

All media and buffers were prepared essentially as described in Sambrook et al (Molecular cloning: a laboratory manual (Cold Spring Harbor Laboratory Press)). The anti-M13-HRP antibody was purchased from GE Healthcare Bio-Sciences AB (Uppsala, Sweden) and the F23.2 and GB 113 antibodies were a kind gift from Professor B. Bogen (Institute of Immunology, University of Oslo, Norway). Restriction enzymes (RE) were purchased from New England Biolabs (Ipswich, Mass., USA) with the exception of DpnI, which was obtained from Stratagene (LaJolla, Calif., USA). DNA oligos were purchased from MWG Biotech AG (Ebersberg, Germany). Dynabeads MyOne™-Streptavidin magnetic beads were purchased from Invitrogen (Oslo, Norway). dm5CTP was from Fermentas (Burlington, Canada) BSA and Tween 20 was purchased form Sigma-Aldrich (Oslo, Norway). Pfu Turbo DNA and Phusion DNA polymerases were purchased from Stratagene (LaJolla, Calif., USA) and Sigma-Aldrich (Oslo, Norway), respectively. The QIAquick PCR clean-up kit was from Qiagen (Qiagen, Hilden, Germany).

Bacterial Strains, Phage and Phagemids

The *E. coli* strain XL1-Blue was purchased from Stratagene (LaJolla, Calif., USA), whereas the *E. coli* strains MC1061 and K91K were kind gifts form Dr G. P. Smith (Division of Biological Sciences, University of Missouri, USA) The pSEX81 (SEQ ID NO:29) phagemid harbouring a scFv with specificity against 2 phenyloxazol-5-one (phOx) coupled to bovine serum albumin (BSA) were kindly provided by Affitech AS (Oslo, Norway). The fUSE5-scTCR Vαβ4B2A1 pIII display vector is described in (Loset et al 2007, PMID: 17925331).

Design and In Vitro Mutagenesis of AviTag™-pVII

The open reading frame (ORF) of the AviTag™ (N-MS-GLNDIFEAQKIEWHE-C; SEQ ID NO:4) was compared to the codon usage in *E. coli* K12 strains using the GCUA server (see the website having the URL "gcua.schoedl.de/seqoverall.html"). A prokaryotic codon-optimized version of the AviTag™ peptide sequence was attached N-terminally to the pVII ORF by QuikChange™ in vitro mutagenesis according to the manufacturers' protocol (Stratagen, LaJolla, Calif., USA), using the primer pair BirA-pVII_frwd/BirA-pVII_rev (5'-CCGGCTAAGTAACATGTCCGGCCTGAACGATATCTTTGAA GCGCAGAAAATTGAATGGCATGAAATGGAGCAGGTC-'3/5'-GACCTGCT CCATTTCATGCCATTCAATTTTCTGCGCTTCAAAGATATCGTTCAGGC CGGACATGTTACTTAGCCGG-3') (SEQ ID NO:5 and SEQ ID NO:6, respectively). To ensure a clean vector background, a BsrGI/SnaBI RE fragment containing the modified pVII was cloned into an unmodified fUSE5-scTCR Vαβ4B2A1 genome on compatible RE sites using standard techniques. The DNA construct was introduced into *E. coli* MC1061 by electroporation. Primer design was based on the published fUSE5 sequence (GenBank accession no.: AF218364) (SEQ ID NO: 30).

Construction of the novel genomic pVII display vectors pGVII and pGVIIΔL

Primer design and vector assembly was done essentially as described in the SeamLess protocol (Stratagene, LaJolla, Calif., USA). Using VCSM13 genome DNA (SEQ ID NO: 32) as template and the primer pair VCSM13_F/VCSM13_R (5'-ATCTCTTCCATGGAGCAGGTCGCGGATTTCGACACAATTTATCAGG-3'/5'-ATCTCTTCCATGTTACTTAGCCGGAACGAGGCGCAGAC-3') (SEQ ID NO:19 and SEQ ID NO: 20, respectively), the complete genome was PCR amplified with Pfu Turbo polymerase essentially as described in the SeamLess protocol (Stratagene, LaJolla, Calif., USA). Likewise, pSEX81ΔL (the latter described in Example 4), and pSEX81 (SEQ ID NO:29) both harbouring a scFv anti-phOx (SEQ ID NO:26) unit, were used as template in a standard PCR using Phusion DNA polymerase (Sigma, Oslo, Normay) with the primer pairs pGALDL_F/pGAL_R (5'-TCTCTTCACATGGCCCAGGTGCAGCTGGTGCAG-3'/5'-ATCTCTTCCCATTCTGATATCTTTGGATCCAGCGGCCGCAC-3') (SEQ ID NO: 22 and SEQ ID NO: 23, respectively) and pGAL_F/pGAL_R (5'-ATCTCTTCACATGAAATA CCTATTGCCTACGGCAGCCGCTGGC-3'/5'-ATCTCTTCCCATTCTGATAT CTTTGGATCCAGCGGCCGCAC-3')) (SEQ ID NO: 21 and SEQ ID NO: 23, respectively), respectively, to amplify the scFv units. Following PCR, all three segments were purified by a PCR clean up kit (Qiagen, GmbH, Hilden, Germany) and RE digested with EarI. RE digested, gel purified segments were then ligated and electroporated into XL1-Blue using standard techniques. Colonies were expanded and verified for correct insert size by PCR screening in a standard PCR using the primer pair pVII_frwd/pVII_rev (5'-AGCAGCTTTGTTACGTTGATTTGG-3'/5'-GCAGCGAAAGACAGCATCG-3') (SEQ ID NO: 24 and SEQ ID NO: 25, respectively). The genomic pVII display vectors were denoted pGVII (having signal sequence-dependent scFv-pVII display) and pGVIIΔL (having scFv-pVII display without any signal sequence). These now contain the scFv ORF as an in-frame fusion N-terminal to pVII and preserving the correct positioning of its start codon to the upstream pV ORF important for normal transcription and translation. Notably, the assembly of these phage genome vectors can just as easily be made by a three step PCR assembly where the exogenous ORF is PCR amplified with 5'-primer tag overhangs complementary to the vector backbone, which can be spliced by PCR SOEing with complementary segments amplified from the 5'- and 3'-portion of the vector covering the site of insertion. An ideal portion of the phage genome should cover a segment including the two unique RE sites BsrGI/SnaBI that are found flanking the pVII ORF in all Ff genomes. RE digested SOEing product can then conveniently be inserted into a complementary RE digested vector backbone, as describe e.g. in Example 1 and 3. Another convenient assembly avenue would be to make an artificial gene assembly of the appropriate fusion ORF completely by short overlapping oligonucleotides that may be annealed as one pot, ligated and PCR amplified by flanking primers. This strategy could render an identical fragment as in the SOEing approach, or be RE independent on which insertion into the phage genome could be based e.g. on recombination as described (Tillett and Neilan, PMID:10481038). A blend of the techniques may also easily be envisioned.

Preparation of Phage Particles fUSE5 phages were amplified from *E. coli* MC1061 essentially as described (Scott and Smith, PMID: 1696028). Virion assembly was monitored by spot titration as described (Scott and Smith, PMID: 1696028 and Koch et al, PMID: 11126120). Where applicable, virions were purified and concentrated by PEG/NaCl precipitation as described (Sambrook et al (Molecular cloning: a laboratory manual (Cold Spring Harbor Laboratory Press)).

Phage-Capture Enzyme Linked Immunosorbent Assays (ELISAs)

F23.2, GB113 antibodies were absorbed to MaxiSorp™ microtiter plate wells (Nunc, Roskilde, Denmark) in concentrations from 2.5 to 5 mg/ml in PBS, pH 7.4 overnight at 4° C. The wells were blocked with 2% skim milk in PBS (w/v) for 1 h at RT, virion preparations where then added and allowed to react for 1 to 2 h at RT before captured virions were detected with anti-M13-HRP (1:5,000) for 1 h at RT. Between each step, the wells were washed 3× with PBST. The wells were developed with ABTS substrate and the absorbance read at A405 nm after 30 min.

A—Titration of fUSE5-scTCR-Avitag Genomic Phages

Neither the wt, nor the pVII-modified fUSE5-scTCR Vαβ4B2A1 versions exhibit any host toxicity. There is no phenotypic difference between the pVII-modified fUSE5-scTCR Vαβ4B2A1 versions regarding virion production and PEG precipitation efficiency. Both the pVII-modified fUSE5-scTCR Vαβ4B2A1 versions yield close to maximum theoretical titers feasible with the fUSE5 system (FIG. 12).

B—Functionality of fUSE5-VII-AviTag Fusion Peptide

This ELISA analysis is to test the functionality of genomic phage preparations by capturing virions by streptavidin beads followed by detection of bound phages by anti M13-Antibodies. Briefly, MyOne Streptavidin dynabeads were blocked with BSA, washed and incubated with titer-normalised samples of fUSE5 phages with (scTCR/pVII-AviTag) and without (scTCR/pVII) pVII-Avitag fusionpeptides. Beads were washed and bound phages were detected with anti-M13-HRP conjugated antibodies. Signal was developed by addition of ABTS and measured at A405 nm using a TECAN ELISA reader apparatus. The results show that the pVII-BirA peptide is accessible and has been biotinylated, and thus serves as an immobilisation and detection tag for phage genome-derived virions (FIG. 13).

C—Functionality of fUSE5-scTCR pIII-Fusion

This ELISA analysis is to test the pIII fusion functionality of phage genomederived virion preparations with and without genome-encoded AviTag-pVII. ELISA assays were performed by capturing of phage virions by two different antibodies recognising the scTCR Vαβ4B2A1) (SEQ ID NO: 28); MAB GB 113 and F23.2, respectively. Skimmed milk was used as negative control. Briefly, antibodies were coated on ELISA plates ON at 4° C. The plates were washed and phage titer normalised preparations were incubated on the plates for 2 hours at room temperature. The plates were washed and further incubated with anti-M13 HRP conjugated antibody followed by the addition of 100 μl ABTS and incubation at RT. The absorbance was measured after 20 min at OD405 nm using a TECAN ELISA reader apparatus. The result shows that the scTCR phenotype is indistinguishable between the two fUSE5 versions. Hence, the pVII modification does not appear to affect the phenotype of the phage in any respect (FIG. 14).

Example 4

Phagemid Display on pVII

Reagents

All media and buffers were prepared essentially as described in Sambrook et al (Molecular cloning: a laboratory manual (Cold Spring Harbor Laboratory Press)). The anti-M13-HRP antibody was purchased from GE Healthcare Bio-Sciences AB (Uppsala, Sweden) and the GB113 antibody was a kind gift from Professor B. Bogen (Institute of Immunology, University of Oslo, Norway). Restriction enzymes (RE) were purchased from New England Biolabs (Ipswich, Mass., USA) with the exception of DpnI, which was obtained from Stratagene (LaJolla, Calif., USA). DNA oligos were purchased from MWG Biotech AG (Ebersberg, Germany). BSA and Tween 20 was purchased form Sigma-Aldrich (Oslo, Norway). Pfu Turbo DNA polymerase was purchased from Stratagene (LaJolla, Calif., USA). The haptens 2-phenyloxazol-5-one phOx and 5-nitrophenacetyl (NIP) conjugated to BSA were prepared essentially as described elsewhere (Makela et al, PMID; 722243 and Michaelsen et al, PMID: 2125362). Isopropyl-beta-D-thiogalactopyranoside (IPTG) was purchased from Fermentas (Burlington, Canada).

Bacterial Strains, Phage and Phagemids

The *E. coli* strain XL1-Blue was purchased from Stratagene (LaJolla, Calif., USA). M13K07 helper phage was purchased from GE Healthcare Bio-Sciences AB (Uppsala, Sweden). The pSEX81 (SEQ ID NO:29) phagemid harbouring a scFv with specificity against 2-phenyloxazol-5-one (phOx) coupled to bovine serum albumin (BSA) was kindly provided by Affitech AS (Oslo, Norway). The pFKPDNscTCRVαβ4B2A1 pIII display phagemid has been described elsewhere (Loset et al 2007, PMID: 17925331). The prokaryotic expression vector pSG1 harbouring the scFv anti-NIP (SEQ ID NO: 27) (unpublished) is based on pHOG21 (Kiprianov et al, PMID: 9005945) and has been made in-house from the antibody variable genes derived from pLNOH2 and pLNOK (Norderhaug et al, PMID: 9202712).

Construction of the Novel pVII Display Phagemid Vectors pGALD7 and pGALD7ΔL

As a starting template for the vector backbone, the pSEX81 (SEQ ID NO:29) phagemid described above was chosen (GenBank accession no.: Y14584). Firstly, to remove the prokaryotic pelB signal sequence (N-MKYLLPTAAA-GLLLLAAQPA MAC) (SEQ ID NO:33) encoding stretch in this vector, a NcoI RE site was introduced in the extreme N-terminus by QuikChange™ in vitro mutagenesis using the primer pair a41g-frwd/a41g-rev (5'-AGAGGAGAAAT-TAACCATGGAAT ACCTATTGCCTACGGC-3'/5-GCCG-TAGGCAATAGGTATTCCATGGT TAATTTCTCCTCT-3') (SEQ ID NO:13 and SEQ ID NO: 14, respectively), thereby changing the first nucleotide in the second codon of the pelB ORF from A to G. Following mutagenesis, the vector was NcoI digested, re-ligated and used as template in a second PCR retrieving the relevant part of the vector using the primer pair pHOG_EcoRI_frwd/scTCR_rev (5'-TAGCTCACT-CATTAGGCACCC-3'/5'-TTTGGATCCAGCGGCCGC-3') (SEQ ID NO:15 and SEQ ID NO: 16, respectively). This PCR fragment was then moved into the original pSEX81 (SEQ ID NO:29) on the compatible EcoRI/HindIII RE sites using standard techniques and confirmed by DNA sequencing. This step completely removed the pelB signal sequence encoding portion, but preserved the start codon and its relative position towards the lacPO and Shine-Dalgarno sequence (SD) important for normal transcription and translation, as well as adding only one Ala residue before the exogenous sequence defined by the NcoI/NotI RE sites found in the original pSEX81 (SEQ ID NO:29). The new construct was denoted pSEX81ΔL. Secondly, the pVII encoding sequence was amplified from M13K07 using the 5'-end RE-tagged primer pair pVII_EcoRV/pVII_NheI (5'-ATATGATATCAGAATGGAG CAGGTCGCGGATTTCG-3'/5'-ATATGCTAGCTTAT-CATCTTTGACCCC CAGCGATTATACC-3') (SEQ ID NO:17 and SEQ ID NO: 18, respectively). This PCR fragment was then moved into both the pSEX81 (SEQ ID NO:29), and pSEX81ΔL phagemids on the compatible RE sites, thereby exchanging the pIII encoding region in both and resulting in a N-terminal in frame pVII fusion of the NcoI/NotI-defined cassette in the original pSEX81 (SEQ ID NO:29). The new constructs were confirmed by DNA sequencing and denoted pGALD7 and pGALD7ΔL, respectively. To switch the scFv anti-phOx (SEQ ID NO:26) unit in the various phagemids described above, with the scTCR Vαβ4B2A1 and scFv anti-NIP (SEQ ID NO: 27) units from pFKPDN and pSG1, respectively, this was done as NcoI/NotI RE defined cassette exchange using standard techniques. All phagemids described herein were introduced into *E. coli* XL1-Blue by electroporation using standard techniques.

Preparation of Phage Particles

Phagemid rescue from *E. coli* XL1-Blue using M13K07 helper phages and virion assembly was monitored by spot titration as described (Welschof et al, PMID: 9050877 and Koch et al, PMID: 11126120).

Phage-Capture Enzyme Linked Immunosorbent Assays (ELISAs)

MAb GB113, phOx-BSA or NIP-BSA were absorbed to MaxiSorp™ microtiter plate wells (Nunc, Roskilde, Denmark) in concentrations from 2.5 to 5 mg/ml in PBS, pH 7.4 overnight at 4° C. The wells were blocked with 2% skim milk, or 2% BSA in PBS (w/v) for 1 h at RT, virion preparations where then added and allowed to react for 1 to 2 h at RT before captured virions were detected with anti-M13-HRP (1:5,000) for 1 h at RT. Between each step, the wells were washed 3× with PBST. The wells were developed with ABTS substrate and the absorbance read at A405 nm after 30 min.

Results

Prompted by the results from the modified helper phages described above, pVII display of folded domains was also assessed. As both Gao et al and Kwasnikowski et al have shown that such display is allowed when used in combination with signal sequence-directed periplasmic targeting, we constructed two novel phagemids termed pGALD7 and pGALD7ΔL, allowing for N-terminal pVII display with and without such a signal sequence, respectively (FIG. 15).

The initial constructs contained a scFv unit based on human antibody variable segments and being specific for the hapten conjugate phOx-BSA. As with the pVII modified helper phages described previously, pVII display of the scFv should not interfere with normal virion assembly. We therefore compared the performance of these scFv anti-phOx pVII display phagemids with and without signal sequence and also with standard pIII display with and without signal sequence, using standard phagemid rescue and titration as described in materials and methods. (FIG. 16)

The titration result indeed showed that phagemid-containing virions were made in all cases. However, whereas the pVIIΔL phagemid yielded titers about 30-fold lower than standard pIII display, there was a gross $10^5$-fold reduction in the signal sequence-directed pVII display. As wt complementation of pVII is present from the helper phage in this system, this finding was both surprising and important, because it shows that the signal sequence-directed pVII display (pVII) severely interferes with the virion assembly process, whereas this effect is only minor in the case with signal sequence-less pVII display ($pVII^{\Delta L}$). In comparison, the titer difference between pIII display with and without signal sequence, was only minor.

Based upon the titers determined above, we then assessed the functional scFv display on these virion samples in a phOx-BSA specific ELISA using titer normalized inputs, except for the pGALD7-derived sample that was used undiluted as the phagemid titer was very low. (FIG. 17).

The result clearly showed functional scFv display from both the signal sequenceless pVII version and standard pIII, whereas the other samples were negative. That the signal sequence-directed pVII display yielded negative results was expected due to the 2000-fold less virion input. It is known that pIII is exported to the periplasm through the SEC-pathway, hence the signal sequence-less pIII version yields pIII fusions defect in periplasmic targeting, which is a prerequisite for virion incorporation. The virions from this sample, hence contains only helper phage derived pIII (loss of physical phenotype-genotype linkage), though the phagemid packaging efficiency is close to normal and results in normal titers (as seen in FIG. 16. Though both signal sequence-less pVII version and standard pIII display yielded functional display, it is clear that the antigen binding ability appears stronger with pIII. This does not necessarily reflect a higher functionality of the pIII version, as it is well documented that standard pIII display renders a mixture of mono- to oligovalent display of scFv units causing avidity effects (Bradbury and Marks, PMID: 15261570). Such effects are masking the true inherent affinity of the interaction, and though the scFv unit is often preferred due to superior expression profile, it is extensively documented that e.g. the lower expressed Fab format, in the meaning of less units per virion, results in much stronger binders upon affinity selection (de Haard, et al, PMID: 10373423 and Hoogenboom, PMID: 16151404). It could therefore be that the lower signal from the pGALD7ΔL rather reflects a closer to monovalent scFv display, which for many applications could be advantageous.

The scFv-pVII/pIII expression cassette in all the phagemids employed here are controlled by the lac promoter and the virion packaging was done using the standard protocol without IPTG induction (Welschof et al, PMID: 9050877), Thus, it should be possible to increase the scFv display by forcing stronger expression using IPTG during packaging. Moreover, an important feature of phagemid phage display is the fact that functional display is dependent upon helper phage mediated rescue of the phagemid. Therefore, in contrast to phage genome-based display, there are two sources of ssDNA that can be packaged into the virion from a given cell—the phagemid, or the helper phage genome. Importantly, both types of virions will have access to the very same pool of capsid proteins, as they are produced and found within the very same host cell. To ensure the preservation of the physical genotype phenotype linkage that forms the very basis for combinatorial phage display technology, it is therefore of the out most importance that the phagemid-to-helper phage ratio is in favour of the phagemid. In a new experiment, we prepared the same phagemid-derived samples as described above, but now also comparing virion assembly with and with out IPTG included during packaging. During titration, we this time also mapped the helper phage genome titers by means of the kanamycin resistance found on the helper phage genome.

The current titration result (FIG. 18A) exhibited the very same trend as in the former packaging (FIG. 16), with respect to phagemid titers when comparing the different phagemids at standard conditions, but this time both the pGALD7ΔL ($pVII^{\Delta L}$) and the pGALD7 (pVII) had somewhat higher titers. Upon IPTG induction of the pVII, or pIII expression all phagemids exhibit a reduction in titer, but the effect is the most severe for the sequence signal-directed pVII pGALD7 phagemid.

When mapping the phagemid-to-helper phage ratios (FIG. 18B) and comparing the different phagemids under standard conditions (without IPTG present), all samples exhibit ratios in the normal range and in favour of the phagemid, except for the sequence signal-directed pVII pGALD7 phagemid, which exhibits a complete loss of the phenotype-genotype linkage. Upon IPTG induction, the uncoupling of the phenotype-genotype was even more pronounced for the pGALD7 phagemid, and now also the signal sequence-less pIII ($pIII^{\Delta L}$) exhibited this feature to a small extent (ratio 0.5). However, the latter construct is nevertheless non-functional with respect to pIII display and was only included as control.

Based upon the phagemid titers shown in FIG. 18A, we then assessed the functional scFv display of the pGALD7ΔL and pGALD7 virions in a phOx-BSA specific ELISA similar to that shown in FIG. 17. Using normalized titer inputs.

The result did indeed show the functional scFv-pVII display was again achieved with the signal sequence-less pGALD7ΔL and the phOx-BSA reactivity increased significantly upon IPTG-forced pVII fusion expression. This increase in antigen reactivity most likely reflects an increased number of pVII fusion per virion as well as an increased number of virions harbouring a pVII fusion per see. The latter is likely as it is known that in standard pIII display only between 1 to 10% of the phagemid-containing virions actually contains a fusion (Bradbury and Marks, PMID: 15261570). On the other hand, the signal sequence-directed pVII display again showed no functional phOx-BSA binding. Based on FIG. 18B, the weak antigen reactivity observed in the IPTG uninduced sample, must be assigned to helper phage containing virions harbouring the pVII fusion at low level.

So far, we have clearly shown functional pVII phagemid-based display of the scFv anti-phOx (SEQ ID NO:26), unit and that this construct is comparable to pIII display of the same scFv, exhibiting only a minor reduction in phagemid titers and in antigen binding capacity.

The scFv anti-phOx (SEQ ID NO:26) has been selected for a human antibody scFv library and is known to express rather well in *E. coli* (Marks et al., PMID: 1748994). To see whether or not pVII display exhibits the capacity to functional display of more challenging fusion partners, we therefore subcloned a scFv anti-NIP (SEQ ID NO: 27) based on the antibody variable genes of a murine hybridoma, as well as a scTCR based on the variable genes from the murine T cell clone 4B2A1 (Loset et al, PMID: 17925331) into both pGALD7DL and pGALD7. It is well known that many hybridoma variable genes do not express well in *E. coli* and also when phage displayed (Krebber et al, PMID: 9032408) and T cell receptors are a class of folded proteins that has proven especially difficult to accommodate to phage display (Li et al, PMID: 15723046, and Loset et al, PMID: 17925331).

Virions from these new phagemids were prepared by standard phagemid rescue and tested for their antigen binding capacity in ELISA (FIG. 20).

The result did indeed show that functional pVII display was achieved both with the scFv anti-NIP (SEQ ID NO: 27) and the scTCR Vαβ4B2A1 and in contrast to the what was observed previously with the scFv anti-phOx (SEQ ID NO:26), this was the case both with and without signal sequence-directed pVII display. The signals observed in FIG. 20 are not directly compared though as virion titers were not normalized before the assay. In light of the complete non-functional nature of the signal sequence-directed pVII display of the scFv anti-phOx (SEQ ID NO:26), the samples above were titrated and the phagemid-to-helper phage ratios determined (FIG. 21).

The phagemid titers again showed that the signal sequence-less pVII display (pGALD7ΔL) exhibited superior performance as compared with signal sequence directed pVII display (FIG. 21A). This was indeed true for both the scTCR and the scFv anti-NIP, but the difference was less obvious than with the titers observed for the scFv anti-phOx (see FIGS. 6 and 8). When comparing the phagemid-to-helper phage ratios, the pGALD7ΔL again showed excellent performance with ratios in strong favor of the phagemid both in the case of the scTCR and the scFv anti-NIP (SEQ ID NO: 27) (FIG. 21B). The severe loss of the genotype-phenotype linkage seen with the scFv anti-phOx (SEQ ID NO:26) was not observed for the scTCR and the scFv anti-NIP (SEQ ID NO:27), from these ratios (FIG. 18 versus FIG. 21B). However, the pGALD7ΔL was clearly superior.

In light of the results above, it was noteworthy the see that there was a quite distinct difference between the scTCR and scFv anti-NIP with respect to host cell proliferation during virion packaging (FIG. 22).

What is evident from FIG. 22 is that whereas the pGALD7ΔL containing cultures only have a minor effect on host cell proliferation, the growth is significantly inhibited by the clones containing the pGALD7 phagemid. This is strongly indicative of host toxicity from the signal sequence-directed pVII display phagemid, whereas no or little such toxicity is observed as soon as the signal sequence is removed.

Example 5

Construction of the *E. coli* strain AVB100FmkII

Reagents and Bacterial Strain

All media and buffers were prepared essentially as described in Sambrook et al (Molecular cloning: a laboratory manual (Cold Spring Harbor Laboratory Press)). The *E. coli* strains XL1-Blue and AVB100 (based on MC1061) were purchased from Stratagene (LaJolla, Calif., USA) and Avidity (Denver, Colo., USA), respectively.

Results

To obtain F plasmid positive *E. coli* AVB100 (chromosomal StrR) the cells were mated with XL1-Blue (F plasmid TetR) as follows. Single colonies of each strain was inoculated into 5 ml LB medium supplemented with the appropriate antibiotic and incubated over night at 37° C. with rigorous shaking. The next day, fresh 5 ml cultures were initiated at an A600 nm of 0.1 and grown to mid log phase at 37° C. with rigorous shaking before 1 ml of each were mixed and incubated stationary at 37° C. for 1 h. Thereafter, 10 μl of this mixture was transferred to 5 ml fresh LB medium containing 100 μg/ml Str and 30 μm/ml Tet and incubated over night at 37° C. with rigorous shaking. The next day, dilutions of this culture was spread on agar dishes containing 100 μm/ml Str and 30 μm/ml Tet and the resulting colonies used as source of the new F plasmid positive AVB100 strain, termed AVB100FmkII.

Example 6

The Construction and Spiking of Anti-GFP and GFP-M13 Phages into Anti-phOx M13 Phages This example illustrates the process of testing how two types of phage populations could interact with each other in the presence of a third negative population. One is a bispecific phage in which GFP (Green fluorescent protein) is attached to the pIII protein and expressed on phage with a biotinylated tag at pVII position. GFP DNA constructs and protein can be purchased from Evrogen (Moscow, Russia) or Clontech (Mountain View, Calif., U.S.A). The second population of phage contains anti-GFP scFv antibody attached to the pIII protein. This, together with the negative anti-phOx phages (4-ethoxymethylene-2-phenyl-2-oxazoline-5-one [Marks, J. D., et al. Biotechnology (NY), 10, 779-783 (1992)], (the third population); is a normal phage without pVII tagging.

The first part of this example illustrates how these phages were made & characterized with the use of ELISA.

Construction of Anti-GFP Normal scFv-pIII Phage and GFP-pIII Bispecific Phage (with a Biotinylated Tag at pVII).

The phages were constructed as outlined in Materials & Methods. The phages were packed as a normal anti-GFP-pIII fusion to M13 phage (using the M13K07 helper phage from Stratagene) or as GFP-pIII fusion with a biotinylated tag at pVII of M13 (biotin labeling with the BirA VCSM13 helper phage).

Western Blot Analysis to Determine GFP-Expression on M13 Phages.

To test the display of GFP and the dependence of their secretion signal sequence in fusion to the geneIII, western blot analysis of the different amplified phages (either packed with M13K07-, Hyper- or BirA-helper phage) was performed (see FIG. 23). Three different formats were available that differed in their signal sequence (sec-pathway or TAT-pathway) at the N-Terminus of the GFP. The sequences are given in Table A.

The bacterial TorA-leader sequence belongs to the twin-arginine-transport system. This transport system is described to move folded proteins over membranes [Sargent F. Biochemical Society of Transactions, Vol. 35, part 5 (2007)]. With the final aim to isolate antigens presented on the phage pIII-surface in a library vs library screen (e.g. antigens vs scFv-library), the display of interesting antigens could fail as they might not get represented on the phage-surface and hence get lost during the selection procedure. This could be circumvented by usage of different signal leader sequences in fusion to the antigens to be presented, e.g. the TorA-leader sequence as well as the DsBA leader sequence which belongs to the signal recognition particle complex (SRP) [Steiner et al Nat. Biotech 24(7); (2006)]. For these reasons, in the initial experiments, the TorA leader sequence was implemented (see Table A) to test if our antigen, the GFP can be represented on the phage in fusion to the pIII (see FIG. 23).

TABLE A

Amino acid sequences of three different secretion leader sequences tested for the expression of GFP in fusion to geneIII.

| Leader sequence | Amino acid sequence |
|---|---|
| TorA7I | MNNNDLFQTSRQRFLAQLGGLTVAGMLGPSLLTPRRATAAMA (SEQ ID NO: 34) |
| TorA7II | MNNNDLFQTSRQRFLAQLGGLTVAGMLGPSLLTPRRATAAQAAMA (SEQ ID NO: 35) |
| pelB | MKYLLPTAAAGLLLLAAQPAMA (SEQ ID NO: 36) |

FIG. 23 shows that the GFP was expressed as fusion to the geneIII. Highest expression was detected if phages were amplified in the presence of either M13- or Hyperphage in fusion to the pelB secretion signal. Most importantly, GFP expression was also observed if phages were amplified in presence of the BirA-helper phage, producing a biotin label at the pVII position. BirA-amplified phages can thus be applied in the initial spiking experiments. Similar results were obtained if GFP was expressed in fusion to the TorA7AII leader sequence; although the expression seems to be lower in comparison to M13-helper phage amplified GFP-phages. No GFP-geneIII fusion was detected in presence of the TorA7AI leader sequence.

Determination of Coupling of BirA-GFP-Phages to Streptavidin Beads by Phage-ELISA We next tested if we can couple the BirA-GFP-phages to streptavidin beads. Coupled phages were detected with an anti-Fd-antibody (rabbit), followed by incubation with an anti-rabbit-HRP-coupled antibody. Serial phage dilutions in 3% BSA were prepared and M13K07 helper phage was included to demonstrate successful coupling to the beads. The results are given in FIG. 24. A slight/low signal can be detected for M13K07 helper phages, which could be due to unspecific binding of the phage particle itself. However this signal is nearly 3- to 4-fold less compared to the measured signal of the BirA-GFP-phage. The results demonstrated that biotin tagged phages can be immobilized onto the streptavidin beads, and thus the BirA helper phage has packaged the GFP-phage with a biotinylated pVII-protein.

The second part of this example describes the phage versus phage panning with the use of a negative phage carrying a scFv against phOx, termed anti-phOx.

Phage Versus Phage Panning—Spiking Libraries

As an initial experiment, it was tested whether an anti-GFP normal scFv-pIII phage can be recovered after incubation with the GFP-pIII bispecific phage (with a biotinylated tag at pVII). Two different scenarios are possible to perform the library vs library screen (see schematic flow in FIG. 25).

1. In scenario I as shown in FIG. 25, the antigen bispecific phage (BirA-GFP-phage) was first immobilized on the streptavidin beads; the second library consists of a normal scFv antibody phage directed against the antigen (anti-GFP-phage) and a third normal negative scFv-phage (anti-phOx phage). These were incubated with the immobilized antigen-phage.
2. In scenario II, all library members (meaning the bispecific antigen-phage (BirA-GFP-phage), normal anti-GFP scFv phage as well as the normal negative scFv phOx-phage) were incubated in solution. Interacting phage pairs (BirA-GFP-phage<->anti-GFP-phage), in addition to non-interacting BirA-GFP-phage, were captured and separated using streptavidin beads and re-isolated after elution (by pH-shift or by proteolytic digestion with e.g. trypsin).

In this manner, scenario II was tested in a first panning round with mild stringency.

Several different set ups of mixtures were tested in parallel:

a.) $10^{10}$ BirA-GFP-phages were mixed with $10^{10}$ anti-GFP-phages (amplified with M13K07 before interaction).

b.) $10^{10}$ BirA-GFP-phages were mixed with $10^{10}$ anti-GFP-phages (amplified with Hyper-phage before interaction). In this case, the higher avidity of the anti-GFP-phage should increase the affinity.

c.) $10^{10}$ BirA-GFP-phages were mixed with $10^{10}$ anti-GFP-phages (amplified with Hyper-phage before interaction) and $10^{10}$ anti-phOx-phages, being a real library test with a ratio of 1:1:1.

d.) $10^{10}$ M13K07-phages (helper phage) were mixed with $10^{10}$ anti-GFP-phages (amplified with M13K07 before interaction), serving as a negative control.

All mixtures were incubated for 1 h at 19° C. on a rotary wheel in the presence of BSA/PBS-Tween 20 (see Methods). Streptavidin beads were next added to the phage-mixtures and incubated for 1 h to pull out interacting phage-pairs or non-interacting BirA-GFP phages, upon coupling of the bispecific BirA-GFP-phages to the streptavidin beads. Only if the GFP-phages interact with the anti-GFP-phage in the mixture, an amplification and recovery of anti-GFP phages after elution of this phage would be possible. The different beads-mixtures were placed on a magnetic holder and washed five times with PBS-Tween 20 to decrease background- or unspecific binding. Alkaline TEA elution was performed and phages were amplified after harvesting from plate (Materials and Methods). Reassuringly, no phages could be recovered from strategy d.) described above, demonstrating the specific coupling of the Bir-A-GFP-phage to the beads as well as no background binding of the phages to the blocked beads. A polyclonal phage-ELISA on coated recombinant GFP was performed to analyze if the anti-GFP-phage can be recovered from the mixture (see FIG. 26).

Anti-GFP-phage specific signals were detected for all three tested settings (a.), (b.) and (c.), see description above). Reassuringly, no specific binding signals were measured on block-only coated wells (4% milk/PBS) for these mixtures as well as for M13K07- and anti-phOx-phages, illustrating the specificity of the tested system.

The ELISA-results demonstrate that it was possible to recover the anti-GFP-phage from solution as outlined in scenario II (see FIG. 25). This suggests that the binding pair (GFP-phage/anti-GFP-phage), interacts in solution and can be isolated by using magnetic strepatvidin beads. However, a decrease in binding signal on coated GFP was detected for the settings (b.) and (c.) (described above). Especially hyper-phage amplified anti-GFP-phages were used to increase the affinity towards the GFP-phage via an avidity effect. Therefore it is possible that interacting phage pairs rebind in solution (after neutralisation) and lower the signal in ELISA against immobilized GFP. This rebinding could also counteract phage amplification upon *E. coli* infection, which fits well with the observation that a lowered signal is detected for the mixture (c.) in which BirA-GFP-phages were mixed with anti-GFP-phages (amplified with Hyper-phages before interaction) and an equal amount of anti-phOx-phages (amplified with M13K07-phages before interaction). The difference in signal could also be explained by different phage-titers in the mixtures of (b.) and (c.), or the anti-GFP-phage has a less effective replication rate, hence leading to growth disadvantage in comparison to the anti-phOx-phage during phage amplification shifting the phage ratios in the amplified phage-solution and lowering the number of anti-GFP-phages.

From these initial spiking experiments, it can be concluded that it is possible to isolate a specific interacting phage (the anti-GFP-phage) using bead separation from a solution mixture. Moreover, higher signals were detected for the mixture (a.), in which the anti-antigen-phage (here anti-GFP-phage) was amplified using M13K07 phages. For these reasons, the following spiking experiments were performed using the same settings (meaning libraries in solutions as described under Scenario II) as well as panning on pre-coupled beads (as described under Scenario I).

Spiking Experiments

Two different ratios of spiking experiments were prepared in parallel. Both $10^7$ BirA-GFP-phages and $10^7$ anti-GFP-phages were mixed in a 1000-fold excess of anti-phOx-phages ($10^{10}$ phages). These combined libraries, each with a complexity of $1\times10^3$ lead to a stringent library with a pooled ratio of $1\times10^6$. Also, scenarios I and II described in FIG. 25 were performed in parallel. In total, 2 panning rounds were carried out using alkaline TEA elution. Enrichment of anti-GFP-phages after panning rounds was evaluated by phage-ELISA experiments on immobilized recombinant GFP (see FIG. 27*a/b*). In parallel, an ELISA was prepared with the aim to detect enrichment of the GFP-phage over 2 panning rounds. Therefore, phages from panning round 1 and 2 as well as P0 were coated to the wells and GFP was detected upon incubation with an anti-GFP-antibody (see Material and Methods). The results are given in FIG. 27*c*).

First of all and most importantly, no significant background binding was detected for the phage-samples from Pan 2 of the negative control (neg.ctrl. Pan 2). Reassuringly, no significant binding to wells coated with block solution only (4% milk) was detected during all measurements (data not shown). The measured signal for P0 in all panning-strategies performed (scenario I and II for $1:10^6$ spiking libraries) was below the signals of samples of Pan 1 and Pan 2. In contrast, an increase in signal intensity was detected for panning round 1 (Pan1) and panning round 2 (Pan2) in all tested libraries. This indicates that the anti-GFP-phage has been enriched successfully.

However, in all cases the phage ELISA curves decrease very steeply with increasing dilutions. The same pattern was also observed in FIG. 26 and may indicate that the number of enriched phages in the samples from the panning rounds is very low or phages having weak interactions. The BirA enzyme is found endogenously in all *E. coli* and biotinylates only ~7% of Avitag tags on phages at 37° C. [Scholle et al, ChemBioChem 7(5), 834-838 (2006)]. This could also explain the lower enrichment observed in FIG. 27. Since ~90% of the bispecific GFP-phages are apparently unbiotinylated, these untagged Avitag-labelled phages can also bind to members of the other anti-GFP phage population and inhibit enrichment of the biotin-tagged phage pair. This could contribute to increase the complexity of the library from $10^6$ to $10^7/10^8$ by lowering the amount of Target pairs that could be captured—making the enrichment less efficient. An obvious improvement could be to use in vitro biotinylation methods to increase the biotinylation efficiency.

As alkaline TEA elution followed by neutralization was used during all panning rounds, it is possible that the interacting phage-pairs (BirA-GFP-phage/anti-GFP-phage) could rebind to each other and may not infect *E. coli* and hence get lost during amplification. Secondly, if GFP-phages are eluted and amplified in parallel to the anti-GFP-phages, these phage-pairs can rebind again during phage amplification (including precipitation and purification). Hence, during ELISA-experiments, it is possible that there is a competition between coated GFP in the wells and free GFP-phages in solution binding to anti-GFP-phages, especially since there is a high expression yield of GFP on the phage, when amplified with M13K07 helper phage (see FIG. 23*a/b*). Indeed, as demonstrated in FIG. 27*c*), a slight enrichment of GFP-phages from P0 to Pan 2 is detectable, but with weak signals. This may be due to the reversed orientation of this ELISA set-up by initially immobilising phages on plastic (FIG. 27*c*) rather than proteins (FIGS. 27*a* & 27*b*), implying a lowered amount of detectable molecules due to their difference in size. To circumvent the elution of "antigen-phages" or re-binding after elution, alternative elution strategies during the panning rounds, e.g. tryptic elution [Løset, et al, Biotechniques 44(4), 551-554 (2008)], could be used which destroys the fused non-phage proteins (antigen/antibodies) but ensure monovalent infection of phage and bacteria In addition, by applying a two step purification where both libraries are bispecific but with different tags, it should be possible to get a better enrichment and a better separation of the different phage library pools. For example TEA can be used to break the antibody-antigen interaction (to dissociate antigen-antibody phages) while a $HIS_6$-tag on one bispecific phage library can be employed to capture and separate it from the other bispecific phage library. Thus, it should be possible to prevent association of the two libraries in solution before assaying them independently.

In addition, the steep decrease of the ELISA curves may be explained by the fact that the anti-GFP-phages have a growth disadvantage in comparison to the anti-phOx-phages spiked into the libraries (as also seen in FIG. 26). Although the anti-phOx-phages do not exhibit any specific binding to the target (GFP), they would still shift the equilibrium in the panning rounds. Most probably, this could be overcome by doing a third or fourth panning round.

To conclude, the data presented demonstrate that it is possible to perform phage vs phage panning and to enrich for specific binders. Further optimization of the methods, for example like the above mentioned improved biotinylation of phages, improved elution strategies and by employing two bispecific libraries (rather then one bispecific and one normal phage library demonstrated here) should ensure even better separation and increased specificity. Furthermore, the detection of enrichment of binders can be monitored by PCR-based methods or by monoclonal phage-ELISA. However, this needs prior knowledge of the type and size of antigen or by inserting PCR recognizable sequences during library construction.

Materials and Methods

Construction of Anti-GFP scFv-pIII Phage

Recombinant GFP with c-terminal $His_6$-tag [Green Fluorescent Protein; ASK GEELFTGVVPILVELDGDVNGH-KFSVSGEGEGDATYGKLTLKFICTTGKLPVPWPTL VTTLTYGVQCFSRYPDHMKRHDFFK-SAMPEGYVQERTISFKDDGNYKTRAEVKFEG DTLVNRIELKGIDFKEDGNILGHKLEY-NYNSHNVYITADKQKNGIKANFKIRHNIEDG SVQLADHYQQNTPIGDGPVLLPDNHYL-STQSALSKDPNEKRDHMVLLEFVTAAGITH GMDE-LYKHHHHHH (SEQ ID NO:37)] was assembled in a plasmid under the control of lac-promoter in TG-1 *E. coli* cells. The GFP protein was induced in the bacteria with 100 μM IPTG (isopropyl-β-D-thiogalactopyranoside) and protein was produced at 37° C. over night. Protein was extracted by sonication on ice and applied to a self-packed Ni-NTA column (SuperFlow slurry, QIAgen), washed extensively using 20 mM of imidazole and eluted in 250 mM imidazole. The eluted protein was further purified by size exclusion chromatography and was dialysed over night into PBS pH7.4 and the concentration was determined by absorbance measurement at A280 nm. Purity of GFP was verified on Commassie stained SDS-PAGE. The purity was estimated to be 90%.

The antibody against GFP was identified after 3 rounds of panning of a normal naïve phage display scFv-pIII library (Løset et al. J. Immunol Methods 299, 47-63 (2005)). In short: Purified GFP was coupled over night to blocked (in 4% (w/v) milk) magnetic Ni-beads (Qiagen) at a concentration of 10 μg/ml. 100 μl of $10^{12}$ Pfu/ml of preabsorbed phages (in 4% (w/v) milk) displaying scFv antibodies fused to pIII were applied to the GFP-coupled Ni-beads in the presence of 4% (w/v) milk in PBS pH7.4 and incubated for 1 h at 19° C. The mixture was washed with increasing stringency using PBS-Tween 20 (0.05% (v/v)) from panning round 1 (5 washes) to panning round 2 (10 washes) to panning round 3 (20 washes). Phages were eluted using Tris-Ethyl-Amine (250 μl of 100 mM TEA for 3 min), followed by neutralization upon addition of 250 μl 1M Tris-HCl pH8.0 to the reaction mix, infected and packaged as described under "Phage elution and infection". Enrichment was verified by polyclonal phage ELISA (see below, Phage ELISA) on immobilized GFP. To identify positive individual candidates, monoclonal phages from panning round 3 were picked from LB-TAG plates and next amplified separately (see phage amplification section below). Binding activity towards GFP was tested in ELISA (see below) and positive clones were sequenced. This lead to the identification of one positive candidate: Anti-GFP-scFv (linker underlined):

```
                                        (SEQ ID NO: 38)
EVQLVESGGGLVQPGRSLRLSCAASGFTFDDYAMHWVRQAPGKGLEWVSA

ISGSGGSTYYADSVKGRFTISRDNSKNTLNLQMNSLRAEDTAVYYCAKGR

YDFWSGGPFDYWGQGTLVTVSSKLSGSASAPKLEEGEFSEARVSSELSQD

PAVSVALGQTVRITCQGDSLRSYYASWYQQKPGQAPVLVIYGKNNRPSGI

PDRFSGSSSGNTASLTITGAQAEDEADYYCNSRDSSGNWVFGGGTKLTVL
```

Cloning of the GFP-Gene in Fusion to geneIII

The GFP gene was amplified via PCR out of the vector pLacIq-pFAb using following primers (NcoI and NotI restriction sites underlined):

```
GFP-fw:
                                   (SEQ ID NO : 39)
5'CCGGCCATGGCGGCTAGTAAAGGAGAAGAACTTTTCACTG

GAGTTGTCCC'3,

GFP-rv:
                                   (SEQ ID NO: 40)
5'CAGCTGCTGGGATTACACATGGCATGGATGAACTATACAAA

GCGG CCGCGGATC C'3.
```

The PCR-product was digested with NcoI/NotI restriction endonuclease enzymes and ligated into the pSEX-vector from which a mock gene was removed using the same enzymes and which includes the peIB-leader signal sequence. Resulting vector was termed pSEX-peIB-GFP and positive clones were confirmed by sequencing. The sequence is given in below. The peIB-leader sequence as well as the NotI restriction site (encoding amino acids) at the C-terminal end is underlined.

pSEX-peIB-GFP:

```
pSEX-pelB-GFP:
                                        (SEQ ID NO: 41)
MKYLLPTAAAGLLLLAAQPAMAASKGEELFTGVVPILVELDGDVNGHKF

SVSGEGEGDATYGKLTLKFICTTGKLPVPWPTLVTTLTYGVQCFSRYPD

HMKRHDFFKSAMPEGYVQERTISFKDDGNYKTRAEVKFEGDTLVNRIEL

KGIDFKEDGNILGHKLEYNYNSHNVYITADKQKNGIKANFKIRHNIEDG

SVQLADHYQQNTPIGDGPVLLPDNHYLSTQSALSKDPNEKRDHMVLLEF

VTAAGITHGMDELYKAAA.
```

Next, the peIB-leader signal sequence was exchanged with either the TorA7I- or the TorA7II-leader sequence (see below). The leader sequences were replaced using XhoI/NotI restriction endonucelases. Resulting vectors were termed pSEX-TorA7I-GFP as well as pSEX-TorA7II-GFP. Positive clones were confirmed by sequencing (see below). The peIB-leader sequence as well as the NotI restriction site (encoding amino acids) at the C-terminal end is underlined.

```
pSEX-TorA7I-GFP:
                                        (SEQ ID NO: 42)
MNNNDLFQTSRORFLAQLGGLTVAGMLGPSLLTPRRATAAMAASKGEELF

TGVVPILVELDGDVNGHKFSVSGEGEGDATYGKLTLKFICTTGKLPVPWP
```

-continued

TLVTTLTYGVQCFSRYPDHMKRHDFFKSAMPEGYVQERTISFKDDGNYKT

RAEVKFEGDTLVNRIELKGIDFKEDGNILGHKLEYNYNSHNVYITADKQK

NGIKANFKIRHNIEDGSVQLADHYQQNTPIGDGPVLLPDNHYLSTQSALS

KDPNEKRDHMVLLEFVTAAGITHGMDELYKAAA.

PSEX-TorA7II-GFP:

(SEQ ID NO: 43)

MNNNDLFQTSRQRFLAQLGGLTVAGMLGPSLLTPRRATAAQAAMAASKGE

PWELFTGVVPILVELDGDVNGHKFSVSGEGEGDATYGKLTLKFICTTGKL

PVPTLVTTLTYGVQCFSRYPDHMKRHDFFKSAMPEGYVQERTISFKDDGN

YKTRAEVKFEGDTLVNRIELKGIDPKEDGNILGHKLEYNYNSHNVYITAD

KQKNGIKANFKIRHNIEDGSVQLADHYQQNTPIGDGPVLLPDNHYLSTQS

ALSKDPNEKRDHMVLLEFVTAAGITHGMDELYKAAA.

The different GFP-phage constructs were amplified as described under "Phage amplification" using the different helper-phage systems.

Panning Rounds

Streptavidin beads (100 μl; M280; Dynal; $6.8\times10^8$ beads/ml) were re-suspended in 1 ml of PBS pH 7.4. The beads were placed in a magnetic holder, the PBS (phosphate buffered saline) was removed and the beads were re-suspended in 1 ml of 3% BSA in PBS-Tween20 (0.05% (v/v)) and incubated over night at 4° C. on a rotary wheel for blocking. The next day, the library members were prepared as follows:

For scenario I (as outlined in FIG. 25), 100 μl of $10^8$ Pfu/ml of BirA-GFP-phage (=$10^7$ phages) in 3% BSA, PBS-Tween20 (0.05% (v/v)) was added to the beads and incubated for 1 h at 19° C. on a rotary wheel for coupling. The coupled beads were placed on a magnetic holder and washed 3× with PBS pH7.4 to remove uncoupled phages. Next the pre-absorbed library mixtures (in 3% (w/v) BSA, PBS-Tween 20 (0.05%)), consisting of 100 μl of $10^8$ Pfu/ml of anti-GFP-phage (=$10^7$ phages) as well as 1 μl of $10^{13}$ Pfu/ml of anti-phOx-phages (=$10^{10}$ phages) was added to the coupled beads, resulting in a library with ratios between BirA-GFP-phage vs anti-phOx-phage: 1:1000 as well as a ratio between anti-GFP-phage vs anti-phOx-phage of 1:1000. A second tube was prepared in parallel in which similar ratios between BirA-GFP-phage vs anti-phOx-phage of 1:1000 were incubated, but no anti-GFP-phage was present. These tubes served as negative control.

All mixtures were incubated for 1 h on a rotary wheel at 19° C. on the BirA-GFP-coupled beads. Tubes were placed on a magnetic holder and washed 5× with PBS-Tween (0.05%) during all panning rounds. Alkaline TEA elution was performed for 3 min at room temperature, followed by neutralization with 1M Tris-HCl pH8.0 during all panning rounds.

In case of scenario II (as outlined in FIG. 25), all 3 library members with similar ratios as described above were first incubated in solution in 3% (w/v) BSA, PBS-Tween (0.05%) for 1 h at 19° C. on a rotary wheel. Next 100 μl of blocked beads was added to the reaction mix and incubated for 1 h at 19° C. on a rotary wheel. Tubes were placed on a magnetic holder and washed 5× with PBS-Tween (0.05%) during all panning rounds. Alkaline Tris-Ethyl-Amine (TEA; 250 μl of 100 mM TEA for 3 min) at 19° C., followed by neutralization with 1M Tris-HCl pH 8.0 during all panning rounds.

Phage Elution and Infection

Phages were eluted using alkaline Tris-Ethyl-Amine (250 μl of 100 mM TEA for 3 min), followed by neutralization upon addition of 250 μl 1M Tris-HCl pH8.0 to the reaction mix. An XL-1 culture grown to a mid $OD_{600}$~0.3 to 0.5 in LB-medium, supplemented with 30 μg/ml Tetracycline, was infected with the different eluted phage-mixtures by incubation at 60 rpm at 37° C. on a shaker for 15 min, followed by an incubation at 220 rpm at 37° C. for 45 min. The solutions were next transferred into Falcon tubes and spun down for 10 min at 4000 rpm at 19° C. The infected bacterial pellet was re-suspended in 1 ml of LB-medium and plated on to large LB-agar plates (Nunc), supplemented with 100 μg/ml of Ampicillin, 30 μg/ml Tetracycline and 0.1 M Glucose. Dilution series were plated on small LB-agar plates, supplemented with 100 μg/ml of Ampicillin, 30 μg/ml Tetracycline and 0.1 M Glucose. All plates were incubated at 37° C. over night. The next day, the infected bacteria were harvested from the plates upon addition of 10 ml LB-medium and scraping with a Drigalski spatula. The $OD_{600}$ of the harvested bacteria was measured diluted to a start $OD_{600}$ of 0.025 for phage amplification (see Phage amplification for following steps).

Phage Amplification

Phages were grown over night in LB-medium, supplemented with 100 μg/ml of Ampicillin, 100 mM Glucose and 30 μg/ml of Tetracycline at 37° C. The next morning, the cultures were re-inoculated in a 500 ml Erlenmeyer-flask to a start $OD_{600}$ of 0.025 in 40 ml of LB-medium, supplemented with 100 μg/ml of Ampicillin, 100 mM Glucose and 30 μg/ml of Tetracyclin at 37° C. The cultures were grown until an $OD_{600}$ of 0.1 was reached. For infection, an equivalent of moyen of infection (moi) of 8 of the following helper-phages was added to the cultures. Whereas during panning rounds solely M13K07 (Stratagene) helper phage was used, the GFP-phage was amplified with M13K07 (Stratagene) helper phage, with Hyper-phage (Progene) and with BirA-VCSM13 (Geir-Åge Løset) helper phage in parallel.

The cultures were left for 15 min at 37° C. at 60 rpm on the shaker, followed by incubation for 45 min at 37° C. at 220 rpm on the shaker. Cells were transferred into falcon tubes and harvested upon centrifugation for 10 min at 4000 rpm at 19° C. 50 ml of 2YT media, supplemented with 100 μg/ml of Ampicillin and 50 μg/ml of Kanamycin, was added. In case of the Hyper-Phage amplification a final concentration of 100 μM IPTG was added. The cultures were incubated over night at 30° C. at 220 rpm on the shaker. For BirA-packaging, phage-cultures were incubated at 37° C. instead of 30° C. over night.

Phages were transferred to 50 ml Falcon tubes the next day, spun down at 6000 rpm at 4° C. for 15 min The supernatant was transferred into fresh 50 ml Falcon tubes and 1/5 of volume (10 ml) of PEG 6000/NaCl was added. Phages were precipitated by incubation on ice for 2 h, followed by centrifugation at 6000 rpm at 4° C. for 15 min The pellet was re-suspended in 2 ml of PBS pH 7.4, transferred to eppendorf-tubes and centrifuged at 14000 rpm at 4° C. for 10 min to remove bacterial cell debris. The supernatant was transferred to fresh eppendorf-tubes and phages were stored at 4° C.

The concentration of the phages was determined by absorbance measurement as well as by titration experiments. Absorbance measurements were performed after the protocol of Day L A et al [JMB, 39, 265-277 (1969)] using following equation:

$$Pfu/\text{ml} = \frac{(A_{269} - A_{320})}{(\text{genome in nt})} * 6 * 10^{16} * f,$$

where the size of the phage genome is 5000 nt and f is the dilution factor.

For determining the phage-titer, an XL-1Blue over night culture was grown in LB-medium, supplemented with 30 μg/ml of Tetracycline. The culture was re-inoculated the next day to a start $OD_{600}$ of 0.05 in LB-medium, supplemented with 30 μg/ml of Tetracycline to mid-log $OD_{600}$ of 0.3-0.5. Dilutions of $10^{-7}$ and $10^{-8}$ of the phages were prepared and added to 500 μl of XL-1 culture. The samples were incubated for 30 min at 37° C. without shaking. 100 μl of each sample was plated out on LB-agar plates, supplemented with 100 μg/ml of Ampicillin, 100 mM Glucose and 30 μg/ml of Tetracycline. Plates were incubated over night at 37° C., colonies were counted and the titer was determined the next day.

Phage ELISA Experiments

For the detection of anti-GFP-phages during ELISA experiments, maxisorp ELISA-plates (Nunc) were coated with 100 μl/well of recombinant expressed GFP at a concentration of either 10 or 5 μg/ml in PBS pH 7.4 over night at 4° C. The next day, wells were washed 3× with PBS pH 7.4 and 200 μl of 4% milk solution in PBS pH 7.4 was added to block un-coated wells for 2 h at 19° C. with mild shaking on a titramax. Wells were washed 3× with 200 μl of PBS-Tween 20 (0.05%) afterwards and amplified phages were added to the wells in serial dilutions in the presence of 4% milk in PBS pH 7.4 and incubated for 1 h at 19° C. with mild shaking on a titramax. Wells were washed 5× with PBS-Tween 20 (0.05%) to remove decrease unspecific binders. Rabbit anti-Fd-antibody (Sigma, dilution of 1:1000 in PBS-Tween 20 (0.05%)) was added and incubated for 1 h with mild shaking at 19° C. on a titramax. The wells were washed 3× with 200 μl of PBS-Tween 20 (0.05%). Goat anti-rabbit-HRP-coupled antibody (1:5000 dilutions in PBS-Tween 20 (0.05%)) was added and incubated for 1 h with mild shaking at 19° C. on a titramax. Wells were washed 3× with 200 μl of PBS-Tween 20 (0.05%) and 1× with 200 μl of PBS. 100 μl of ABTS substrate was added to the wells and the plate was incubated for 30 min at 37° C. Absorbance measurement was performed at 405 nm using a Tecan plate reader.

For the detection of GFP-phages during ELISA experiments, phages from panning rounds were coated with 100 μl/well over night at 4° C. in serial dilutions. The next day, wells were washed 3× with PBS pH 7.4 and 200 μl of 4% milk solution in PBS pH 7.4 was added to block un-coated wells for 2 h at 19° C. with mild shaking on a titramax. 100 μl of anti-GFP antibody (polyclonal; rabbit; Santa-Cruz) was added to the wells at a dilution of 1:1000 in PBS-Tween 20 (0.05%). After one hour of incubation at 19° C., ELISA-wells were washed three times with PBS-Tween 20 (0.05%). Anti-rabbit-HRP-coupled antibody was added at a dilution of 1:1000 in PBS-Tween 20 (0.05%) and incubated on the wells for 1 h at 19° C. The ELISA plate was washed three times with PBS-Tween 20 (0.05%) afterwards and 100 μl of ABTS substrate was added to the wells. The plate was incubated for 30 min at 37° C. Absorbance measurement was performed at 405 nm using a Tecan plate reader.

Beads ELISA

Streptavidin beads (100 μl; M280; Dynal; $6.8\times10^{8}$ beads/ml) were re-suspended in 1 ml of PBS pH 7.4. The beads were placed in a magnetic holder, the PBS was removed and the beads were re-suspended in 1 ml of 3% BSA in PBS-Tween 20 (0.05%) and incubated over night at 4° C. on a rotary wheel for blocking. The next day, the beads were placed on a magnetic holder and washed 3× with 1 ml of PBS pH 7.4. A final volume of 1 ml of PBS was added in the last step and 50 μl of beads were transferred into wells of a 96-V-shaped microtiter plate (Greiner). 20 μl of phages ($10^{13}$ Pfu/ml) were diluted with 80 μl (1:5 dilution) of 4% milk in PBS pH7.4 and pipetted to the beads-containing wells. 20 μl from well A were transferred to well B, containing already 80 μl of milk and so on, leading to a dilution series. Phages were incubated for 1 h with mild shaking at 19° C. on a titramax. The plate was placed on a magnetic plate holder and phages were washed 3× with 150 μl of PBS-Tween 20 (0.05%). Rabbit anti-Fd-antibody (Sigma, dilution of 1:1000 in PBS-Tween 20 (0.05%)) was added and incubated for 1 h with mild shaking at 19° C. on a titramax. The plate was placed on a magnetic plate holder and the wells were washed 3× with 150 μl of PBS-Tween 20 (0.05%). Goat anti-rabbit-HRP-coupled antibody (1:5000 dilutions in PBS-Tween 20 (0.05%)) was added next and incubated for 1 h with mild shaking at 19° C. on a titramax. The plate was placed on a magnetic plate holder and the wells were washed 3× with 150 μl of PBS-Tween 20 (0.05%). 100 μl of ABTS substrate was added to the wells and the plate was incubated for 30 min at 37° C. The plate was again placed on to a magnetic plate holder and the reaction mix of each well was transferred into a fresh microtiter plate to remove unspecific signals from the beads. Absorbance measurement was performed at 405 nm using a Tecan plate reader.

Western Blot Analysis

Amplified phages were diluted into 1× sample buffer and boiled for 5 min at 95° C. Two gels were run in parallel. Therefore, 10 μl of sample was next loaded on to a 10%-Bis-Tris gel (NuPage, Invitrogen), 5 μl of Dual Color Precision Plus marker was loaded as marker. The gel was run for 10 min at 90 V, followed by 90 min at 150 V. The two gels were transferred to a nitrocellulose membrane by blotting for 7 min (iBlot Gel Transfer Stacks Nitrocellulose, Mini, Invitrogen). Membranes were washed one time with PBS pH7.4 and blocked over night at 4° C. in 5% milk. Next morning, membranes were washed three times with PBS-Tween 20 (0.05%) (0.05%) and an anti-GFP antibody (polyclonal; rabbit; Santa-Cruz) was added to the first membrane at a dilution of 1:1000 in PBS-Tween 20 (0.05%) in 5% milk whereas to the second membrane and an anti-geneIII antibody (monoclonal; mouse; NordicBioSite) was added at a dilution of 1:1000 in PBS-Tween 20 (0.05%) in 5% milk. After one hour of incubation at 19° C., membranes were washed three times with PBS-Tween 20 (0.05%). For detection of the GFP, an anti-rabbit-HRP-coupled antibody was added at a dilution of 1:5000 in PBS-Tween 20 (0.05%) in 5% milk, the pIII was detected by addition of an anti-mouse-HRP antibody (dilution of 1:5000 in PBS-Tween 20 (0.05%) in 5% milk). Both antibodies were incubated on the membranes for 1 h at 19° C. and membranes were washed three times with PBS-Tween 20 (0.05%) pH7.4 and 1× with PBS pH7.4. For detection, a 1:1 mixture of ECL-detection solution was prepared, incubated for 1 min on the membranes and developed.

REFERENCES

1. Endemann, H. & Model, P. Loccoation of Filamentous Phage Minor Coat Proteins in Phage and in Infected Cells. Journal of Molecular Biology 250, 496-506 (1995).
2. Gao, C. et al. Making artificial antibodies: A format for phage display of combinatorial heterodimeric arrays. PNAS 96, 6025-6030 (1999).
3. Kwaśnikowski P, Kristensen P, Markiewicz W T. Multivalent display system on filamentous bacteriophage pVII minor coat protein. J Immunol Methods. 2005 Dec. 20; 307(1-2):135-43. Epub 2005 Oct. 28.
4. Khalil A S, Ferrer J M, Brau R R, Kottmann S T, Noren C J, Lang M J, Belcher A M. Single M13 bacteriophage tethering and stretching. Proc Natl Acad Sci USA. 2007 Mar. 20; 104(12):4892-7. Epub 2007 Mar. 13.

5. Baneyx F, Mujacic M. Recombinant protein folding and misfolding in *Escherichia coli*. Nat. Biotechnol. 2004 November; 22(11):1399-408.

6. Simons G F, Konings R N, Schoenmakers J G. Genes VI, VII, and IX of phage M13 code for minor capsid proteins of the virion. Proc Natl Acad Sci USA. 1981 July; 78(7): 4194-8.

7. Scott J K, Smith G P. Searching for peptide ligands with an epitope library. Science. 1990 Jul. 27; 249(4967):386-90.

8. Koch J, Breitling F, Dubel S. Rapid titration of multiple samples of filamentous bacteriophage (M13) on nitrocellulose filters. Biotechniques. 2000 December; 29(6):1196-8, 2002.

9. Kipriyanov S M, Moldenhauer G, Little M. High level production of soluble single chain antibodies in small-scale *Escherichia coli* cultures J Immunol Methods. 1997 Jan. 15; 200(1-2):69-77.

10. Welschof M, Terness P, Kipriyanov S M, Stanescu D, Breitling F, Dorsam H, Dubel S, Little M, Opelz G. The antigen-binding domain of a human IgGanti-F(ab')2 autoantibody. Proc Natl Acad Sci USA. 1997 Mar. 4; 94(5): 1902-7.

11. Michaelsen T E, Aase A, Westby C, Sandlie I. Enhancement of complement activation and cytolysis of human IgG3 by deletion of hinge exons. Scand J. Immunol. 1990 November; 32(5):517-28.

12. Nakela O, Kaartinen M, Pelkonen J L, Karjalainen K. Inheritance of antibody specificity V. Anti-2-phenyloxazolone in the mouse. J Exp Med. 1978 Dec. 1; 148(6): 1644-60.

13. Loset G A, Lunde E, Bogen B, Brekke O H, Sandlie I. Functional phage display of two murine alpha/beta T-cell receptors is strongly dependent on fusion format, mode and periplasmic folding assistance. Protein Eng Des Sel. 2007 September; 20(9):461-72. Epub 2007 Oct. 9.

14. Norderhaug L, Olafsen T, Michaelsen T E, Sandlie I. Versatile vectors for transient and stable expression of recombinant antibody molecules in mammalian cells. J Immunol Methods. 1997 May 12; 204(1):77-87.

15. Bradbury A R, Marks J D. Antibodies from phage antibody libraries J Immunol Methods. 2004 July; 290(1-2): 29-49.

16. de Haard H J, van Neer N, Reurs A, Hufton S E, Roovers R C, Henderikx P, de Bruine A P, Arends J W, Hoogenboom H R. A large non-immunized human Fab fragment phage library that permits rapid isolation and kinetic analysis of high affinity antibodies. A large non-immunized human Fab fragment phage library that permits rapid isolation and kinetic analysis of high affinity antibodies.

17. Hoogenboom H R. Selecting and screening recombinant antibody libraries. Nat Biotechnol. 2005 September; 23(9):1105-16.

18. Marks J D, Hoogenboom H R, Bonnert T P, McCafferty J, Griffiths A D, Winter G. By-passing immunization. Human antibodies from V-gene libraries displayed on phage. J Mol Biol. 1991 Dec. 5; 222(3):581-97.

19. Altschul S F, Gish W, Miller W, Myers E W, Lipman D J. Basic local alignment search tool. J Mol Biol. 1990 Oct. 5; 215(3):403-10.

The invention claimed is:

1. A method for screening at least two phage display libraries against each other to identify and/or select one or more interacting binding partners comprising:

(a) providing a first phage display library, wherein phages of said first phage display library are bispecific and comprise a member of a first library displayed at a first position and a first tag displayed at a second position;

(b) contacting said first bispecific phage display library with a second bispecific phage display library under conditions permitting binding between members of the first bispecific phage display library and the second bispecific phage display library to form library 1-library 2 complexes, wherein phages of said second phage display library comprise a member of a second library displayed at a first position and a second tag displayed at a second position, wherein (i) said first library and second library displayed at the pIII position on the phage particles and the first and second tag molecules are displayed at the pVII position on the phage particles; or (ii) said first library is displayed at the pIII position and the first tag is displayed at the pVII position on the phage particles and wherein said second library is displayed at the pVII position and the second tag is displayed at the pIII position on the phage particles; or (iii) said first library is displayed at the pVII position and the first tag is displayed at the pIII position on the phage particles and wherein said second library is displayed at the pIII position and the second tag is displayed at the pVII position on the phage particles; or (iv) said first library and second library are displayed at the pVII position on the phage particles and the tag molecules are displayed at the pIII position on the phage particles;

and wherein the first and second s are different; and (c) separating library 1-library 2 complexes from unbound first bispecific phage display library members or unbound second bispecific phage display library members wherein the separation step (c) is carried out by one or more steps which comprise immobilizing either the first phage display library or the second phage display library onto a solid phase by way of said tags displayed on the phage display libraries, and wherein the one or more steps which comprise immobilizing are carried out before or after step (b).

2. The method of claim 1, wherein the separation step comprises the steps of:

(i) eluting both the non-complexed members of the first library or second library and the library 1-library 2 complexes from the solid phase;

(ii) immobilizing library 1-library 2 complexes onto a second solid phase by way of a tag which is present in the library 1-library 2 complexes but is not present on the non-complexed library members; and (iii) separating said solid phase from the other components of the reaction mixture.

3. The method of claim 2, comprising an additional step wherein the library 1-library 2 complexes are eluted from the second solid phase.

4. The method of claim 1, further comprising a step wherein the library 1-library 2 complexes are detached from each other.

5. The method of claim 1, wherein a sequence encoding an N-terminal signal peptide is present in the nucleic acid molecules encoding the pIII fusion proteins and a sequence encoding an N-terminal signal peptide is not present in the nucleic acid molecules encoding the pVII fusion proteins.

6. The method of claim 5, wherein said signal peptide is selected from the group consisting of: pelB, OmpA, TorA, malE, phoA, lamB, Bla, DspA, mglB, sfmC, tolB, TorT and pIII.

7. The method of claim 6, wherein said signal peptide is TorA7I, TorA7II or pelB.

8. The method of claim 5, wherein said signal peptide targets the pIII fusion protein to the SRP-, SEC-, TatABC- or YidC-secretory pathways.

9. The method of claim 1, wherein one of said first library or said second library is an antibody library and the other of said first library or said second library is an antigen library or a second antibody library.

10. The method of claim 9, wherein said first and second libraries are antibody libraries and wherein said method is used to select anti-idiotypic antibodies.

11. The method of claim 1, wherein said tags are selected from the group consisting of His tags, biotin tags and antigen peptide tags.

12. The method of claim 11, wherein said biotin tag is MSGLNDIFEAQKIEWHE (SEQ IN NO:4) or said antigen peptide tag is c-myc, FLAG, HA, HAT or V5.

13. The method of claim 1, wherein said solid phase is particulate.

14. The method of claim 1, wherein the steps of the method are repeated one or more times.

15. The method of claim 1, wherein the interacting binding partners (library 1-library 2 complexes) or the individual members thereof are subjected to further manipulation or analysis.

16. The method of claim 15, further comprising a step wherein said interacting binding partners or the individual members thereof are detached, removed, eluted, isolated from each other, or are expressed or produced in isolation from each other.

17. The method of claim 1, further comprising a step of manufacturing said identified or selected interacting binding partner or the individual members thereof, or a component, fragment, variant, or derivative thereof, and optionally formulating said manufactured binding partner or the individual members thereof with at least one pharmaceutically acceptable carrier or excipient.

18. The method of claim 13, wherein said particulate is magnetic or magnetizable.

* * * * *

SEQUENCE LISTING

```
<160> NUMBER OF SEQ ID NOS: 51

<210> SEQ ID NO 1
<211> LENGTH: 33
<212> TYPE: PRT
<213> ORGANISM: Bacteriophage M13

<400> SEQUENCE: 1

Met Glu Gln Val Ala Asp Phe Asp Thr Ile Tyr Gln Ala Met Ile Gln
1               5                   10                  15

Ile Ser Val Val Leu Cys Phe Ala Leu Gly Ile Ile Ala Gly Gly Gln
            20                  25                  30

Arg


<210> SEQ ID NO 2
<211> LENGTH: 424
<212> TYPE: PRT
<213> ORGANISM: Bacteriophage fd

<400> SEQUENCE: 2

Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
        35                  40                  45

Ala Asn Tyr Glu Gly Cys Leu Trp Asn Ala Thr Gly Val Val Val Cys
    50                  55                  60

Thr Gly Asp Glu Thr Gln Cys Tyr Gly Thr Trp Val Pro Ile Gly Leu
65                  70                  75                  80
```

-continued

```
Ala Ile Pro Glu Asn Glu Gly Gly Gly Ser Glu Gly Gly Gly Ser Glu
                85                  90                  95

Gly Gly Gly Ser Glu Gly Gly Gly Thr Lys Pro Pro Glu Tyr Gly Asp
            100                 105                 110

Thr Pro Ile Pro Gly Tyr Thr Tyr Ile Asn Pro Leu Asp Gly Thr Tyr
        115                 120                 125

Pro Pro Gly Thr Glu Gln Asn Pro Ala Asn Pro Asn Pro Ser Leu Glu
    130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Pro Val Asn Ala Gly Gly Gly Ser Gly
225                 230                 235                 240

Gly Gly Ser Gly Gly Gly Ser Glu Gly Gly Gly Ser Glu Gly Gly Gly
                245                 250                 255

Ser Glu Gly Gly Gly Ser Glu Gly Gly Gly Ser Gly Gly Gly Ser Gly
            260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
        355                 360                 365

Ser Val Glu Cys Arg Pro Tyr Val Phe Gly Ala Gly Lys Pro Tyr Glu
    370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420


<210> SEQ ID NO 3
<211> LENGTH: 73
<212> TYPE: PRT
<213> ORGANISM: Bacteriophage M13

<400> SEQUENCE: 3

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30
```

```
Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70


<210> SEQ ID NO 4
<211> LENGTH: 17
<212> TYPE: PRT
<213> ORGANISM: Artificial
<220> FEATURE:
<223> OTHER INFORMATION: synthetic peptide

<400> SEQUENCE: 4

Met Ser Gly Leu Asn Asp Ile Phe Glu Ala Gln Lys Ile Glu Trp His
1               5                   10                  15

Glu


<210> SEQ ID NO 5
<211> LENGTH: 76
<212> TYPE: DNA
<213> ORGANISM: Artificial
<220> FEATURE:
<223> OTHER INFORMATION: oligonucleotide

<400> SEQUENCE: 5

ccggctaagt aacatgtccg gcctgaacga tatctttgaa gcgcagaaaa ttgaatggca     60

tgaaatggag caggtc                                                     76


<210> SEQ ID NO 6
<211> LENGTH: 76
<212> TYPE: DNA
<213> ORGANISM: Artificial
<220> FEATURE:
<223> OTHER INFORMATION: oligonucleotide

<400> SEQUENCE: 6

gacctgctcc atttcatgcc attcaatttt ctgcgcttca aagatatcgt tcaggccgga     60

catgttactt agccgg                                                     76


<210> SEQ ID NO 7
<211> LENGTH: 53
<212> TYPE: DNA
<213> ORGANISM: Artificial
<220> FEATURE:
<223> OTHER INFORMATION: oligonucleotide

<400> SEQUENCE: 7

ccggctaagt aacatggact acaaagatga cgatgacaaa atggagcagg tcg            53


<210> SEQ ID NO 8
<211> LENGTH: 53
<212> TYPE: DNA
<213> ORGANISM: Artificial
<220> FEATURE:
<223> OTHER INFORMATION: oligonucleotide

<400> SEQUENCE: 8

cgacctgctc cattttgtca tcgtcatctt tgtagtccat gttacttagc cgg            53


<210> SEQ ID NO 9
```

<211> LENGTH: 9
<212> TYPE: PRT
<213> ORGANISM: Artificial
<220> FEATURE:
<223> OTHER INFORMATION: synthetic peptide

<400> SEQUENCE: 9

Met Asp Tyr Lys Asp Asp Asp Asp Lys
1               5

<210> SEQ ID NO 10
<211> LENGTH: 47
<212> TYPE: DNA
<213> ORGANISM: Artificial
<220> FEATURE:
<223> OTHER INFORMATION: oligonucleotide

<400> SEQUENCE: 10
ccggctaagt aacatgcatc accatcacca tcacatggag caggtcg 47

<210> SEQ ID NO 11
<211> LENGTH: 47
<212> TYPE: DNA
<213> ORGANISM: Artificial
<220> FEATURE:
<223> OTHER INFORMATION: oligonucleotide

<400> SEQUENCE: 11
cgacctgctc catgtgatgg tgatggtgat gcatgttact tagccgg 47

<210> SEQ ID NO 12
<211> LENGTH: 7
<212> TYPE: PRT
<213> ORGANISM: Artificial
<220> FEATURE:
<223> OTHER INFORMATION: synthetic peptide

<400> SEQUENCE: 12

Met His His His His His His
1               5

<210> SEQ ID NO 13
<211> LENGTH: 39
<212> TYPE: DNA
<213> ORGANISM: Artificial
<220> FEATURE:
<223> OTHER INFORMATION: oligonucleotide

<400> SEQUENCE: 13
agaggagaaa ttaaccatgg aatacctatt gcctacggc 39

<210> SEQ ID NO 14
<211> LENGTH: 39
<212> TYPE: DNA
<213> ORGANISM: Artificial
<220> FEATURE:
<223> OTHER INFORMATION: oligonucleotide

<400> SEQUENCE: 14
gccgtaggca ataggtattc catggttaat ttctcctct 39

<210> SEQ ID NO 15
<211> LENGTH: 21
<212> TYPE: DNA
<213> ORGANISM: Artificial
<220> FEATURE:
<223> OTHER INFORMATION: oligonucleotide

<400> SEQUENCE: 15
tagctcactc attaggcacc c 21

<210> SEQ ID NO 16
<211> LENGTH: 18
<212> TYPE: DNA
<213> ORGANISM: Artificial
<220> FEATURE:
<223> OTHER INFORMATION: oligonucleotide

<400> SEQUENCE: 16
tttggatcca gcggccgc 18

<210> SEQ ID NO 17
<211> LENGTH: 35
<212> TYPE: DNA
<213> ORGANISM: Artificial
<220> FEATURE:
<223> OTHER INFORMATION: oligonucleotide

<400> SEQUENCE: 17
atatgatatc agaatggagc aggtcgcgga tttcg 35

<210> SEQ ID NO 18
<211> LENGTH: 40
<212> TYPE: DNA
<213> ORGANISM: Artificial
<220> FEATURE:
<223> OTHER INFORMATION: oligonucleotide

<400> SEQUENCE: 18
atatgctagc ttatcatctt tgacccccag cgattatacc 40

<210> SEQ ID NO 19
<211> LENGTH: 46
<212> TYPE: DNA
<213> ORGANISM: Artificial
<220> FEATURE:
<223> OTHER INFORMATION: oliognucleotide

<400> SEQUENCE: 19
atctcttcca tggagcaggt cgcggatttc gacacaattt atcagg 46

<210> SEQ ID NO 20
<211> LENGTH: 38
<212> TYPE: DNA
<213> ORGANISM: Artificial
<220> FEATURE:
<223> OTHER INFORMATION: oligonucleotide

<400> SEQUENCE: 20
atctcttcca tgttacttag ccggaacgag gcgcagac 38

<210> SEQ ID NO 21
<211> LENGTH: 43
<212> TYPE: DNA
<213> ORGANISM: Artificial
<220> FEATURE:
<223> OTHER INFORMATION: oligonucleotide

<400> SEQUENCE: 21
atctcttcac atgaaatacc tattgcctac ggcagccgct ggc 43

<210> SEQ ID NO 22

<211> LENGTH: 33
<212> TYPE: DNA
<213> ORGANISM: Artificial
<220> FEATURE:
<223> OTHER INFORMATION: oligonucleotide

<400> SEQUENCE: 22
tctcttcaca tggcccaggt gcagctggtg cag 33

<210> SEQ ID NO 23
<211> LENGTH: 41
<212> TYPE: DNA
<213> ORGANISM: Artificial
<220> FEATURE:
<223> OTHER INFORMATION: oligonucleotide

<400> SEQUENCE: 23
atctcttccc attctgatat ctttggatcc agcggccgca c 41

<210> SEQ ID NO 24
<211> LENGTH: 24
<212> TYPE: DNA
<213> ORGANISM: Artificial
<220> FEATURE:
<223> OTHER INFORMATION: oligonucleotide

<400> SEQUENCE: 24
agcagctttg ttacgttgat ttgg 24

<210> SEQ ID NO 25
<211> LENGTH: 19
<212> TYPE: DNA
<213> ORGANISM: Artificial
<220> FEATURE:
<223> OTHER INFORMATION: oligonucleotide

<400> SEQUENCE: 25
gcagcgaaag acagcatcg 19

<210> SEQ ID NO 26
<211> LENGTH: 253
<212> TYPE: PRT
<213> ORGANISM: Artificial
<220> FEATURE:
<223> OTHER INFORMATION: scFv antibody

<400> SEQUENCE: 26

```
Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Ala Tyr Asn Gly Tyr Lys Ser Tyr Ala Gln Asn Phe
    50                  55                  60

Gln Gly Arg Val Thr Met Thr Thr Asp Thr Phe Thr Ser Thr Ala Tyr
65                  70                  75                  80

Met Glu Leu Arg Thr Leu Arg Ser Asp Asp Thr Ala Val Tyr Tyr Cys
                85                  90                  95

Val Arg Leu Val Pro Lys Arg Thr Ala Thr Leu His Tyr Tyr Ile Asp
            100                 105                 110

Val Trp Gly Lys Gly Thr Thr Val Thr Val Ser Ser Gly Ser Ala Ser
        115                 120                 125
```

```
Ala Pro Lys Leu Glu Glu Gly Glu Phe Ser Glu Ala Arg Val Gln Ser
    130                 135                 140

Val Leu Thr Gln Pro Pro Ser Val Ser Ala Ala Pro Gly Gln Lys Val
145                 150                 155                 160

Thr Ile Ser Cys Ser Gly Ser Ser Ser Asn Ile Gly Asn Asn Tyr Val
                165                 170                 175

Ser Trp Tyr Val Gln Leu Pro Gly Thr Ala Pro Lys Leu Leu Ile Tyr
            180                 185                 190

Asp Asn Asn Lys Arg Phe Ser Gly Val Pro Asp Arg Phe Ser Gly Ser
        195                 200                 205

Lys Ser Gly Thr Ser Ala Thr Leu Gly Ile Thr Gly Leu Gln Thr Gly
    210                 215                 220

Asp Glu Ala Asp Tyr Tyr Cys Gly Ala Trp Asp Gly Ser Leu Arg Glu
225                 230                 235                 240

Ala Val Phe Gly Gly Gly Thr Lys Val Thr Val Leu Gly
                245                 250


<210> SEQ ID NO 27
<211> LENGTH: 249
<212> TYPE: PRT
<213> ORGANISM: Artificial
<220> FEATURE:
<223> OTHER INFORMATION: scFv antibody

<400> SEQUENCE: 27

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Tyr Gly Ser Ser Tyr Phe Asp Tyr Trp Gly Gln
            100                 105                 110

Gly Thr Thr Leu Thr Val Ser Ser Leu Glu Gly Gly Gly Gly Ser Gly
        115                 120                 125

Gly Gly Gly Ser Gly Gly Gly Gly Ser Glu Leu Gln Ala Val Val Thr
    130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Asn Arg Ala Pro Gly Val Pro Ala Arg Phe Ser Gly Ser Leu Ile
        195                 200                 205

Gly Asp Lys Ala Ala Leu Thr Ile Thr Gly Thr Gln Thr Glu Asp Glu
    210                 215                 220

Ala Met Tyr Phe Cys Ala Leu Trp Tyr Ser Asn His Trp Val Phe Gly
225                 230                 235                 240
```

```
Gly Gly Thr Lys Leu Thr Val Leu Gly
                245


<210> SEQ ID NO 28
<211> LENGTH: 248
<212> TYPE: PRT
<213> ORGANISM: Artificial
<220> FEATURE:
<223> OTHER INFORMATION: scTCR antibody

<400> SEQUENCE: 28

Gln Gln Lys Val Gln Gln Ser Pro Glu Ser Leu Ile Val Pro Glu Gly
1               5                   10                  15

Ala Met Thr Ser Leu Asn Cys Thr Phe Ser Asp Ser Ala Ser Gln Tyr
            20                  25                  30

Phe Ala Trp Tyr Arg Gln Gln Ser Gly Lys Ala Pro Lys Ala Leu Met
        35                  40                  45

Ser Ile Phe Ser Asn Gly Glu Lys Glu Glu Gly Arg Phe Thr Ile His
    50                  55                  60

Leu Asn Lys Ala Ser Leu His Phe Ser Leu His Ile Arg Asp Ser Gln
65                  70                  75                  80

Pro Ser Asp Ser Ala Leu Tyr Leu Cys Ala Val Arg Gly Pro Asn Thr
                85                  90                  95

Gly Asn Tyr Lys Tyr Val Phe Gly Ala Gly Thr Arg Leu Lys Val Ile
            100                 105                 110

Ala Lys Leu Ser Gly Ser Ala Ser Ala Pro Lys Leu Glu Glu Gly Glu
        115                 120                 125

Phe Ser Glu Ala Arg Val Glu Ala Ala Val Thr Gln Ser Pro Arg Asn
    130                 135                 140

Lys Val Ala Val Thr Gly Gly Lys Val Thr Leu Ser Cys Asn Gln Thr
145                 150                 155                 160

Asn Asn His Asn Asn Met Tyr Trp Tyr Arg Gln Asp Thr Gly His Gly
                165                 170                 175

Leu Arg Leu Ile His Tyr Ser Tyr Gly Ala Gly Ser Thr Glu Lys Gly
            180                 185                 190

Asp Ile Pro Asp Gly Tyr Lys Ala Ser Arg Pro Ser Gln Glu Asn Phe
        195                 200                 205

Ser Leu Ile Leu Glu Leu Ala Thr Pro Ser Gln Thr Ser Val Tyr Phe
    210                 215                 220

Cys Ala Ser Gly Asp Ala Gly Gln Gly His Ser Asp Tyr Thr Phe Gly
225                 230                 235                 240

Ser Gly Thr Arg Leu Leu Val Ile
                245


<210> SEQ ID NO 29
<211> LENGTH: 4864
<212> TYPE: DNA
<213> ORGANISM: Artificial
<220> FEATURE:
<223> OTHER INFORMATION: vector pSEX81-215

<400> SEQUENCE: 29

tggcgtaata gcgaagaggc ccgcaccgat cgcccttccc aacagttgcg cagcctgaat      60

ggcgaatggg acgcgccctg tagcggcgca ttaagcgcgg cgggtgtggt ggttacgcgc     120

agcgtgaccg ctacacttgc cagcgcccta gcgcccgctc ctttcgcttt cttcccttcc     180

tttctcgcca cgttcgccgg ctttccccgt caagctctaa atcgggggct ccctttaggg     240
```

```
ttccgattta gtgctttacg gcacctcgac cccaaaaaac ttgattaggg tgatggttca    300
cgtagtgggc catcgccctg atagacggtt tttcgccctt tgacgttgga gtccacgttc    360
tttaatagtg gactcttgtt ccaaactgga acaacactca accctatctc ggtctattct    420
tttgatttat aagggatttt gccgatttcg gcctattggt taaaaaatga gctgatttaa    480
caaaaattta acgcgaattt taacaaaata ttaacgctta caatttaggt ggcacttttc    540
ggggaaatgt gcgcggaacc cctatttgtt tatttttcta aatacattca aatatgtatc    600
cgctcatgag acaataaccc tgataaatgc ttcaataata ttgaaaaagg aagagtatga    660
gtattcaaca tttccgtgtc gcccttattc cctttttttgc ggcattttgc cttcctgttt    720
ttgctcaccc agaaacgctg gtgaaagtaa aagatgctga agatcagttg ggtgcacgag    780
tgggttacat cgaactggat ctcaacagcg gtaagatcct tgagagtttt cgccccgaag    840
aacgttttcc aatgatgagc acttttaaag ttctgctatg tggcgcggta ttatcccgta    900
ttgacgccgg gcaagagcaa ctcggtcgcc gcatacacta ttctcagaat gacttggttg    960
agtactcacc agtcacagaa aagcatctta cggatggcat gacagtaaga gaattatgca   1020
gtgctgccat aaccatgagt gataacactg cggccaactt acttctgaca acgatcggag   1080
gaccgaagga gctaaccgct tttttgcaca acatggggga tcatgtaact cgccttgatc   1140
gttgggaacc ggagctgaat gaagccatac caaacgacga gcgtgacacc acgatgcctg   1200
tagcaatggc aacaacgttg cgcaaactat taactggcga actacttact ctagcttccc   1260
ggcaacaatt aatagactgg atggaggcgg ataaagttgc aggaccactt ctgcgctcgg   1320
cccttccggc tggctggttt attgctgata aatctggagc cggtgagcgt gggtctcgcg   1380
gtatcattgc agcactgggg ccagatggta agccctcccg tatcgtagtt atctacacga   1440
cggggagtca ggcaactatg gatgaacgaa atagacagat cgctgagata ggtgcctcac   1500
tgattaagca ttggtaactg tcagaccaag tttactcata tatactttag attgatttaa   1560
aacttcattt ttaatttaaa aggatctagg tgaagatcct ttttgataat ctcatgacca   1620
aaatccctta acgtgagttt tcgttccact gagcgtcaga ccccgtagaa aagatcaaag   1680
gatcttcttg agatcctttt tttctgcgcg taatctgctg cttgcaaaca aaaaaaccac   1740
cgctaccagc ggtggtttgt ttgccggatc aagagctacc aactcttttt ccgaaggtaa   1800
ctggcttcag cagagcgcag ataccaaata ctgtccttct agtgtagccg tagttaggcc   1860
accacttcaa gaactctgta gcaccgccta catacctcgc tctgctaatc ctgttaccag   1920
tggctgctgc cagtggcgat aagtcgtgtc ttaccgggtt ggactcaaga cgatagttac   1980
cggataaggc gcagcggtcg ggctgaacgg ggggttcgtg cacacagccc agcttggagc   2040
gaacgaccta caccgaactg agatacctac agcgtgagct atgagaaagc gccacgcttc   2100
ccgaagggag aaaggcggac aggtatccgg taagcggcag ggtcggaaca ggagagcgca   2160
cgagggagct tccaggggga aacgcctggt atctttatag tcctgtcggg tttcgccacc   2220
tctgacttga gcgtcgattt ttgtgatgct cgtcaggggg gcggagccta tggaaaaacg   2280
ccagcaacgc ggccttttta cggttcctgg ccttttgctg gccttttgct cacatgttct   2340
ttcctgcgtt atcccctgat tctgtggata accgtattac cgcctttgag tgagctgata   2400
ccgctcgccg cagccgaacg accgagcgca gcgagtcagt gagcgaggaa gcggaagagc   2460
gcccaatacg caaaccgcct ctccccgcgc gttggccgat tcattaatgc aggtatcacg   2520
aggccctttc gtcttcacct cgagagcggg cagtgagcgc aacgcaatta atgtgagtta   2580
```

```
gctcactcat taggcacccc aggctttaca ctttatgctt ccggctcgta tgttgtgtgg   2640

aattgtgagc ggataacaat ttcacacaga attcattaaa gaggagaaat taaccatgaa   2700

atacctattg cctacggcag ccgctggctt gctgctgctg gcagctcagc cggccatggc   2760

gcaagttcag ctgcagcagt ctggggctga actggtgagg cctggggtct cagtgaagat   2820

ttcctgcaag ggttctggct acaaattcac tgattatgct acgcactggg tgaaacagag   2880

tcatgcaaag agtctagagt ggattggagt tattagtact tactatggtg atactactta   2940

taaccagaag ttcaagggca aggccacaat gactgtcgac aaatcctcca gcacagccta   3000

tatggaactt cccagactga catctgatga ttctgccatc tattattgtg ccctgttacg   3060

ccccttgct tactggggcc aagggaccac ggtcaccgta tcctcaggga gtgcatccgc   3120

cccaaagctt gaagaaggtg aattttcaga agcacgcgta gatatcgtgc tgacccaatc   3180

tccactctcc ctgagtgtgt cagcaggaga gaaggtcact atgagctgca agtccagtca   3240

gagtctgtta aacagtggaa atcaaaataa cgacttggcc tggtaccagc agaaaccagg   3300

gcaacgtcct aaactgttga tctacggggc atccactagg gaatctgggg tccctgatcg   3360

cttcacaggc agtggatctg gaaccgattt cactcttacc atcagcagtg tgcaggctga   3420

agacctggca gtttattact gtcagaatga tcatagttat ccgttaacgt tcggtgctgg   3480

caccaagctg gaaatcaaac gggcggccgc tggatccaaa gatatcagag ctgaaactgt   3540

tgaaagttgt ttagcaaaat cccatacaga aaattcattt actaacgtct ggaaagacga   3600

caaaacttta gatcgttacg ctaactatga gggctgtctg tggaatgcta caggcgttgt   3660

agtttgtact ggtgacgaaa ctcagtgtta cggtacatgg gttcctattg ggcttgctat   3720

ccctgaaaat gagggtggtg gctctgaggg tggcggttct gagggtggcg gttctgaggg   3780

tggcggtact aaacctcctg agtacggtga tacacctatt ccgggctata cttatatcaa   3840

ccctctcgac ggcacttatc cgcctggtac tgagcaaaac cccgctaatc ctaatccttc   3900

tcttgaggag tctcagcctc ttaatacttt catgtttcag aataataggt tccgaaatag   3960

gcagggggca ttaactgttt atacgggcac tgttactcaa ggcactgacc ccgttaaaac   4020

ttattaccag tacactcctg tatcatcaaa agccatgtat gacgcttact ggaacggtaa   4080

attcagagac tgcgctttcc attctggctt taatgaggat ttatttgttt gtgaatatca   4140

aggccaatcg tctgacctgc ctcaacctcc tgtcaatgct ggcggcggct ctggtggtgg   4200

ttctggtggc ggctctgagg gtggtggctc tgagggtggc ggttctgagg gtggcggctc   4260

tgagggaggc ggttccggtg gtggctctgg ttccggtgat tttgattatg aaaagatggc   4320

aaacgctaat aagggggcta tgaccgaaaa tgccgatgaa aacgcgctac agtctgacgc   4380

taaaggcaaa cttgattctg tcgctactga ttacggtgct gctatcgatg gtttcattgg   4440

tgacgtttcc ggccttgcta atggtaatgg tgctactggt gattttgctg gctctaattc   4500

ccaaatggct caagtcggtg acggtgataa ttcaccttta atgaataatt tccgtcaata   4560

tttaccttcc ctccctcaat cggttgaatg tcgccctttt gtctttggcg ctggtaaacc   4620

atatgaattt tctattgatt gtgacaaaat aaacttattc cgtggtgtct ttgcgtttct   4680

tttatatgtt gccaccttta tgtatgtatt ttctacgttt gctaacatac tgcgtaataa   4740

ggagtcttaa tgatctagag gcctgtgcta atgatcagct agcttgaggc atcaataaaa   4800

cgaaaggctc agtcgaaaga ctgggccttt cgttttatct gttgtttgtc ggttaacgtc   4860

gacc                                                                4864
```

```
<210> SEQ ID NO 30
<211> LENGTH: 9206
<212> TYPE: DNA
<213> ORGANISM: Artificial
<220> FEATURE:
<223> OTHER INFORMATION: Filamentous phage display vector fUSE5,
      complete sequence

<400> SEQUENCE: 30

aacgctacta ccattagtag aattgatgcc accttttcag ctcgcgcccc aaatgaaaat     60

atagctaaac aggttattga ccatttgcga aatgtatcta atggtcaaac taaatctact    120

cgttcgcaga attgggaatc aactgttaca tggaatgaaa cttccagaca ccgtacttta    180

gttgcatatt taaaacatgt tgaactacag caccagattc agcaattaag ctctaagcca    240

tccgcaaaaa tgacctctta tcaaaaggag caattaaagg tactgtctaa tcctgacctg    300

ttggaatttg cttccggtct ggttcgcttt gaggctcgaa ttgaaacgcg atatttgaag    360

tctttcgggc ttcctcttaa tctttttgat gcaattcgct ttgcttctga ctataataga    420

cagggtaaag acctgatttt tgatttatgg tcattctcgt tttctgaact gtttaaagca    480

tttgaggggg attcaatgaa tatttatgac gattccgcag tattggacgc tatccagtct    540

aaacatttta caattacccc ctctggcaaa acttcctttg caaaagcctc tcgctatttt    600

ggtttctatc gtcgtctggt taatgagggt tatgatagtg ttgctcttac catgcctcgt    660

aattcctttt ggcgttatgt atctgcatta gttgagtgtg gtattcctaa atctcaattg    720

atgaatcttt ccacctgtaa taatgttgtt ccgttagttc gttttattaa cgtagatttt    780

tcctcccaac gtcctgactg gtataatgag ccagttctta aaatcgcata aggtaattca    840

aaatgattaa agttgaaatt aaaccgtctc aagcgcaatt tactacccgt tctggtgttt    900

ctcgtcaggg caagccttat tcactgaatg agcagctttg ttacgttgat ttgggtaatg    960

aatatccggt gcttgtcaag attactctcg acgaaggtca gccagcgtat gcgcctggtc   1020

tgtacaccgt gcatctgtcc tcgttcaaag ttggtcagtt cggttctctt atgattgacc   1080

gtctgcgcct cgttccggct aagtaacatg gagcaggtcg cggatttcga cacaatttat   1140

caggcgatga tacaaatctc cgttgtactt tgtttcgcgc ttggtataat cgctgggggt   1200

caaagatgag tgttttagtg tattctttcg cctctttcgt tttaggttgg tgccttcgta   1260

gtggcattac gtattttacc cgtttaatgg aaacttcctc atgaaaaagt ctttagtcct   1320

caaagcctcc gtagccgttg ctaccctcgt tccgatgctg tctttcgctg ctgagggtga   1380

cgatcccgca aaagcggcct ttgactccct gcaagcctca gcgaccgaat atatcggtta   1440

tgcgtgggcg atggttgttg tcattgtcgg cgcaactatc ggtatcaagc tgtttaagaa   1500

attcacctcg aaagcaagct gataaaccga tacaattaaa ggctcctttt ggagcctttt   1560

tttttggaga ttttcaacgt gaaaaaatta ttattcgcaa ttcctttagt tgttcctttc   1620

tattctcact cggccgacgt ggcctggcct ctggggccga aactgttgaa agttgtttag   1680

caaaacctca tacagaaaat tcatttacta acgtctggaa agacgacaaa actttagatc   1740

gttacgctaa ctatgagggc tgtctgtgga atgctacagg cgttgtggtt tgtactggtg   1800

acgaaactca gtgttacggt acatgggttc ctattgggct tgctatccct gaaaatgagg   1860

gtggtggctc tgagggtggc ggttctgagg gtggcggttc tgagggtggc ggtactaaac   1920

ctcctgagta cggtgataca cctattccgg gctatactta tatcaaccct ctcgacggca   1980

cttatccgcc tggtactgag caaaaccccg ctaatcctaa tccttctctt gaggagtctc   2040

agcctcttaa tactttcatg tttcagaata ataggttccg aaataggcag ggtgcattaa   2100
```

```
ctgtttatac gggcactgtt actcaaggca ctgaccccgt taaaacttat taccagtaca   2160
ctcctgtatc atcaaaagcc atgtatgacg cttactggaa cggtaaattc agagactgcg   2220
ctttccattc tggctttaat gaggatccat tcgtttgtga atatcaaggc caatcgtctg   2280
acctgcctca acctcctgtc aatgctggcg gcggctctgg tggtggttct ggtggcggct   2340
ctgagggtgg cggctctgag ggtggcggtt ctgagggtgg cggctctgag ggtggcggtt   2400
ccggtggcgg ctccggttcc ggtgattttg attatgaaaa aatggcaaac gctaataagg   2460
gggctatgac cgaaaatgcc gatgaaaacg cgctacagtc tgacgctaaa ggcaaacttg   2520
attctgtcgc tactgattac ggtgctgcta tcgatggttt cattggtgac gtttccggcc   2580
ttgctaatgg taatggtgct actggtgatt ttgctggctc taattcccaa atggctcaag   2640
tcggtgacgg tgataattca cctttaatga ataatttccg tcaatattta ccttctttgc   2700
ctcagtcggt tgaatgtcgc ccttatgtct ttggcgctgg taaaccatat gaattttcta   2760
ttgattgtga caaaataaac ttattccgtg gtgtctttgc gtttctttta tatgttgcca   2820
cctttatgta tgtattttcg acgtttgcta acatactgcg taataaggag tcttaatcat   2880
gccagttctt ttgggtattc cgttattatt gcgtttcctc ggtttccttc tggtaacttt   2940
gttcggctat ctgcttactt tccttaaaaa gggcttcggt aagatagcta ttgctatttc   3000
attgtttctt gctcttatta ttgggcttaa ctcaattctt gtgggttatc tctctgatat   3060
tagcgcacaa ttaccctctg attttgttca gggcgttcag ttaattctcc cgtctaatgc   3120
gcttccctgt ttttatgtta ttctctctgt aaaggctgct attttcattt ttgacgttaa   3180
acaaaaaatc gtttcttatt tggattggga taaataaata tggctgttta ttttgtaact   3240
ggcaaattag gctctggaaa gacgctcgtt agcgttggta agattcagga taaaattgta   3300
gctgggtgca aaatagcaac taatcttgat ttaaggcttc aaaacctccc gcaagtcggg   3360
aggttcgcta aaacgcctcg cgttcttaga ataccggata agccttctat ttctgatttg   3420
cttgctattg gtcgtggtaa tgattcctac gacgaaaata aaaacggttt gcttgttctt   3480
gatgaatgcg gtacttggtt taatacccgt tcatggaatg acaaggaaag acagccgatt   3540
attgattggt ttcttcatgc tcgtaaattg ggatgggata ttatttttct tgttcaggat   3600
ttatctattg ttgataaaca ggcgcgttct gcattagctg aacacgttgt ttattgtcgc   3660
cgtctggaca gaattacttt accctttgtc ggcactttat attctcttgt tactggctca   3720
aaaatgcctc tgcctaaatt acatgttggt gttgttaaat atggtgattc tcaattaagc   3780
cctactgttg agcgttggct ttatactggt aagaatttat ataacgcata tgacactaaa   3840
caggcttttt ccagtaatta tgattcaggt gtttattcat atttaacccc ttatttatca   3900
cacggtcggt atttcaaacc attaaattta ggtcagaaga tgaaattaac taaaatatat   3960
ttgaaaaagt tttctcgcgt tctttgtctt gcgataggat ttgcatcagc atttacatat   4020
agttatataa cccaacctaa gccggaggtt aaaaaggtag tctctcagac ctatgatttt   4080
gataaattca ctattgactc ttctcagcgt cttaatctaa gctatcgcta tgttttcaag   4140
gattctaagg gaaaattaat taatagcgac gatttacaga agcaaggtta ttccatcaca   4200
tatattgatt tatgtactgt ttcaattaaa aaaggtaatt caaatgaaat tgttaaatgt   4260
aattaatttt gttttcttga tgtttgtttc atcatcttct tttgctcaag taattgaaat   4320
gaataattcg cctctgcgcg atttcgtgac ttggtattca aagcaaacag gtgaatctgt   4380
tattgtctca cctgatgtta aaggtacagt gactgtatat tcctctgacg ttaagcctga   4440
```

```
aaatttacgc aatttcttta tctctgtttt acgtgctaat aattttgata tggttggctc   4500
aattccttcc ataattcaga aatataaccc aaatagtcag gattatattg atgaattgcc   4560
atcatctgat attcaggaat atgatgataa ttccgctcct tctggtggtt tctttgttcc   4620
gcaaaatgat aatgttactc aaacatttaa aattaataac gttcgcgcaa aggatttaat   4680
aagggttgta gaattgtttg ttaaatctaa tacatctaaa tcctcaaatg tattatctgt   4740
tgatggttct aacttattag tagttagcgc ccctaaagat attttagata accttccgca   4800
atttctttct actgttgatt tgccaactga ccagatattg attgaaggat taattttcga   4860
ggttcagcaa ggtgatgctt tagatttttc ctttgctgct ggctctcagc gcggcactgt   4920
tgctggtggt gttaatactg accgtctaac ctctgtttta tcttctgcgg gtggttcgtt   4980
cggtattttt aacggcgatg ttttagggct atcagttcgc gcattaaaga ctaatagcca   5040
ttcaaaaata ttgtctgtgc ctcgtattct tacgctttca ggtcagaagg gttctatttc   5100
tgttggccag aatgtccctt ttattactgg tcgtgtaact ggtgaatctg ccaatgtaaa   5160
taatccattt cagacggttg agcgtcaaaa tgttggtatt tctatgagtg tttttcccgt   5220
tgcaatggct ggcggtaata ttgttttaga tataaccagt aaggccgata gtttgagttc   5280
ttctactcag gcaagtgatg ttattactaa tcaaagaagt attgcgacaa cggttaattt   5340
gcgtgatggt cagactcttt tgctcggtgg cctcactgat tacaaaaaca cttctcaaga   5400
ttctggtgtg ccgttcctgt ctaaaatccc tttaatcggc ctcctgttta gctcccgttc   5460
tgattctaac gaggaaagca cgttgtacgt gctcgtcaaa gcaaccatag tacgcgccct   5520
gtagcggcgc attaagcgcg gcgggtgtgg tggttacgcg cagcgtgacc gctacacttg   5580
ccagcgccct agcgcccgct cctttcgctt tcttcccttc ctttctcgcc acgttctccg   5640
gctttccccg tcaagctcta aatcggggga tctcgggaaa agcgttggtg accaaaggtg   5700
ccttttatca tcactttaaa aataaaaaac aattactcag tgcctgttat aagcagcaat   5760
taattatgat tgatgcctac atcacaacaa aaactgattt aacaaatggt tggtctgcct   5820
tagaaagtat atttgaacat tatcttgatt atattattga taataataaa aaccttatcc   5880
ctatccaaga agtgatgcct atcattggtt ggaatgaact tgaaaaaatt agccttgaat   5940
acattactgg taaggtaaac gccattgtca gcaaattgat ccaagagaac caacttaaag   6000
cttatgatga tgatgtgctt aaaaacttac tcaatggctg gtttatgcat atcgcaatac   6060
atgcgaaaaa cctaaaagag cttgccgata aaaaaggcca atttattgct atttaccgcg   6120
gctttttatt gagcttgaaa gataaataaa atagataggt tttatttgaa gctaaatctt   6180
ctttatcgta aaaaatgccc tcttgggtta tcaagagggt cattatattt cgcggaataa   6240
catcatttgg tgacgaaata actaagcact tgtctcctgt ttactcccct gagcttgagg   6300
ggttaacatg aaggtcatcg atagcaggat aataatacag taaaacgcta aaccaataat   6360
ccaaatccag ccatcccaaa ttggtagtga atgattataa ataacagcaa acagtaatgg   6420
gccaataaca ccggttgcat tggtaaggct caccaataat ccctgtaaag caccttgctg   6480
atgactcttt gtttggatag acatcactcc ctgtaatgca ggtaaagcga tcccaccacc   6540
agccaataaa attaaaacag ggaaaactaa ccaaccttca gatataaacg ctaaaaaggc   6600
aaatgcacta ctatctgcaa taaatccgag cagtactgcc gtttttttcgc cccatttagt   6660
ggctattctt cctgccacaa aggcttggaa tactgagtgt aaaagaccaa gacccgctaa   6720
tgaaaagcca accatcatgc tattccatcc aaaacgattt tcggtaaata gcacccacac   6780
cgttgcggga atttggccta tcaattgcgc tgaaaaataa ataatcaaca aaatgggcat   6840
```

```
cgttttaaat aaagtgatgt ataccgaatt cgattgcgtc tcaaccccta cttcggtatc   6900
tgtattatca cgtgtatttt tggtttcacg gaaccaaaac ataaccacaa ggaaagtgac   6960
aatatttagc aacgcagcga taaaaaaggg actatgcggt gaaatctctc ctgcaaaacc   7020
accaataata ggccccgcta ttaaaccaag cccaaaactt gcccctaacc aaccgaacca   7080
cttcacgcgt tgagaagctg aggtggtatc ggcaatgacc gatgccgcga cagccccagt   7140
agctcctgtg atccctgaaa gcaaacggcc taaatacagc atccaaagcg cacttgaaaa   7200
agccagcaat aagtaatcca gcgatgcgcc tattaatgac aacaacagca ctgggcgccg   7260
accaaatcgg tcagacattt ttccaagcca aggagcaaag ataacctgca ttaacgcata   7320
aagtgcaagc aatacgccaa agtggttagc gatatcttcc gaagcaataa attcacgtaa   7380
taacgttggc aagactggca tgataaggcc aatccccatg gcatcgagta acgtaattac   7440
caatgcgatc tttgtcgaac tattcatttc acttttctct atcactgata gggagtggta   7500
aaataactct atcaatgata gagtgtcaac aaaaattagg aattaatgat gtctagatta   7560
gataaaagta aagtgattaa cagcgcatta gagctgctta atgaggtcgg aatcgaaggt   7620
ttaacaaccc gtaaactcgc ccagaagcta ggtgtagagc agcctacatt gtattggcat   7680
gtaaaaaata agcgggcttt gctcgacgcc ttagccattg agatgttaga taggcaccat   7740
actcactttt gccctttaga aggggaaagc tggcaagatt ttttacgtaa taacgctaaa   7800
agttttagat gtgctttact aagtcatcgc gatggagcaa aagtacattt aggtacacgg   7860
cctacagaaa aacagtatga aactctcgaa aatcaattag cctttttatg ccaacaaggt   7920
ttttcactag agaatgcatt atatgcactc agcgctgtgg ggcattttac tttaggttgc   7980
gtattggaag atcaagagca tcaagtcgct aaagaagaaa gggaaacacc tactactgat   8040
agtatgccgc cattattacg acaagctatc gaattatttg atcaccaagg tgcagagcca   8100
gccttcttat tcggccttga attgatcata tgcggattag aaaaacaact taaatgtgaa   8160
agtgggtctt aaaagcagca taaccttttt ccgtgatggt aacttcacgg taaccaagat   8220
gtcgagttaa ccaccccttta gattcataaa gcgaaaataa tgcggctcca acgtacccac   8280
ctaaatggaa acggcgttca ctccaatcta aacacgcaca acagatttta cgtgaatgtt   8340
tggaaggaac gtcaattccc atttcatgaa aatattgaat accacttaat gtgatcattg   8400
aaccattttc agtgatccat tgctgttgac aaagggaatc atagatccct ttagggttcc   8460
gatttagtgc tttacggcac ctcgacctcc aaaaacttga tttgggtgat ggttcacgta   8520
gtgggccatc gccctgatag acggtttttc gccctttgac gttggagtcc acgttcttta   8580
atagtggact cttgttccaa actggaacaa cactcacaac taactcggcc tattcttttg   8640
atttataagg atttttgtca ttttctgctt actggttaaa aaataagctg atttaacaaa   8700
tatttaacgc gaaatttaac aaaacattaa cgtttacaat ttaaatattt gcttatacaa   8760
tcatcctgtt tttggggctt ttctgattat caatcggggt acatatgatt gacatgctag   8820
ttttacgatt accgttcatc gattctcttg tttgctccag actttcaggt aatgacctga   8880
tagcctttgt agacctctca aaaatagcta ccctctccgg catgaattta tcagctagaa   8940
cggttgaata tcatattgac ggtgatttga ctgtctccgg cctttctcac ccgtttgaat   9000
ctttgcctac tcattactcc ggcattgcat ttaaaatata tgagggttct aaaaattttt   9060
atccctgcgt tgaaattaag gcttcaccag caaaagtatt acagggtcat aatgtttttg   9120
gtacaaccga tttagcttta tgctctgagg ctttattgct taattttgct aactctctgc   9180
```

cttgcttgta cgatttattg gatgtt 9206

<210> SEQ ID NO 31
<211> LENGTH: 8669
<212> TYPE: DNA
<213> ORGANISM: Artificial
<220> FEATURE:
<223> OTHER INFORMATION: Cloning vector M13KO7, complete sequence

<400> SEQUENCE: 31
aacgctacta ctattagtag aattgatgcc accttttcag ctcgcgcccc aaatgaaaat 60
atagctaaac aggttattga ccatttgcga aatgtatcta atggtcaaac taaatctact 120
cgttcgcaga attgggaatc aactgttaca tggaatgaaa cttccagaca ccgtacttta 180
gttgcatatt taaaacatgt tgagctacag caccagattc agcaattaag ctctaagcca 240
tccgcaaaaa tgacctctta tcaaaaggag caattaaagg tactctctaa tcctgacctg 300
ttggagtttg cttccggtct ggttcgcttt gaagctcgaa ttaaaacgcg atatttgaag 360
tctttcgggc ttcctcttaa tctttttgat gcaatccgct ttgcttctga ctataatagt 420
cagggtaaag acctgatttt tgatttatgg tcattctcgt tttctgaact gtttaaagca 480
tttgaggggg attcaatgaa tatttatgac gattccgcag tattggacgc tatccagtct 540
aaacatttta ctattacccc ctctggcaaa acttcttttg caaaagcctc tcgctatttt 600
ggtttttatc gtcgtctggt aaacgagggt tatgatagtg ttgctcttac tatgcctcgt 660
aattcctttt ggcgttatgt atctgcatta gttgaatgtg gtattcctaa atctcaactg 720
atgaatcttt ctacctgtaa taatgttgtt ccgttagttc gttttattaa cgtagatttt 780
tcttcccaac gtcctgactg gtataatgag ccagttctta aaatcgcata aggtaattca 840
caatgattaa agttgaaatt aaaccatctc aagcccaatt tactactcgt tctggtgttt 900
ctcgtcaggg caagccttat tcactgaatg agcagctttg ttacgttgat ttgggtaatg 960
aatatccggt tcttgtcaag attactcttg atgaaggtca gccagcctat gcgcctggtc 1020
tgtacaccgt tcatctgtcc tctttcaaag ttggtcagtt cggttccctt atgattgacc 1080
gtctgcgcct cgttccggct aagtaacatg gagcaggtcg cggatttcga cacaatttat 1140
caggcgatga tacaaatctc cgttgtactt tgtttcgcgc ttggtataat cgctgggggt 1200
caaagatgag tgttttagtg tattctttcg cctctttcgt tttaggttgg tgccttcgta 1260
gtggcattac gtattttacc cgtttaatgg aaacttcctc atgaaaaagt ctttagtcct 1320
caaagcctct gtagccgttg ctaccctcgt tccgatgctg tctttcgctg ctgagggtga 1380
cgatcccgca aaagcggcct ttaactccct gcaagcctca gcgaccgaat atatcggtta 1440
tgcgtgggcg atggttgttg tcattgtcgg cgcaactatc ggtatcaagc tgtttaagaa 1500
attcacctcg aaagcaagct gataaaccga tacaattaaa ggctcctttt ggagcctttt 1560
tttttggaga ttttcaacgt gaaaaaatta ttattcgcaa ttcctttagt tgttcctttc 1620
tattctcact ccgctgaaac tgttgaaagt tgtttagcaa aaccccatac agaaaattca 1680
tttactaacg tctggaaaga cgacaaaact ttagatcgtt acgctaacta tgagggttgt 1740
ctgtggaatg ctacaggcgt tgtagtttgt actggtgacg aaactcagtg ttacggtaca 1800
tgggttccta ttgggcttgc tatccctgaa aatgagggtg gtggctctga gggtggcggt 1860
tctgagggtg gcggttctga gggtggcggt actaaacctc ctgagtacgg tgatacacct 1920
attccgggct atacttatat caaccctctc gacggcactt atccgcctgg tactgagcaa 1980
aaccccgcta atcctaatcc ttctcttgag gagtctcagc ctcttaatac tttcatgttt 2040

-continued

```
cagaataata ggttccgaaa taggcagggg gcattaactg tttatacggg cactgttact   2100

caaggcactg accccgttaa aacttattac cagtacactc ctgtatcatc aaaagccatg   2160

tatgacgctt actggaacgg taaattcaga gactgcgctt tccattctgg ctttaatgag   2220

gatccattcg tttgtgaata tcaaggccaa tcgtctgacc tgcctcaacc tcctgtcaat   2280

gctggcggcg gctctggtgg tggttctggt ggcggctctg agggtggtgg ctctgagggt   2340

ggcggttctg agggtggcgg ctctgaggga ggcggttccg gtggtggctc tggttccggt   2400

gattttgatt atgaaaagat ggcaaacgct aataaggggg ctatgaccga aaatgccgat   2460

gaaaacgcgc tacagtctga cgctaaaggc aaacttgatt ctgtcgctac tgattacggt   2520

gctgctatcg atggtttcat tggtgacgtt tccggccttg ctaatggtaa tggtgctact   2580

ggtgattttg ctggctctaa ttcccaaatg gctcaagtcg gtgacggtga taattcacct   2640

ttaatgaata atttccgtca atatttacct tccctccctc aatcggttga atgtcgccct   2700

tttgtcttta gcgctggtaa accatatgaa ttttctattg attgtgacaa aataaactta   2760

ttccgtggtg tctttgcgtt tcttttatat gttgccacct ttatgtatgt attttctacg   2820

tttgctaaca tactgcgtaa taaggagtct taatcatgcc agttcttttg ggtattccgt   2880

tattattgcg tttcctcggt ttccttctgg taactttgtt cggctatctg cttacttttc   2940

ttaaaaaggg cttcggtaag atagctattg ctatttcatt gtttcttgct cttattattg   3000

ggcttaactc aattcttgtg ggttatctct ctgatattag cgctcaatta ccctctgact   3060

ttgttcaggg tgttcagtta attctcccgt ctaatgcgct tccctgtttt tatgttattc   3120

tctctgtaaa ggctgctatt ttcatttttg acgttaaaca aaaaatcgtt tcttatttgg   3180

attgggataa ataatatggc tgtttatttt gtaactggca aattaggctc tggaaagacg   3240

ctcgttagcg ttggtaagat tcaggataaa attgtagctg ggtgcaaaat agcaactaat   3300

cttgatttaa ggcttcaaaa cctcccgcaa gtcgggaggt tcgctaaaac gcctcgcgtt   3360

cttagaatac cggataagcc ttctatatct gatttgcttg ctattgggcg cggtaatgat   3420

tcctacgatg aaaataaaaa cggcttgctt gttctcgatg agtgcggtac ttggtttaat   3480

acccgttctt ggaatgataa ggaaagacag ccgattattg attggtttct acatgctcgt   3540

aaattaggat gggatattat ttttcttgtt caggacttat ctattgttga taaacaggcg   3600

cgttctgcat tagctgaaca tgttgtttat tgtcgtcgtc tggacagaat tactttacct   3660

tttgtcggta ctttatattc tcttattact ggctcgaaaa tgcctctgcc taaattacat   3720

gttggcgttg ttaaatatgg cgattctcaa ttaagcccta ctgttgagcg ttggctttat   3780

actggtaaga atttgtataa cgcatatgat actaaacagg ctttttctag taattatgat   3840

tccggtgttt attcttattt aacgccttat ttatcacacg gtcggtattt caaaccatta   3900

aatttaggtc agaagatgaa attaactaaa atatatttga aaaagttttc tcgcgttctt   3960

tgtcttgcga ttggatttgc atcagcattt acatatagtt atataaccca acctaagccg   4020

gaggttaaaa aggtagtctc tcagacctat gattttgata aattcactat tgactcttct   4080

cagcgtctta atctaagcta tcgctatgtt ttcaaggatt ctaagggaaa attaattaat   4140

agcgacgatt tacagaagca aggttattca ctcacatata ttgatttatg tactgtttcc   4200

attaaaaaag gtaattcaaa tgaaattgtt aaatgtaatt aattttgttt tcttgatgtt   4260

tgtttcatca tcttcttttg ctcaggtaat tgaaatgaat aattcgcctc tgcgcgattt   4320

tgtaacttgg tattcaaagc aatcaggcga atccgttatt gtttctcccg atgtaaaagg   4380
```

```
tactgttact gtatattcat ctgacgttaa acctgaaaat ctacgcaatt tctttatttc   4440
tgttttacgt gctaataatt ttgatatggt tggttcaatt ccttccataa ttcagaagta   4500
taatccaaac aatcaggatt atattgatga attgccatca tctgataatc aggaatatga   4560
tgataattcc gctccttctg gtggtttctt tgttccgcaa aatgataatg ttactcaaac   4620
ttttaaaatt aataacgttc gggcaaagga tttaatacga gttgtcgaat tgtttgtaaa   4680
gtctaatact tctaaatcct caaatgtatt atctattgac ggctctaatc tattagttgt   4740
tagtgcacct aaagatattt tagataacct tcctcaattc ctttctactg ttgatttgcc   4800
aactgaccag atattgattg agggtttgat atttgaggtt cagcaaggtg atgctttaga   4860
tttttcattt gctgctggct ctcagcgtgg cactgttgca ggcggtgtta atactgaccg   4920
cctcacctct gttttatctt ctgctggtgg ttcgttcggt atttttaatg gcgatgtttt   4980
agggctatca gttcgcgcat taaagactaa tagccattca aaaatattgt ctgtgccacg   5040
tattcttacg ctttcaggtc agaagggttc tatctctgtt ggccagaatg tccctttttat   5100
tactggtcgt gtgactggtg aatctgccaa tgtaaataat ccatttcaga cgattgagcg   5160
tcaaaatgta ggtatttcca tgagcgtttt tcctgttgca atggctggcg gtaatattgt   5220
tctggatatt accagcaagg ccgatagttt gagttcttct actcaggcaa gtgatgttat   5280
tactaatcaa agaagtattg ctacaacggt taatttgcgt gatggacaga ctcttttact   5340
cggtggcctc actgattata aaaacacttc tcaagattct ggcgtaccgt tcctgtctaa   5400
aatcccttta atcggcctcc tgtttagctc ccgctctgat tccaacgagg aaagcacgtt   5460
atacgtgctc gtcaaagcaa ccatagtacg cgccctgtag cggcgcatta agcgcggcgg   5520
gtgtggtggt tacgcgcagc gtgaccgcta cacttgccag cgccctagcg cccgctcctt   5580
tcgctttctt cccttccttt ctcgccacgt tcgccggctt tccccgtcaa gctctaaatc   5640
gggggctccc tttagggttc cgatttagtg ctttacggca cctcgacccc aaaaaacttg   5700
atttgggtga tggttcacgt agtgggccat cgccctgata gacggttttt cgccctttga   5760
cgttggagtc cacgttcttt aatagtggac tcttgttcca aactggaaca acactcaacc   5820
ctatctcggg acggatcgct tcatgtggca ggagaaaaaa ggctgcaccg gtgcgtcagc   5880
agaatatgtg atacaggata tattccgctt cctcgctcac tgactcgcta cgctcggtcg   5940
ttcgactgcg gcgagcggaa atggcttacg aacggggcgg agatttcctg gaagatgcca   6000
ggaagatact taacagggaa gtgagagggc cgcggcaaag ccgtttttcc ataggctccg   6060
cccccctgac aagcatcacg aaatctgacg ctcaaatcag tggtggcgaa acccgacagg   6120
actataaaga taccaggcgt ttccccctgg cggctccctc gtgcgctctc ctgttcctgc   6180
ctttcggttt accggtgtca ttccgctgtt atggccgcgt ttgtctcatt ccacgcctga   6240
cactcagttc cgggtaggca gttcgctcca agctggactg tatgcacgaa ccccccgttc   6300
agtccgaccg ctgcgcctta tccggtaact atcgtcttga gtccaacccg gaaagacatg   6360
caaaagcacc actggcagca gccactggta attgatttag aggagttagt cttgaagtca   6420
tgcgccggtt aaggctaaac tgaaaggaca agttttggtg actgcgctcc tccaagccag   6480
ttacctcggt tcaaagagtt ggtagctcag agaaccttcg aaaaaccgcc ctgcaaggcg   6540
gtttttttcgt tttcagagca agagattacg cgcagaccaa aacgatctca agaagatcat   6600
cttattaagg ggtctgacgc tcagtggaac gaaaactcac gttaagggat tttggtcatg   6660
agattatcaa aaaggatctt cacctagatc cttttaaatt aaaaatgaag ttttaaatca   6720
atctaaagta tatatgagta aacttggtct gacagttacc aatgcttaat cagtgaggca   6780
```

```
cctatctcag cgatctgtct atttcgttca tccatagttg cctgactccc cgtcgtgtag   6840

ataactacga tacgggaggg cttaccatct ggccccagtg ctgcaatgat accgcgagac   6900

ccacgctcac cggctccaga tttatcagca ataaaccagc cagccgattc gagctcgccc   6960

cggggatcga ccagttggtg attttgaact tttgctttgc cacggaacgg tctgcgttgt   7020

cgggaagatg cgtgatctga tccttcaact cagcaaaagt tcgatttatt caacaaagcc   7080

gccgtcccgt caagtcagcg taatgctctg ccagtgttac aaccaattaa ccaattctga   7140

ttagaaaaac tcatcgagca tcaaatgaaa ctgcaattta ttcatatcag gattatcaat   7200

accatatttt tgaaaaagcc gtttctgtaa tgaaggagaa aactcaccga ggcagttcca   7260

taggatggca agatcctggt atcggtctgc gattccgact cgtccaacat caatacaacc   7320

tattaatttc ccctcgtcaa aaataaggtt atcaagtgag aaatcaccat gagtgacgac   7380

tgaatccggt gagaatggca aaagcttatg catttctttc cagacttgtt caacaggcca   7440

gccattacgc tcgtcatcaa aatcactcgc atcaaccaaa ccgttattca ttcgtgattg   7500

cgcctgagcg agacgaaata cgcgatcgct gttaaaagga caattacaaa caggaatcga   7560

atgcaaccgg cgcaggaaca ctgccagcgc atcaacaata ttttcacctg aatcaggata   7620

ttcttctaat acctggaatg ctgttttccc ggggatcgca gtggtgagta accatgcatc   7680

atcaggagta cggataaaat gcttgatggt cggaagaggc ataaattccg tcagccagtt   7740

tagtctgacc atctcatctg taacatcatt ggcaacgcta cctttgccat gtttcagaaa   7800

caactctggc gcatcgggct tcccatacaa tcgatagatt gtcgcacctg attgcccgac   7860

attatcgcga gcccatttat acccatataa atcagcatcc atgttggaat ttaatcgcgg   7920

cctcgagcaa gacgtttccc gttgaatatg gctcataaca ccccttgtat tactgtttat   7980

gtaagcagac agttttattg ttcatgatga tatattttta tcttgtgcaa tgtaacatca   8040

gagattttga gacacaacgt ggctttcccc ccccccccct gcaggtctcg ggctattctt   8100

ttgatttata agggattttg ccgatttcgg cctattggtt aaaaaatgag ctgatttaac   8160

aaaaatttaa cgcgaatttt aacaaaatat taacgtttac aatttaaata tttgcttata   8220

caatcttcct gtttttgggg cttttctgat tatcaaccgg ggtacatatg attgacatgc   8280

tagttttacg attaccgttc atcgattctc ttgtttgctc cagactctca ggcaatgacc   8340

tgatagcctt tgtagacctc tcaaaaatag ctaccctctc cggcatgaat ttatcagcta   8400

gaacggttga atatcatatt gatggtgatt tgactgtctc cggcctttct caccctttg   8460

aatctttacc tacacattac tcaggcattg catttaaaat atatgagggt tctaaaaatt   8520

tttatccttg cgttgaaata aaggcttctc ccgcaaaagt attacagggt cataatgttt   8580

ttggtacaac cgatttagct ttatgctctg aggctttatt gcttaatttt gctaattctt   8640

tgccttgcct gtatgattta ttggatgtt                                     8669
```

<210> SEQ ID NO 32
<211> LENGTH: 8669
<212> TYPE: DNA
<213> ORGANISM: Artificial
<220> FEATURE:
<223> OTHER INFORMATION: VCSM13 interference-resistant helper phage, complete genome.

<400> SEQUENCE: 32

```
tgcctgactc cccgtcgtgt agataactac gatacgggag ggcttaccat ctggccccag     60

tgctgcaatg ataccgcgag acccacgctc accggctcca gatttatcag caataaacca    120
```

-continued

```
gccagccgat tcgagctcgc ccggggatcg accagttggt gattttgaac ttttgctttg    180
ccacggaacg gtctgcgttg tcgggaagat gcgtgatctg atccttcaac tcagcaaaag    240
ttcgatttat tcaacaaagc cgccgtcccg tcaagtcagc gtaatgctct gccagtgtta    300
caaccaatta accaattctg attagaaaaa ctcatcgagc atcaaatgaa actgcaattt    360
attcatatca ggattatcaa taccatattt ttgaaaaagc cgtttctgta atgaaggaga    420
aaactcaccg aggcagttcc ataggatggc aagatcctgg tatcggtctg cgattccgac    480
tcgtccaaca tcaatacaac ctattaattt cccctcgtca aaaataaggt tatcaagtga    540
gaaatcacca tgagtgacga ctgaatccgg tgagaatggc aaaagcttat gcatttcttt    600
ccagacttgt tcaacaggcc agccattacg ctcgtcatca aaatcactcg catcaaccaa    660
accgttattc attcgtgatt gcgcctgagc gagacgaaat acgcgatcgc tgttaaaagg    720
acaattacaa acaggaatcg aatgcaaccg gcgcaggaac actgccagcg catcaacaat    780
attttcacct gaatcaggat attcttctaa tacctggaat gctgttttcc cggggatcgc    840
agtggtgagt aaccatgcat catcaggagt acggataaaa tgcttgatgg tcggaagagg    900
cataaattcc gtcagccagt ttagtctgac catctcatct gtaacatcat tggcaacgct    960
acctttgcca tgtttcagaa acaactctgg cgcatcgggc ttcccataca atcgatagat   1020
tgtcgcacct gattgcccga cattatcgcg agcccattta tacccatata aatcagcatc   1080
catgttggaa tttaatcgcg gcctcgagca agacgtttcc cgttgaatat ggctcataac   1140
cccccttgta ttactgttta tgtaagcaga cagttttatt gttcatgatg atatattttt   1200
atcttgtgca atgtaacatc agagattttg aaacacaacg tggctttccc cccccccccc   1260
ctgcaggtct cgggctattc ttttgattta taagggattt tgccgatttc ggcctattgg   1320
ttaaaaaatg agctgattta acaaaaattt aacgcgaatt ttaacaaaat attaacgttt   1380
acaatttaaa tatttgctta tacaatcttc ctgtttttgg ggcttttctt attatcaacc   1440
ggggtacata tgattgacat gctagtttta cgattaccgt tcatcgattc tcttgtttgc   1500
tccagactct caggcaatga cctgatagcc tttgtagacc tctcaaaaat agctaccctc   1560
tccggcatga atttatcagc tagaacggtt gaatatcatg ttgatggtga tttgactgtc   1620
tccggccttt ctcacccttt tgaatcttta cctacacatt actcaggcat tgcatttaaa   1680
atatatgagg gttctaaaaa tttttatcct tgcgttgaaa taaaggcttc tcccgcaaaa   1740
gtattacagg gtcataatgt ttttggtaca accgatttag ctttatgctc tgaggcttta   1800
ttgcttaatt ttgctaattc tttgccttgc ctgtatgatt tattggatgt taacgctact   1860
actattagta gaattgatgc caccttttca gctcgcgccc caaatgaaaa tatagctaaa   1920
caggttattg accatttgcg aaatgtatct aatggtcaaa ctaaatctac tcgttcgcag   1980
aattgggaat caactgttac atggaatgaa acttccagac accgtacttt agttgcatat   2040
ttaaaacatg ttgagctaca gcaccagatt cagcaattaa gctctaagcc atccgcaaaa   2100
atgacctctt atcaaaagga gcaattaaag gtactctcta atcctgacct gttggagttt   2160
gcttccggtc tggttcgctt tgaagctcga attaaaacgc gatatttgaa gtctttcggg   2220
cttcctctta atctttttga tgcaatccgc tttgcttctg actataatag tcagggtaaa   2280
gacctgattt ttgatttatg gtcattctcg ttttctgaac tgtttaaagc atttgagggg   2340
gattcaatga atatttatga cgattccgca gtattggacg ctatccagtc taaacatttt   2400
actattaccc cctctggcaa aacttctttt gcaaaagcct ctcgctattt tggtttttat   2460
```

```
cgtcgtctgg taaacgaggg ttatgatagt gttgctctta ctatgcctcg taattccttt   2520
tggcgttatg tatctgcatt agttgaatgt ggtattccta aatctcaact gatgaatctt   2580
tctacctgta ataatgttgt tccgttagtt cgttttatta acgtagattt ttcttcccaa   2640
cgtcctgact ggtataatga gccagttctt aaaatcgcat aaggtaattc acaatgatta   2700
aagttgaaat taaaccatct caagcccaat ttactactcg ttctggtgtt tctcgtcagg   2760
gcaagcctta ttcactgaat gagcagcttt gttacgttga tttgggtaat gaatatccgg   2820
ttcttgtcaa gattactctt gatgaaggtc agccagccta tgcgcctggt ctgtacaccg   2880
ttcatctgtc ctctttcaaa gttggtcagt tcggttccct tatgattgac cgtctgcgcc   2940
tcgttccggc taagtaacat ggagcaggtc gcggatttcg acacaattta tcaggcgatg   3000
atacaaatct ccgttgtact ttgtttcgcg cttggtataa tcgctggggg tcaaagatga   3060
gtgttttagt gtattctttc gcctctttcg ttttaggttg gtgccttcgt agtggcatta   3120
cgtattttac ccgtttaatg gaaacttcct catgaaaaag tctttagtcc tcaaagcctc   3180
tgtagccgtt gctaccctcg ttccgatgct gtctttcgct gctgagggtg acgatcccgc   3240
aaaagcggcc tttaactccc tgcaagcctc agcgaccgaa tatatcggtt atgcgtgggc   3300
gatggttgtt gtcattgtcg gcgcaactat cggtatcaag ctgtttaaga aattcacctc   3360
gaaagcaagc tgataaaccg atacaattaa aggctccttt tggagccttt tttttggag    3420
attttcaacg tgaaaaaatt attattcgca attcctttag ttgttccttt ctattctcac   3480
tccgctgaaa ctgttgaaag ttgtttagca aaaccccata cagaaaattc atttactaac   3540
gtctggaaag acgacaaaac tttagatcgt tacgctaact atgagggctg tctgtggaat   3600
gctacaggcg ttgtagtttg tactggtgac gaaactcagt gttacggtac atgggttcct   3660
attgggcttg ctatccctga aaatgagggt ggtggctctg agggtggcgg ttctgagggt   3720
ggcggttctg agggtggcgg tactaaacct cctgagtacg gtgatacacc tattccgggc   3780
tatacttata tcaaccctct cgacggcact tatccgcctg gtactgagca aaaccccgct   3840
aatcctaatc cttctcttga ggagtctcag cctcttaata ctttcatgtt tcagaataat   3900
aggttccgaa ataggcaggg ggcattaact gtttatacgg gcactgttac tcaaggcact   3960
gaccccgtta aaacttatta ccagtacact cctgtatcat caaaagccat gtatgacgct   4020
tactggaacg gtaaattcag agactgcgct ttccattctg gctttaatga ggatccattc   4080
gtttgtgaat atcaaggcca atcgtctgac ctgcctcaac ctcctgtcaa tgctggcggc   4140
ggctctggtg gtggttctgg tggcggctct gagggtggtg gctctgaggg tggcggttct   4200
gagggtggcg gctctgaggg aggcggttcc ggtggtggct ctggttccgg tgattttgat   4260
tatgaaaaga tggcaaacgc taataagggg gctatgaccg aaaatgccga tgaaaacgcg   4320
ctacagtctg acgctaaagg caaacttgat tctgtcgcta ctgattacgg tgctgctatc   4380
gatggtttca ttggtgacgt ttccggcctt gctaatggta atggtgctac tggtgatttt   4440
gctggctcta attcccaaat ggctcaagtc ggtgacggtg ataattcacc tttaatgaat   4500
aatttccgtc aatatttacc ttccctccct caatcggttg aatgtcgccc ttttgtcttt   4560
ggcgctggta aaccatatga attttctatt gattgtgaca aaataaactt attccgtggt   4620
gtctttgcgt ttcttttata tgttgccacc tttatgtatg tattttctac gtttgctaac   4680
atactgcgta ataaggagtc ttaatcatgc cagttctttt gggtattccg ttattattgc   4740
gtttcctcgg tttccttctg gtaactttgt tcggctatct gcttactttt cttaaaaagg   4800
gcttcggtaa gatagctatt gctatttcat tgtttcttgc tcttattatt gggcttaact   4860
```

-continued

```
caattcttgt gggttatctc tctgatatta gcgctcaatt accctctgac tttgttcagg   4920
gtgttcagtt aattctcccg tctaatgcgc ttccctgttt ttatgttatt ctctctgtaa   4980
aggctgctat tttcattttt gacgttaaac aaaaaatcgt ttcttatttg gattgggata   5040
aataatatgg ctgtttattt tgtaactggc aaattaggct ctggaaagac gctcgttagc   5100
gttggtaaga ttcaggataa aattgtagct gggtgcaaaa tagcaactaa tcttgattta   5160
aggcttcaaa acctcccgca agtcgggagg ttcgctaaaa cgcctcgcgt tcttagaata   5220
ccggataagc cttctatatc tgatttgctt gctattgggc gcggtaatga ttcctacgat   5280
gaaaataaaa acggcttgct tgttctcgat gagtgcggta cttggtttaa tacccgttct   5340
tggaatgata aggaaagaca gccgattatt gattggtttc tacatgctcg taaattagga   5400
tgggatatta tttttcttgt tcaggactta tctattgttg ataaacaggc gcgttctgca   5460
ttagctgaac atgttgttta ttgtcgtcgt ctggacagaa ttactttacc ttttgtcggt   5520
actttatatt ctcttattac tggctcgaaa atgcctctgc ctaaattaca tgttggcgtt   5580
gttaaatatg gcgattctca attaagccct actgttgagc gttggcttta tactggtaag   5640
aatttgtata acgcatatga tactaaacag gctttttcta gtaattatga ttccggtgtt   5700
tattcttatt taacgcctta tttatcacac ggtcggtatt tcaaaccatt aaatttaggt   5760
cagaagatga aattaactaa aatatatttg aaaaagtttt ctcgcgttct ttgtcttgcg   5820
attggatttg catcagcatt tacatatagt tatataaccc aacctaagcc ggaggttaaa   5880
aaggtagtct ctcagaccta tgattttgat aaattcacta ttgactcttc tcagcgtctt   5940
aatctaagct atcgctatgt tttcaaggat tctaagggaa aattaattaa tagcgacgat   6000
ttacagaagc aaggttattc actcacatat attgatttat gtactgtttc cattaaaaaa   6060
ggtaattcaa atgaaattgt taaatgtaat taattttgtt ttcttgatgt ttgtttcatc   6120
atcttctttt gctcaggtaa ttgaaatgaa taattcgcct ctgcgcgatt ttgtaacttg   6180
gtattcaaag caatcaggcg aatccgttat tgtttctccc gatgtaaaag gtactgttac   6240
tgtatattca tctgacgtta aacctgaaaa tctacgcaat ttctttattt ctgttttacg   6300
tgcaaataat tttgatatgg taggttctaa cccttccatt attcagaagt ataatccaaa   6360
caatcaggat tatattgatg aattgccatc atctgataat caggaatatg atgataattc   6420
cgctccttct ggtggtttct ttgttccgca aaatgataat gttactcaaa cttttaaaat   6480
taataacgtt cgggcaaagg atttaatacg agttgtcgaa ttgtttgtaa agtctaatac   6540
ttctaaatcc tcaaatgtat tatctattga cggctctaat ctattagttg ttagtgctcc   6600
taaagatatt ttagataacc ttcctcaatt cctttcaact gttgatttgc caactgacca   6660
gatattgatt gagggtttga tatttgaggt tcagcaaggt gatgctttag atttttcatt   6720
tgctgctggc tctcagcgtg gcactgttgc aggcggtgtt aatactgacc gcctcacctc   6780
tgttttatct tctgctggtg gttcgttcgg tatttttaat ggcgatgttt tagggctatc   6840
agttcgcgca ttaaagacta atagccattc aaaaatattg tctgtgccac gtattcttac   6900
gctttcaggt cagaagggtt ctatctctgt tggccagaat gtccctttta ttactggtcg   6960
tgtgactggt gaatctgcca atgtaaataa tccatttcag acgattgagc gtcaaaatgt   7020
aggtatttcc atgagcgttt ttcctgttgc aatggctggc ggtaatattg ttctggatat   7080
taccagcaag gccgatagtt tgagttcttc tactcaggca agtgatgtta ttactaatca   7140
aagaagtatt gctacaacgg ttaatttgcg tgatggacag actcttttac tcggtggcct   7200
```

```
cactgattat aaaaacactt ctcaggattc tggcgtaccg ttcctgtcta aaatcccttt   7260

aatcggcctc ctgtttagct cccgctctga ttctaacgag gaaagcacgt tatacgtgct   7320

cgtcaaagca accatagtac gcgccctgta gcggcgcatt aagcgcggcg ggtgtggtgg   7380

ttacgcgcag cgtgaccgct acacttgcca gcgccctagc gcccgctcct ttcgctttct   7440

tcccttcctt tctcgccacg ttcgccggct ttccccgtca agctctaaat cgggggctcc   7500

ctttagggtt ccgatttagt gctttacggc acctcgaccc caaaaaactt gatttgggtg   7560

atggttcacg tagtgggcca tcgccctgat agacggtttt tcgccctttg acgttggagt   7620

ccacgttctt taatagtgga ctcttgttcc aaactggaac aacactcaac cctatctcgg   7680

gacggatcgc ttcatgtggc aggagaaaaa aggctgcacc ggtgcgtcag cagaatatgt   7740

gatacaggat atattccgct tcctcgctca ctgactcgct acgctcggtc gttcgactgc   7800

ggcgagcgga aatggcttac gaacggggcg gagatttcct ggaagatgcc aggaagatac   7860

ttaacaggga agtgagaggg ccgcggcaaa gccgtttttc cataggctcc gcccccctga   7920

caagcatcac gaaatctgac gctcaaatca gtggtggcga aacccgacag gactataaag   7980

ataccaggcg tttccccctg gcggctccct cgtgcgctct cctgttcctg cctttcggtt   8040

taccggtgtc attccgctgt tatggccgcg tttgtctcat tccacgcctg acactcagtt   8100

ccgggtaggc agttcgctcc aagctggact gtatgcacga accccccgtt cagtccgacc   8160

gctgcgcctt atccggtaac tatcgtcttg agtccaaccc ggaaagacat gcaaaagcac   8220

cactggcagc agccactggt aattgattta gaggagttag tcttgaagtc atgcgccggt   8280

taaggctaaa ctgaaaggac aagttttggt gactgcgctc ctccaagcca gttacctcgg   8340

ttcaaagagt tggtagctca gagaaccttc gaaaaaccgc cctgcaaggc ggttttttcg   8400

ttttcagagc aagagattac gcgcagacca aaacgatctc aagaagatca tcttattaag   8460

ggtctgacg ctcagtggaa cgaaaactca cgttaaggga ttttggtcat gagattatca   8520

aaaaggatct tcacctagat ccttttaaat taaaaatgaa gttttaaatc aatctaaagt   8580

atatatgagt aaacttggtc tgacagttac caatgcttaa tcagtgaggc acctatctca   8640

gcgatctgtc tatttcgttc atccatagt                                     8669
```

<210> SEQ ID NO 33
<211> LENGTH: 22
<212> TYPE: PRT
<213> ORGANISM: Artificial
<220> FEATURE:
<223> OTHER INFORMATION: signal sequence

<400> SEQUENCE: 33

```
Met Lys Tyr Leu Leu Pro Thr Ala Ala Ala Gly Leu Leu Leu Leu Ala
1               5                   10                  15

Ala Gln Pro Ala Met Ala
            20
```

<210> SEQ ID NO 34
<211> LENGTH: 42
<212> TYPE: PRT
<213> ORGANISM: Artificial Sequence
<220> FEATURE:
<223> OTHER INFORMATION: Leader Sequence TorA7I

<400> SEQUENCE: 34

```
Met Asn Asn Asn Asp Leu Phe Gln Thr Ser Arg Gln Arg Phe Leu Ala
1               5                   10                  15
```

```
Gln Leu Gly Gly Leu Thr Val Ala Gly Met Leu Gly Pro Ser Leu Leu
            20                  25                  30

Thr Pro Arg Arg Ala Thr Ala Ala Met Ala
        35                  40


<210> SEQ ID NO 35
<211> LENGTH: 45
<212> TYPE: PRT
<213> ORGANISM: Artificial Sequence
<220> FEATURE:
<223> OTHER INFORMATION: Leader Sequence TorA7II

<400> SEQUENCE: 35

Met Asn Asn Asn Asp Leu Phe Gln Thr Ser Arg Gln Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala Ala Met Ala
        35                  40                  45


<210> SEQ ID NO 36
<211> LENGTH: 22
<212> TYPE: PRT
<213> ORGANISM: Artificial Sequence
<220> FEATURE:
<223> OTHER INFORMATION: Leader Sequence pelB

<400> SEQUENCE: 36

Met Lys Tyr Leu Leu Pro Thr Ala Ala Ala Gly Leu Leu Leu Leu Ala
1               5                   10                  15

Ala Gln Pro Ala Met Ala
            20


<210> SEQ ID NO 37
<211> LENGTH: 244
<212> TYPE: PRT
<213> ORGANISM: Artificial Sequence
<220> FEATURE:
<223> OTHER INFORMATION: Recombinant GFP with c-terminal His6- tag

<400> SEQUENCE: 37

Ala Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
```

```
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys His His
225                 230                 235                 240

His His His His


<210> SEQ ID NO 38
<211> LENGTH: 250
<212> TYPE: PRT
<213> ORGANISM: Artificial Sequence
<220> FEATURE:
<223> OTHER INFORMATION: Anti-GFP-scFv

<400> SEQUENCE: 38

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Lys Gly Arg Tyr Asp Phe Trp Ser Gly Gly Pro Phe Asp Tyr Trp
            100                 105                 110

Gly Gln Gly Thr Leu Val Thr Val Ser Ser Lys Leu Ser Gly Ser Ala
        115                 120                 125

Ser Ala Pro Lys Leu Glu Glu Gly Glu Phe Ser Glu Ala Arg Val Ser
    130                 135                 140

Ser Glu Leu Ser Gln Asp Pro Ala Val Ser Val Ala Leu Gly Gln Thr
145                 150                 155                 160

Val Arg Ile Thr Cys Gln Gly Asp Ser Leu Arg Ser Tyr Tyr Ala Ser
                165                 170                 175

Trp Tyr Gln Gln Lys Pro Gly Gln Ala Pro Val Leu Val Ile Tyr Gly
            180                 185                 190

Lys Asn Asn Arg Pro Ser Gly Ile Pro Asp Arg Phe Ser Gly Ser Ser
        195                 200                 205

Ser Gly Asn Thr Ala Ser Leu Thr Ile Thr Gly Ala Gln Ala Glu Asp
    210                 215                 220

Glu Ala Asp Tyr Tyr Cys Asn Ser Arg Asp Ser Ser Gly Asn Trp Val
225                 230                 235                 240

Phe Gly Gly Gly Thr Lys Leu Thr Val Leu
                245                 250


<210> SEQ ID NO 39
```

<211> LENGTH: 50
<212> TYPE: DNA
<213> ORGANISM: Artificial Sequence
<220> FEATURE:
<223> OTHER INFORMATION: GFP-fw

<400> SEQUENCE: 39
ccggccatgg cggctagtaa aggagaagaa cttttcactg gagttgtccc 50

<210> SEQ ID NO 40
<211> LENGTH: 55
<212> TYPE: DNA
<213> ORGANISM: Artificial Sequence
<220> FEATURE:
<223> OTHER INFORMATION: GFP-rv

<400> SEQUENCE: 40
cagctgctgg gattacacat ggcatggatg aactatacaa agcggccgcg gatcc 55

<210> SEQ ID NO 41
<211> LENGTH: 263
<212> TYPE: PRT
<213> ORGANISM: Artificial Sequence
<220> FEATURE:
<223> OTHER INFORMATION: pSEX-pelB-GFP

<400> SEQUENCE: 41

Met Lys Tyr Leu Leu Pro Thr Ala Ala Ala Gly Leu Leu Leu Leu Ala
1 5 10 15

Ala Gln Pro Ala Met Ala Ala Ser Lys Gly Glu Glu Leu Phe Thr Gly
20 25 30

Val Val Pro Ile Leu Val Glu Leu Asp Gly Asp Val Asn Gly His Lys
35 40 45

Phe Ser Val Ser Gly Glu Gly Glu Gly Asp Ala Thr Tyr Gly Lys Leu
50 55 60

Thr Leu Lys Phe Ile Cys Thr Thr Gly Lys Leu Pro Val Pro Trp Pro
65 70 75 80

Thr Leu Val Thr Thr Leu Thr Tyr Gly Val Gln Cys Phe Ser Arg Tyr
85 90 95

Pro Asp His Met Lys Arg His Asp Phe Phe Lys Ser Ala Met Pro Glu
100 105 110

Gly Tyr Val Gln Glu Arg Thr Ile Ser Phe Lys Asp Asp Gly Asn Tyr
115 120 125

Lys Thr Arg Ala Glu Val Lys Phe Glu Gly Asp Thr Leu Val Asn Arg
130 135 140

Ile Glu Leu Lys Gly Ile Asp Phe Lys Glu Asp Gly Asn Ile Leu Gly
145 150 155 160

His Lys Leu Glu Tyr Asn Tyr Asn Ser His Asn Val Tyr Ile Thr Ala
165 170 175

Asp Lys Gln Lys Asn Gly Ile Lys Ala Asn Phe Lys Ile Arg His Asn
180 185 190

Ile Glu Asp Gly Ser Val Gln Leu Ala Asp His Tyr Gln Gln Asn Thr
195 200 205

Pro Ile Gly Asp Gly Pro Val Leu Leu Pro Asp Asn His Tyr Leu Ser
210 215 220

Thr Gln Ser Ala Leu Ser Lys Asp Pro Asn Glu Lys Arg Asp His Met
225 230 235 240

Val Leu Leu Glu Phe Val Thr Ala Ala Gly Ile Thr His Gly Met Asp
245 250 255

Glu Leu Tyr Lys Ala Ala Ala
260

<210> SEQ ID NO 42
<211> LENGTH: 283
<212> TYPE: PRT
<213> ORGANISM: Artificial Sequence
<220> FEATURE:
<223> OTHER INFORMATION: pSEX-TorA7I-GFP

<400> SEQUENCE: 42

Met Asn Asn Asn Asp Leu Phe Gln Thr Ser Arg Gln Arg Phe Leu Ala
1 5 10 15

Gln Leu Gly Gly Leu Thr Val Ala Gly Met Leu Gly Pro Ser Leu Leu
20 25 30

Thr Pro Arg Arg Ala Thr Ala Ala Met Ala Ala Ser Lys Gly Glu Glu
35 40 45

Leu Phe Thr Gly Val Val Pro Ile Leu Val Glu Leu Asp Gly Asp Val
50 55 60

Asn Gly His Lys Phe Ser Val Ser Gly Glu Gly Glu Gly Asp Ala Thr
65 70 75 80

Tyr Gly Lys Leu Thr Leu Lys Phe Ile Cys Thr Thr Gly Lys Leu Pro
85 90 95

Val Pro Trp Pro Thr Leu Val Thr Thr Leu Thr Tyr Gly Val Gln Cys
100 105 110

Phe Ser Arg Tyr Pro Asp His Met Lys Arg His Asp Phe Phe Lys Ser
115 120 125

Ala Met Pro Glu Gly Tyr Val Gln Glu Arg Thr Ile Ser Phe Lys Asp
130 135 140

Asp Gly Asn Tyr Lys Thr Arg Ala Glu Val Lys Phe Glu Gly Asp Thr
145 150 155 160

Leu Val Asn Arg Ile Glu Leu Lys Gly Ile Asp Phe Lys Glu Asp Gly
165 170 175

Asn Ile Leu Gly His Lys Leu Glu Tyr Asn Tyr Asn Ser His Asn Val
180 185 190

Tyr Ile Thr Ala Asp Lys Gln Lys Asn Gly Ile Lys Ala Asn Phe Lys
195 200 205

Ile Arg His Asn Ile Glu Asp Gly Ser Val Gln Leu Ala Asp His Tyr
210 215 220

Gln Gln Asn Thr Pro Ile Gly Asp Gly Pro Val Leu Leu Pro Asp Asn
225 230 235 240

His Tyr Leu Ser Thr Gln Ser Ala Leu Ser Lys Asp Pro Asn Glu Lys
245 250 255

Arg Asp His Met Val Leu Leu Glu Phe Val Thr Ala Ala Gly Ile Thr
260 265 270

His Gly Met Asp Glu Leu Tyr Lys Ala Ala Ala
275 280

<210> SEQ ID NO 43
<211> LENGTH: 286
<212> TYPE: PRT
<213> ORGANISM: Artificial Sequence
<220> FEATURE:
<223> OTHER INFORMATION: pSEX-TorA7II-GFP

<400> SEQUENCE: 43

Met Asn Asn Asn Asp Leu Phe Gln Thr Ser Arg Gln Arg Phe Leu Ala

```
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala Ala Met Ala Ala Ser Lys
        35                  40                  45

Gly Glu Glu Leu Phe Thr Gly Val Val Pro Ile Leu Val Glu Leu Asp
    50                  55                  60

Gly Asp Val Asn Gly His Lys Phe Ser Val Ser Gly Glu Gly Glu Gly
65                  70                  75                  80

Asp Ala Thr Tyr Gly Lys Leu Thr Leu Lys Phe Ile Cys Thr Thr Gly
                85                  90                  95

Lys Leu Pro Val Pro Trp Pro Thr Leu Val Thr Thr Leu Thr Tyr Gly
            100                 105                 110

Val Gln Cys Phe Ser Arg Tyr Pro Asp His Met Lys Arg His Asp Phe
        115                 120                 125

Phe Lys Ser Ala Met Pro Glu Gly Tyr Val Gln Glu Arg Thr Ile Ser
    130                 135                 140

Phe Lys Asp Asp Gly Asn Tyr Lys Thr Arg Ala Glu Val Lys Phe Glu
145                 150                 155                 160

Gly Asp Thr Leu Val Asn Arg Ile Glu Leu Lys Gly Ile Asp Phe Lys
                165                 170                 175

Glu Asp Gly Asn Ile Leu Gly His Lys Leu Glu Tyr Asn Tyr Asn Ser
            180                 185                 190

His Asn Val Tyr Ile Thr Ala Asp Lys Gln Lys Asn Gly Ile Lys Ala
        195                 200                 205

Asn Phe Lys Ile Arg His Asn Ile Glu Asp Gly Ser Val Gln Leu Ala
    210                 215                 220

Asp His Tyr Gln Gln Asn Thr Pro Ile Gly Asp Gly Pro Val Leu Leu
225                 230                 235                 240

Pro Asp Asn His Tyr Leu Ser Thr Gln Ser Ala Leu Ser Lys Asp Pro
                245                 250                 255

Asn Glu Lys Arg Asp His Met Val Leu Leu Glu Phe Val Thr Ala Ala
            260                 265                 270

Gly Ile Thr His Gly Met Asp Glu Leu Tyr Lys Ala Ala Ala
        275                 280                 285


<210> SEQ ID NO 44
<211> LENGTH: 45
<212> TYPE: DNA
<213> ORGANISM: Artificial Sequence
<220> FEATURE:
<223> OTHER INFORMATION: Original AviTag

<400> SEQUENCE: 44

ggtctgaacg acatcttcga ggctcagaaa atcgaatggc acgaa                    45


<210> SEQ ID NO 45
<211> LENGTH: 45
<212> TYPE: DNA
<213> ORGANISM: Artificial Sequence
<220> FEATURE:
<223> OTHER INFORMATION: Modified AviTag sequence

<400> SEQUENCE: 45

ggcctgaacg atatctttga agcgcagaaa attgaatggc atgaa                    45


<210> SEQ ID NO 46
```

```
<211> LENGTH: 15
<212> TYPE: PRT
<213> ORGANISM: Artificial Sequence
<220> FEATURE:
<223> OTHER INFORMATION: AviTag

<400> SEQUENCE: 46

Gly Leu Asn Asp Ile Phe Glu Ala Gln Lys Ile Glu Trp His Glu
1               5                   10                  15


<210> SEQ ID NO 47
<211> LENGTH: 24
<212> TYPE: DNA
<213> ORGANISM: Artificial Sequence
<220> FEATURE:
<223> OTHER INFORMATION: codon optimised FLAG peptide

<400> SEQUENCE: 47

gactacaagg acgatgacga caag                                            24


<210> SEQ ID NO 48
<211> LENGTH: 8
<212> TYPE: PRT
<213> ORGANISM: Artificial Sequence
<220> FEATURE:
<223> OTHER INFORMATION: codon optimised FLAG peptide

<400> SEQUENCE: 48

Asp Tyr Lys Asp Asp Asp Asp Lys
1               5


<210> SEQ ID NO 49
<211> LENGTH: 18
<212> TYPE: DNA
<213> ORGANISM: Artificial Sequence
<220> FEATURE:
<223> OTHER INFORMATION: codon optimised HIS6 peptide

<400> SEQUENCE: 49

catcaccatc accatcac                                                   18


<210> SEQ ID NO 50
<211> LENGTH: 6
<212> TYPE: PRT
<213> ORGANISM: Artificial Sequence
<220> FEATURE:
<223> OTHER INFORMATION: codon optimised HIS6 tag

<400> SEQUENCE: 50

His His His His His His
1               5


<210> SEQ ID NO 51
<211> LENGTH: 8
<212> TYPE: PRT
<213> ORGANISM: Artificial Sequence
<220> FEATURE:
<223> OTHER INFORMATION: Biotin Strep-tag

<400> SEQUENCE: 51

Trp Ser His Pro Gln Phe Glu Lys
1               5
```